(12) United States Patent
Lamego et al.

(10) Patent No.: US 10,646,144 B2
(45) Date of Patent: May 12, 2020

(54) WIRELESS, DISPOSABLE, EXTENDED USE PULSE OXIMETER APPARATUS AND METHODS

(71) Applicants: Marcelo Malini Lamego, Mission Viejo, CA (US); Tatiana Buticosky Lamego, Mission Viejo, CA (US)

(72) Inventors: Marcelo Malini Lamego, Mission Viejo, CA (US); Tatiana Buticosky Lamego, Mission Viejo, CA (US)

(*) Notice: Subject to any disclaimer, the term of this patent is extended or adjusted under 35 U.S.C. 154(b) by 312 days.

(21) Appl. No.: 15/372,341

(22) Filed: Dec. 7, 2016

(65) Prior Publication Data
US 2018/0110450 A1 Apr. 26, 2018

Related U.S. Application Data

(60) Provisional application No. 62/264,233, filed on Dec. 7, 2015.

(51) Int. Cl.
*A61B 5/1455* (2006.01)
*A61B 5/00* (2006.01)
(Continued)

(52) U.S. Cl.
CPC .......... *A61B 5/14552* (2013.01); *A61B 5/002* (2013.01); *A61B 5/0004* (2013.01);
(Continued)

(58) Field of Classification Search
CPC .............. A61B 5/14552; A61B 5/6832; A61B 5/02438; A61B 5/02416; A61B 5/002;
(Continued)

(56) References Cited

U.S. PATENT DOCUMENTS 2,567,926 A 9/1951 Dunkelberger
2,706,927 A 4/1955 Howard
(Continued)

FOREIGN PATENT DOCUMENTS

EP 3386390 10/2017
GB 2560482 9/2018
(Continued)

OTHER PUBLICATIONS

Owlet Smart Sock1/ Smart Sock 2, http://www.owletcare.com/smart-sock-2/, Mar. 15, 2017.
(Continued)

*Primary Examiner* — Eric F Winakur
*Assistant Examiner* — Abid A Mustansir
(74) *Attorney, Agent, or Firm* — Merchant & Gould P.C.

(57) ABSTRACT

Apparatus and methods provide wireless, disposable, continuous pulse oximeter sensor technology, useful and beneficial for a number of applications including relatively extended periods of data collection, and/or packaged in compact and easy-to-use assemblies. Economic fabrication and use provides flexible methodologies that can reduce the overall costs of monitoring and collecting patient's physiological data, and provide relatively greater ease and comfort to the patient. A disposable wireless continuous pulse oximeter sensor has a reduced emitter-detector separation, a low-power frontend, and a low-cost processor that sends waveforms to a host device so that the host can calculate and display the parameters of interest. Complications created by the reduced distance between emitter and detector are minimized by using an emitter-detector assembly with an optically dark background, and a bandage for improved optical compliance.

28 Claims, 70 Drawing Sheets

(51) Int. Cl.
*A61B 5/024* (2006.01)
*G01J 3/10* (2006.01)
*G16H 40/67* (2018.01)
*G01J 3/42* (2006.01)
*G01J 3/02* (2006.01)

(52) U.S. Cl.
CPC ........ *A61B 5/0022* (2013.01); *A61B 5/02416* (2013.01); *A61B 5/02427* (2013.01); *A61B 5/4806* (2013.01); *A61B 5/6832* (2013.01); *A61B 5/68335* (2017.08); *G01J 3/027* (2013.01); *G01J 3/10* (2013.01); *G01J 3/42* (2013.01); *G16H 40/67* (2018.01); *A61B 5/02438* (2013.01); *A61B 5/6814* (2013.01); *A61B 5/6822* (2013.01); *A61B 5/6824* (2013.01); *A61B 5/6826* (2013.01); *A61B 5/746* (2013.01); *A61B 5/7435* (2013.01); *A61B 2505/07* (2013.01); *A61B 2560/0209* (2013.01); *A61B 2560/0285* (2013.01); *A61B 2562/0295* (2013.01); *A61B 2562/166* (2013.01); *A61B 2562/185* (2013.01); *G01J 2003/104* (2013.01)

(58) Field of Classification Search
CPC .............. A61B 5/68335; A61B 5/4806; A61B 5/02427; A61B 5/0022; A61B 5/0004; A61B 5/7435; A61B 5/6826; G16H 40/67; G01J 3/027; G01J 3/42; G01J 3/10; G01J 2003/104; G06F 19/00
See application file for complete search history.

(56) References Cited

U.S. PATENT DOCUMENTS

| | | | |
|---|---|---|---|
| 3,704,706 | A | 12/1972 | Herczfeld et al. |
| 3,847,483 | A | 11/1974 | Sidlauskas et al. |
| 4,321,930 | A | 3/1982 | Jobsis et al. |
| 4,380,240 | A | 4/1983 | Jobsis et al. |
| 4,621,643 | A | 11/1986 | New et al. |
| 4,700,708 | A | 10/1987 | New et al. |
| 4,770,179 | A | 9/1988 | New et al. |
| 4,830,014 | A | 5/1989 | Goodman et al. |
| 4,865,038 | A | 9/1989 | Rich et al. |
| 4,867,165 | A | 9/1989 | Noller et al. |
| 4,907,594 | A | 3/1990 | Muz |
| 4,964,408 | A | 10/1990 | Hink et al. |
| 5,041,187 | A | 8/1991 | Hink et al. |
| 5,090,410 | A | 2/1992 | Saper et al. |
| 5,094,240 | A | 3/1992 | Muz |
| 5,111,817 | A | 5/1992 | Clark et al. |
| 5,125,403 | A | 6/1992 | Culp |
| 5,170,786 | A | 12/1992 | Thomas et al. |
| 5,209,230 | A | 5/1993 | Swedlow et al. |
| 5,217,012 | A | 6/1993 | Young et al. |
| 5,246,003 | A | 9/1993 | Delonzor |
| 5,249,576 | A | 10/1993 | Goldberger et al. |
| 5,337,744 | A | 8/1994 | Branigan |
| 5,368,025 | A * | 11/1994 | Young ................ A61B 5/02427 356/41 |
| 5,392,777 | A | 2/1995 | Swedlow et al. |
| 5,425,360 | A | 6/1995 | Nelson |
| 5,429,129 | A | 7/1995 | Lovejoy et al. |
| 5,437,275 | A | 8/1995 | Amundsen et al. |
| 5,452,717 | A | 9/1995 | Branigan et al. |
| 5,469,845 | A | 11/1995 | Delonzor et al. |
| 5,511,554 | A | 4/1996 | Helfenbein et al. |
| 5,544,661 | A | 8/1996 | Davis et al. |
| 5,590,648 | A | 1/1997 | Mitchell et al. |
| 5,645,059 | A | 7/1997 | Fein et al. |
| 5,660,567 | A | 8/1997 | Nierlich et al. |
| 5,671,529 | A | 9/1997 | Nelson |
| 5,673,692 | A | 10/1997 | Schulze et al. |
| 5,673,693 | A | 10/1997 | Solenberger |
| 5,678,544 | A | 10/1997 | Delonzor et al. |
| 5,687,717 | A | 11/1997 | Halpern et al. |
| 5,758,644 | A | 6/1998 | Diab et al. |
| 5,779,630 | A | 7/1998 | Fein et al. |
| 5,782,757 | A | 7/1998 | Diab et al. |
| 5,817,008 | A * | 10/1998 | Rafert ................ A61B 5/14552 600/323 |
| 5,830,136 | A * | 11/1998 | Delonzor ........... A61B 5/14552 600/323 |
| RE36,000 | E | 12/1998 | Swedlow et al. |
| 5,865,736 | A | 2/1999 | Baker et al. |
| 5,891,021 | A | 4/1999 | Dillon et al. |
| 5,910,108 | A | 6/1999 | Solenberger |
| 5,999,834 | A | 7/1999 | Wang et al. |
| 6,006,120 | A | 12/1999 | Levin |
| 6,018,673 | A | 1/2000 | Chin et al. |
| 6,061,584 | A | 5/2000 | Lovejoy et al. |
| 6,119,027 | A | 9/2000 | Selenberger |
| 6,144,868 | A | 11/2000 | Parker |
| 6,178,343 | B1 | 1/2001 | Bindszus et al. |
| 6,215,403 | B1 | 4/2001 | Chan et al. |
| 6,253,097 | B1 | 6/2001 | Aronow et al. |
| 6,256,523 | B1 | 7/2001 | Diab et al. |
| 6,285,492 | B1 * | 9/2001 | Good ..................... H01M 6/30 359/297 |
| 6,343,224 | B1 | 1/2002 | Parker |
| 6,374,129 | B1 | 4/2002 | Chin et al. |
| 6,377,829 | B1 | 4/2002 | Al-Ali |
| 6,519,487 | B1 | 2/2003 | Parker |
| 6,546,267 | B1 | 4/2003 | Sugiura et al. |
| 6,612,984 | B1 | 9/2003 | Robert |
| 6,671,531 | B2 | 12/2003 | Al-Ali et al. |
| 6,678,543 | B2 | 1/2004 | Diab et al. |
| 6,681,126 | B2 | 1/2004 | Solenberger |
| 6,720,734 | B2 | 4/2004 | Norris |
| 6,725,075 | B2 | 4/2004 | Al-Ali |
| 6,731,962 | B1 | 5/2004 | Katarow et al. |
| 6,735,459 | B2 | 5/2004 | Parker |
| 6,745,061 | B1 | 6/2004 | Hicks et al. |
| 6,748,254 | B2 | 6/2004 | O'Neill et al. |
| 6,845,256 | B2 | 1/2005 | Chin et al. |
| 6,942,616 | B2 | 9/2005 | Robert |
| 7,039,449 | B2 | 5/2006 | Al-Ali |
| 7,113,815 | B2 | 9/2006 | O'Neil et al. |
| 7,186,966 | B2 | 3/2007 | Al-Ali |
| 7,191,013 | B1 * | 3/2007 | Miranda ............... A61B 5/0031 607/60 |
| 7,206,630 | B1 | 4/2007 | Tarker |
| 7,295,866 | B2 | 11/2007 | Al-Ali |
| 7,387,607 | B2 | 6/2008 | Holt et al. |
| 7,486,977 | B2 | 2/2009 | Sweitzer et al. |
| 7,499,739 | B2 | 3/2009 | Sweitzer et al. |
| 7,555,327 | B2 | 6/2009 | Tang et al. |
| 7,668,588 | B2 | 2/2010 | Kovacs |
| RE41,912 | E | 11/2010 | Parker |
| 7,904,131 | B2 | 3/2011 | Mannheimer et al. |
| 7,957,781 | B2 | 6/2011 | Mannheimer et al. |
| 8,018,776 | B2 | 9/2011 | Miyake et al. |
| 8,157,730 | B2 | 4/2012 | LeBoeuf et al. |
| 8,200,320 | B2 | 6/2012 | Kovacs |
| 8,214,007 | B2 | 7/2012 | Baker et al. |
| 8,326,392 | B2 | 12/2012 | Grubac et al. |
| 8,437,824 | B2 | 5/2013 | Moon et al. |
| 8,444,578 | B2 | 5/2013 | Bourget et al. |
| 8,457,704 | B2 | 6/2013 | Sweitzer et al. |
| 8,668,643 | B2 | 3/2014 | Kinast |
| 8,688,187 | B2 | 4/2014 | DelloStritto et al. |
| 8,727,977 | B2 | 5/2014 | Banet et al. |
| 8,750,954 | B2 | 6/2014 | Peterson et al. |
| 8,761,852 | B2 | 6/2014 | Parthasarathy et al. |
| 8,764,671 | B2 | 7/2014 | Kiani |
| 8,808,188 | B2 | 8/2014 | Banet et al. |
| 8,886,271 | B2 | 11/2014 | Kiani et al. |
| 8,903,467 | B2 | 12/2014 | Sweitzer et al. |
| 8,932,217 | B2 | 1/2015 | Gibson et al. |
| 8,965,492 | B2 | 2/2015 | Baker et al. |
| 8,983,564 | B2 | 3/2015 | Al-Ali |
| 9,028,405 | B2 | 5/2015 | Tran |

(56) References Cited

U.S. PATENT DOCUMENTS

| | | | |
|---|---|---|---|
| 9,039,627 | B2 | 5/2015 | Rulkov et al. |
| 9,042,952 | B2 | 5/2015 | Lynn et al. |
| 9,107,586 | B2 | 8/2015 | Tran |
| 9,155,484 | B2 | 10/2015 | Baker et al. |
| 10,194,847 | B2 | 2/2019 | Al-Ali |
| 10,194,848 | B1 | 2/2019 | Kiani et al. |
| 2002/0069885 | A1 | 6/2002 | Boies et al. |
| 2003/0033102 | A1 | 2/2003 | Dietiker |
| 2004/0102687 | A1 | 5/2004 | Brashears et al. |
| 2004/0117204 | A1 | 6/2004 | Mazar et al. |
| 2004/0127775 | A1 | 7/2004 | Miyazaki et al. |
| 2004/0172290 | A1 | 9/2004 | Leven |
| 2004/0242976 | A1 | 12/2004 | Abreu |
| 2004/0260161 | A1 | 12/2004 | Melker et al. |
| 2005/0010087 | A1 | 1/2005 | Banet et al. |
| 2005/0038326 | A1 | 2/2005 | Mathur |
| 2005/0043640 | A1 | 2/2005 | Chang |
| 2005/0070775 | A1 | 3/2005 | Chin et al. |
| 2005/0113655 | A1 | 5/2005 | Hull |
| 2005/0197550 | A1 | 6/2005 | Al-Ali et al. |
| 2005/0228298 | A1 | 10/2005 | Banet et al. |
| 2005/0228299 | A1 | 10/2005 | Banet |
| 2005/0234317 | A1 | 10/2005 | Kiani |
| 2006/0224058 | A1* | 10/2006 | Mannheimer ...... A61B 5/14552 600/323 |
| 2007/0142717 | A1* | 6/2007 | Lowery ............. A61B 5/14552 600/323 |
| 2007/0208233 | A1* | 9/2007 | Kovacs ................ A61B 5/0205 600/300 |
| 2009/0326354 | A1* | 12/2009 | Mao .................... A61B 5/14532 600/344 |
| 2010/0109966 | A1* | 5/2010 | Mateychuk ......... A61N 1/37229 343/841 |
| 2010/0210924 | A1* | 8/2010 | Parthasarathy ...... A61B 5/0002 600/301 |
| 2010/0317936 | A1* | 12/2010 | Al-Ali ................ A61B 5/02444 600/323 |
| 2011/0028811 | A1 | 2/2011 | Mazda et al. |
| 2011/0137297 | A1 | 6/2011 | Kiani et al. |
| 2011/0208018 | A1 | 8/2011 | Kiani et al. |
| 2011/0213225 | A1* | 9/2011 | Bernstein ............... G06Q 50/22 600/309 |
| 2012/0315554 | A1* | 12/2012 | Christensen ........ H01M 2/1673 429/405 |
| 2013/0046163 | A1 | 2/2013 | Sweitzer et al. |
| 2013/0253334 | A1 | 9/2013 | Al-Ali et al. |
| 2014/0134375 | A1* | 5/2014 | Guillo ........................ C09J 7/21 428/43 |
| 2014/0200420 | A1 | 7/2014 | Ai-Ali |
| 2015/0157263 | A1 | 6/2015 | Workman et al. |
| 2015/0208933 | A1 | 7/2015 | Satomi et al. |
| 2016/0015289 | A1 | 1/2016 | Simon et al. |
| 2017/0079586 | A1 | 3/2017 | Geva et al. |

FOREIGN PATENT DOCUMENTS

| | | |
|---|---|---|
| WO | 20030031961 | 4/2003 |
| WO | 2017100707 | 6/2017 |

OTHER PUBLICATIONS

Flexzion Fingertip Pulse Oximeter CMS-50DL, https://www.amazon.com/dp/B014SKLRPE, Mar. 15, 2017.

Zaccurate Pro Series Finger Heart Rate Monitor and Blood HbO2 Meter, https://www.amazon.com/Zacurate-Fingertip-Oximeter-Saturation-batteries/dp/B01EK58YXK, Mar. 15, 2017.

Easy@Home Deluxe Fingertip Pulse Oximeter EHP50D1, https://www.amazon.com/Easy-Home-Fingertip-Oximeter-Directions/dp/B00KGP7L38, Mar. 15, 2017.

Areta Fingertip Pulse Oximeter EZD-500A, https://www.amazon.com/Areta-Fingertip-Oximeter-Dual-color-Directions/dp/B00TP1NEGM, Mar. 15, 2017.

Santamedical Generation 2 SM-165 Fingertip Pulse Oximeter, https://www.amazon.com/Santamedical-Generation-SM-165-Fingertip-Saturation/dp/B00R59OTOC, Mar. 15, 2017.

Santamedical Generation 2 OLED Fingertip Pulse Oximeter, https://www.amazon.com/Santamedical-Generation-Fingertip-Saturation-batteries/dp/B018HC7H6C, Mar. 15, 2017.

OxiMed Smart Pulse Advanced Pulse Oximeter, https://www.amazon.com/SmartPulse-Advanced-Finger-Pulse-Oximeter/dp/B01BMUJQLU, Mar. 15, 2017.

Concord Health Supply Fingertip Pulse Oximeter, https://www.concordhealthsupply.com/Concord-Pink-Finger-Pulse-Oximeter-p/cci-300-pink.htm, Mar. 15, 2017.

Careshine OLED Fingertip Pulse Oximeter, https://www.amazon.com/Careshine-approved-Fingertip-Pulse-Oximeter/dp/B016W2V7P6, Mar. 15, 2017.

Acc U Rate 430 DL Premium Fingertip Pulse Oximeter, https://www.amazon.com/Acc-Rate-Fingertip-Saturation-batteries/dp/B06VWJ4T4T?th=1, Mar. 15, 2017.

AccuMed CMS 50 D1 Fingertip Pulse Oximeter, https://www.amazon.com/AccuMed-CMS-50DL-Oximeter-Aviation-Carrying/dp/B00MNRSWJE, Mar. 15, 2017.

Jumper JPD 500-D Digital Fingertip Pulse Oximeter, https://www.amazon.com/JPD-500D-Approved-Finger-Oximeter-Monitor/dp/B011MVBG5S, Mar. 15, 2017.

Medi-K Fingertip Pulse Oximeter, https://www.amazon.com/Generation-Fingertip-Saturation-Multidirection-Batteries/dp/B01NCA9FJ1, Mar. 15, 2017.

iHealth Air Pulse Oximeter for Apple and Android, https://www.amazon.com/iHealth-Pulse-Oximeter-Apple-Android/dp/B00D7MDXCU, Mar. 15, 2017.

The Kenek Edge iPhone Oximeter, https://www.amazon.com/LGTmedical-Kenek-Edge-Pulse-Oximeter/dp/B00L788XVW, Mar. 15, 2017.

Safe Heart iOximeter, http://safeheartus.com/ioximeter/, Mar. 15, 2017.

Invacare 8610 Digit-Ox2 Fingertip Pulse Oximeter, https://www.cascadehealthcaresolutions.com/digit-ox2-pulse-oximeter-p/ISG8610.htm?_vsrefdom=adwords&gclid=Cj0KEQjwuZvIBRD-8Z6B2M2Sy68BEiQAtjYS3A2_IoZxh4a8WGpvnzLykHA72iFuLxvkdwaI9bnm0acaAhhu8P8HAQ, Mar. 15, 2017.

Homedics Deluxe Fingertip Pulse Oximeter Reflective, https://www.amazon.com/Homedics-Px-100-Oximeter-Optimetrix-Technology/dp/B00C4VX3OS, Mar. 15, 2017.

MeasuPro Instant Read Digital Fingertip Pulse Oximeter, https://www.amazon.com/MeasuPro-Instant-Digital-Oximeter-Approved/dp/B017C0AB2C, Mar. 15, 2017.

Omron 300C20-OTC & NMR Fingertip Pulse Oximeters, http://www.amazon.in/Omron-Choicemmed-Pulse-Oximeter-Yellow/dp/B00SMBL5SK, Mar. 15, 2017.

Spirodoc Oxi for Sleep Analysis and 6-Minute Walk Test, https://www.spirometry.com/ENG/products/spirodoc_new.asp, Mar. 15, 2017.

MedChoice MD300C318T Fingertip Pulse Oximeter, http://www.pulsoximeter-gerate.com/MD300C318T.asp, Mar. 15, 2017.

American Diagnostic Corporation Advantage 2200 Fingertip Pulse Oximeter, http://adctoday.com/products/2200, Mar. 15, 2017.

American Diagnostic Corporation Diagnostix 2100 Digital Fingertip Pulse Oximeter, http://adctoday.com/products/2100, Mar. 15, 2017.

American Diagnostic Corporation Adimals 2150 Fingertip Pulse Oximeter, http://adctoday.com/products/2150, Mar. 15, 2017.

Edan H10 Fingertip Pulse Oximeter, http://www.edan-instruments.com/enproduct.aspx?NodeID=198&cid=384, Mar. 15, 2017.

Edan H100 N Handheld Pulse Oximeter, http://www.edan.com.cn/detail.aspx?cid=444, Mar. 15, 2017.

Edan H100B Handheld Pulse Oximeter, http://www.edanusa.com/brochures/brochure_3623_a.pdf, Mar. 15, 2017.

Edan M3M3A/M3S Vital Signs Monitor, http://www.edan.com.cn/html/EN/produds/patientmonitoring/, Mar. 15, 2017.

SPO Checkmate Fingertip Pulse Oximeter, https://www.turnermedical.com/SPO_CHECKMATE_CM1000_FINGER_PULSE_OXIMETER_p/spo_cm1000_checkmate.htm, Mar. 15, 2017.

(56) References Cited

OTHER PUBLICATIONS

Devon Medical Medical DT100A Fingertip Pulse Oximeter, https://www.walmart.com/ip/Devon-Medical-Fingertip-Pulse-Oximeter-DT100-A/35514879, Mar. 15, 2017.
Devon SPO Medical 5500 Fingertip Pulse Oximeter, https://www.turnermedical.com/SPO_MEDICAL_5500_FINGER_PULSE_OXIMETER_p/spo_5500.htm, Mar. 15, 2017.
Devon Medical PC60C Fingertip Pulse Oximeter, http://www.devonsuperstore.com/Fingertip-Pulse-Oximeters-C8.aspx, Mar. 15, 2017.
Devon Medical Handheld Pulse Oximeter DTPC66, http://www.devonsuperstore.com/PC-66-Handheld-Pulse-Oximeter-FDA-Approved-P73.aspx, Mar. 15, 2017.
Choicemmed OxxiWatch C20SM Fingertip Pulse Oximeter, https://www.walmart.com/ip/CHOICEMMED-OxyWatch-C20SM-Fingertip-Pulse-Oximeter/15443473, Mar. 15, 2017.
Choicemmed OxyWatch C18SM Fingertip Pulse Oximeter, https://www.walmart.com/ip/CHOICEMMED-OxyWatch-C18SM-Fingertip-Pulse-Oximeter/15443474, Mar. 15, 2017.
Quest 3-in-1 Fingertip Pulse Oximeter, https://www.amazon.com/Quest-Q1911-3-in-1-Pulse-Oximeter/dp/B004XH55QK Mar. 15, 2017.
SmartHeart Pulse Oximeter, https://www.walmart.com/ip/SmartHeart-Pulse-Oximeter/20611246, Mar. 15, 2017, Mar. 15, 2017.
NatureSpirit Bluetooth Wireless Fingertip Pulse Oximeter, https://www.walmart.com/ip/NatureSpirit-Bluetooth-Wireless-Fingertip-Pulse-Oximeter/15550443, Mar. 15, 2017, Mar. 15, 2017.
Veridian Premium Fingertip Pulse Oximeter, https://www.walmart.com/ip/Premium-Pulse-Oximeter/20611247?wmlspartner=wlspa&selectedSellerId=1131&adid=22222222227015135369&wl0=&lwl1=g&wl2=c&wl3=40754308112&wl4=pla-78606690752&wl5=9028773&wl6=&wl7=&wl8=8&wl9=pla&wl10=112562428&wl11=online&wl12=20611247&wl13=&veh=sem, Mar. 15, 2017.
Medline Easy-Grip Fingertip Pulse Oximeter, https://www.medline.com/product/Fingertip-Pulse-Oximeter/Pulse-Oximetry/Z05-PF54728, Mar. 15, 2017.
Medline PulSTAT Fingertip Pulse Oximeter, https://www.medline.com/product/pulSTAT-Finger-Pulse-Oximeter/Pulse-Oximetry/Z05-PF137460?question=&index=P7&indexCount=7, Mar. 15, 2017.
Medline Soft Touch Fingertip Pulse Oximeter http://www.medline.com/product/Soft-Touch-Finger-Pulse-Oximeter/Pulse-Oximetry/Z05-PF91075, Mar. 15, 2017.
Medline Basic Fingertip Pulse Oximeter, http://www.medline.com/product/Basic-Finger-Pulse-Oximeter/Z05-PF129389, Mar. 15, 2017.
Medline High Impact Fingertip Pulse Oximeter, https://www.medline.com/product/High-Impact-Finger-Pulse-Oximeter/Pulse-Oximetry/Z05-PF04311, Mar. 15, 2017.
Medline Pediatric Fingertip Pulse Oximeter, http://www.medline.com/product/Pediatric-Finger-Pulse-Oximeter/Z05-PF137459, Mar. 15, 2017.
Medline Handheld Continuous Pulse Oximeter, http://www.medline.com/product/Handheld-Continuous-Pulse-Oximeter/Z05-PF137458, Mar. 15, 2017.
Medline Handheld Spot-Check Pulse Oximeter, http://www.medline.com/product/Handheld-Spot-Check-Oximeter/Z05-PF04320, Mar. 15, 2017.
Smiths Medical BCI Digit Fingertip Pulse Oximeter, https://www.smiths-medical.com/products/patient-monitoring/capnographs/finger-pulse-oximiters/digit-finger-oximeter, Mar. 15, 2017.
Smiths Medical BCI Spectro2 10 Handheld Pulse Oximeter, https://www.smiths-medical.com/products/patient-monitoring/pulse-oximeters/oximeters/spectro2-10-pulse-oximeter, Mar. 15, 2017.
Smiths Medical BCI Spectro2 20 Handheld Pulse Oximeter, https://www.smiths-medical.com/products/patient-monitoring/pulse-oximeters/oximeters/spectro2-20-pulse-oximeter, Mar. 15, 2017.
Smiths Medical BCI Spectro2 30 Handheld Pulse Oximeter, https://www.smiths-medical.com/products/patient-monitoring/pulse-oximeters/oximeters/spectro2-30-pulse-oximeter, Mar. 15, 2017.
Smiths Medical BCI AutoCorr Digital Pulse Oximeter, https://www.smiths-medical.com/products/patient-monitoring/pulse-oximeters/bedside-pulse-oximiters/bci-autocorr-digital-pulse-oximeter, Mar. 15, 2017.
Solaris Handheld Capnography/Pulse Oximeter Monitor NT1D, http://www.aedsuperstore.com/solaris-medical-technology-nt1d-capnography-pulse-oximetry-hand-held-monitor.html, Mar. 15, 2017.
Solaris Handheld Pulse Oximeter, http://www.aedsuperstore.com/solaris-medical-technology-pulse-oximeter-hand-held-alarm-option.html?ctm_campaigntype=non-branded&gclid=Cj0KEQjwuZvIBRD-_8Z6B2M2Sy68BEiQAtjYS3JupmjK4ZG4fWprhoUD25PBeurZ8sbl4dZDhPV3JdNQaAiHz8P8HAQ, Mar. 15, 2017.
Solaris NT2A Portable Pulse Oximeter, http://www.solarismedtech.com/solaris_medical_devices/NT2A.html, Mar. 15, 2017.
NT2C Portable Vital Signs Monitor, http://www.solarismedtech.com/solaris_medical_devices/NT2C.html, Mar. 15, 2017.
Nellcor Oximax N-65, http://www.medtronic.com/content/dam/covidien/library/us/en/legacyimport/patientmonitoringrecovery/rms/3/nellcor-oximax-n65-portable-puke-ox-brochure.pdf, Mar. 15, 2017.
Nellcor Portable SpO2 Patient Monitoring System PM10n (Covidien), http://www.medtronic.com/covidien/products/pulse-oximetry/nellcor-portable-spo2-patient-monitoring-system, Mar. 15, 2017.
Nellcor Bedside Respiratory Patient Monitoring System PM1000N, http://www.medtronic.com/covidien/products/pulse-oximetry/nellcor-bedside-respiratory-patient-monitoring-system-pm1000n, Mar. 15, 2017.
Nellcor Bedside SPO2 Patient Monitoring System PM100N, http://www.medtronic.com/covidien/products/pulse-oximetry/nellcor-bedside-spo2-patient-monitoring-system-pm100n, Mar. 15, 2017.
Nellcor Bedside SPO2 Patient Monitoring System, http://www.medtronic.com/covidien/products/pulse-oximetry/nellcor-bedside-spo2-patient-monitoring-system, Mar. 15, 2017.
Nellcor Oximax N-595, http://pacificmedicalsupply.com/nellcor-n-595-pulse-oximeter/, Mar. 15, 2017.
Nellcor N-395 Pulse Oximeter, http://pacificmedicalsupply.com/nellcor-n-395-pulse-oximeter/, Mar. 15, 2017.
Nellcor Oximax N600X, http://www.medtronic.com/content/dam/covidien/library/us/en/product/pulse-oximetry/N600X_OperatorsManual_EN_10055994A001.pdf, Mar. 15, 2017.
Nellcor N85 Monitor with Oximax Technology & Microstream Capnography, http://www.medtronic.com/covidien/products/pulse-oximetry/nellcor-n85-pulse-oximetry-monitor, Mar. 15, 2017.
Philips A04 SPM (Nellcor/Covidien/Medtronic SpO2 Module Compatible with Philip IntelliVue Monitors), http://www.medtronic.com/covidien/products/pulse-oximetry/phillips-a04-spm, Mar. 15, 2017.
Masimo iSpO2 Pulse Oximeter / Masimo iSpO2 RX, http://www.masimo.co.uk/pulseOximeter/iSpO2Rx.htm, Mar. 15, 2017.
Masimo MightSat Fingertip Pulse Oximeter (3 different models), http://masimopersonalhealth.com/products/mightysat/, Mar. 15, 2017.
MightSat RX—MightSat Rx with Bluetooth LE—MightSat RX with Bluetooth LE & PVI, http://masimopersonalhealth.com/products/mightysat/, Mar. 15, 2017.
Masimo Root, http://www.masimo.com/home/root/root-with-noninvasive-blood-pressure-and-temperature-monitoring/, Mar. 15, 2017.
Masimo Radius-7, http://www.masimo.com/home/root/radius7/, Mar. 15, 2017.
Masimo Radical-7, http://www.masimo.com/home/rainbow-pulse-co-oximetry/rainbow-monitors/radical7/, Mar. 15, 2017.
Masimo Rad-87, http://www.masimo.com/home/rainbow-pulse-co-oximetry/rainbow-monitors/rad87/, Mar. 15, 2017.
Masimo Rad-57, http://www.masimo.com/home/rainbow-pulse-co-oximetry/rainbow-monitors/rad-57/, Mar. 15, 2017.
Masimo Pronto, http://www.masimo.com/home/rainbow-pulse-co-oximetry/rainbow-monitors/pronto/, Mar. 15, 2017.
Masimo Rad-5, http://www.masimo.com/home/signal-extraction-pulse-oximetry/masimo-set-monitors/rad5-rad-5v/, Mar. 15, 2017.
Masimo Rad-5v https://www.mooremedical.com/index.cfm?/Rad-5v%AE-Pulse-Oximeter/&PG=CTL&CS=HOM&FN=ProductDetail&PID=32713&spx=1, Mar. 15, 2017.
Masimo Pronto-7, http://www.masimo.com/home/rainbow-pulse-co-oximetry/rainbow-monitors/pronto7/, Mar. 15, 2017.

(56) References Cited

OTHER PUBLICATIONS

Masimo Rad 8, http://www.masimo.com/home/signal-extraction-pulse-oximetry/masimo-set-monitors/rad-8/, Mar. 15, 2017.
Cercacor Ember Noninvasive Hemoglobin Tracker—Ember Sport & Ember Sport Premium, http://www.cercacor.com/ember-models, Mar. 15, 2017.
Nonin Onyx Vantage 9590 Fingertip Pulse Oximeter, http://www.nonin.com/Finger-Pulse-Oximeter/Onyx-Vantage-9590, Mar. 15, 2017.
Nonin GO2 Pulse Oximeter, http://www.nonin.com/Finger-Pulse-Oximeter/Nonin-GO2, Mar. 15, 2017.
Nonin GO2 Achieve Pulse Oximeter, http://www.nonin.com/Finger-Pulse-Oximeter/Nonin-GO2, Mar. 15, 2017.
Nonin GO2 LED Achieve Pulse Oximeter, https://www.amazon.com/Nonin-Achieve-Fingertip-Pulse-Oximeter/dp/B002X7Q4RQ, Mar. 15, 2017.
Nonin Model 3230 (Wireless), http://www.nonin.com/OEMSolutions/Nonin_3230_Bluetooth_SMART, Mar. 15, 2017.
Nonin Model 3231 (USB Cable), http://www.nonin.com/OEMSolutions/Nonin_3231_USB, Mar. 15, 2017.
Nonin Onyx II 9560 Wireless Pulse Oximeter for Medical Professionals, http://www.nonin.com/Onyx9560-OEM, Mar. 15, 2017.
Nonin WristOX2 3150 Wrist-Worn Pulse Oximeter, http://www.nonin.com/OEMSolutions/WristOx23150-OEM, Mar. 15, 2017.
Nonin 8500 Handheld Pulse Oximeter, http://www.nonin.com/Model8500, Mar. 15, 2017.
Nonin 9840 Series Pulse Oximeter and CO2 Detector, http://www.nonin.com/9840Series, Mar. 15, 2017.
Nonin 9843 Non-alarm, https://www.concordhealthsupply.com/Nonin-9843-Handheld-CO2-Meter-p/non-9843.htm?gclid=Cj0KEQjwuZvIBRD-8Z6B2M2Sy68BEiQAtjYS3G_TCc-QpvjchXWbcuo6g_vgGW82QLtPOiZHSM7R5cEaAhV58P8H-AQ, Mar. 15, 2017.
Nonin 9847 Alarm, https://www.concordhealthsupply.com/Nonin-Handheld-CO2-Monitor-p/non-9847.htm?gclid=Cj0KEQjwuZvIBRD-8Z6B2M2Sy68BEiQAtjYS3Blmy7QGBD0wGEpqtlskSz3Diu0GLCxhXIg6QYhZkY8aAsbb8P8HAQ, Mar. 15, 2017.
Nonin PalmSAT 2500 Series, http://www.nonin.com/PalmSAT2500, Mar. 15, 2017.
Nonin 7500 Tabletop Portable Pulse Oximeter, http://www.nonin.com/Model7500, Mar. 15, 2017.
Nonin 7500 FO (Fiberoptic), http://www.nonin.com/Model7500FO, Mar. 15, 2017.
Nonin Avant 9600, http://www.nonin.com/Avant9600, Mar. 15, 2017.
Nonin 2120 Tabletop Pulse Oximeter with Noninvasive Blood Pressure, http://www.nonin.com/Avant2120, Mar. 15, 2017.
Nonin Lifesense Capnography & Pulse Oximeter Monitor, http://www.nonin.com/LifeSense, Mar. 15, 2017.
Nonin SenSmart Model X 100 Universal Oximetry System, http://www.nonin.com/sensmart, Mar. 15, 2017.
Venni VI-100 A Desktop Pulse Oximeter with Built-In Thermal Printer, https://www.foremostequipment.com/venni-vi-100a-desktop-pulse-oximeter-w-built-in-thermal-printer/, Mar. 15, 2017.
Venni VI-300 A 2 ParmenterVital Signs Monitor with Printer, https://www.foremostequipment.com/venni-vi-300a-2-parameter-vital-signs-monitor-w-printer/, Mar. 15, 2017.
Venni VI-200A Vital Sign Monitor, https://www.foremostequipment.com/venni-vi-200a-vital-sign-monitor/, Mar. 15, 2017.
Venni VI 60C Hand Field Color Pulse Oximeter, http://www.medicaldevicedepot.com/Venni-Handheld-Color-Pulse-Oximeter-p/vi-60c.htm, Mar. 15, 2017.
Venni VI-60D Handheld Pulse Oximeter, http://www.medicaldevicedepot.com/Venni-Handheld-Color-Pulse-Oximeter-p/vi-60d.htm, Mar. 15, 2017.
GE/Datex Ohmeda TuffsSAt Handheld Pulse Oximeter, http://pacificmedicalsupply.com/ge-datex-ohmeda-handheld-tuff-sat-pulse-oximeter-small-handheld/, Mar. 15, 2017.
GE Ohmeda TrueSat Pulse Oximeter, https://www.turnermedical.com/GE_TRUSAT_3500_PULSE_OXIMETER_p/ge_trusat.htm, Mar. 15, 2017.
GE Datex Ohmeda Tabletop Pulse Oximeter, https://www.dotmed.com/listing/monitor/datex-ohmeda/3800-pulse-oximeter/1756547?utm_source=base&utm_medium=search&utm_campaign=Base&gclid=Cj0KEQjwuZvIBRD-8Z6B2M2Sy68BEiQAtjYS3FF89fMqM1M2IzifSV_f0h21M9Xv-4UQegrnUr-IZa8aAozv8P8HAQ, Mar. 15, 2017.
GE Carescape Monitor B850, http://www3.gehealthcare.com/en/products/categories/patient_monitoring/patient_monitors/carescape_monitor_b850, Mar. 15, 2017.
GE Carescape Monitor B650, http://www3.gehealthcare.com/en/products/categories/patient_monitoring/patient_monitors/carescape_monitor_b650, Mar. 15, 2017.
GE Carescape Monitor B450, http://www3.gehealthcare.com/en/products/categories/patient_monitoring/patient_monitors/carescape_monitor_b450, Mar. 15, 2017.
GE Carescape VC 150 Vital Signs Monitor, http://www3.gehealthcare.com/en/products/categories/patient_monitoring/patient_monitors/carescape_vc150, Mar. 15, 2017.
GE B40 Patient Monitor, http://www3.gehealthcare.com/en/products/categories/patient_monitoring/patient_monitors/b40_patient_monitor, Mar. 15, 2017.
GE Carescape V100 Monitor, http://www3.gehealthcare.com/en/Products/Categories/Patient_Monitoring/Patient_Monitors/CARESCAPE_V100, Mar. 15, 2017.
Nihon Kohden Oxypal OLV-2700/ Oxypal Neo OLV-3100J/K, http://www.nihonkohden.de/uploads/media/OLV-2700_02.pdf, Mar. 15, 2017.
Nihon Kohden Life Scope G3 GZ 130 P, http://www.medtronic.com/covidien/products/oem-monitoring-solutions/oem-partners/nihon-kohden#row-3, Mar. 15, 2017.
Nihon Kohden Life Scope G9 CSM-1901, http://www.medtronic.com/covidien/products/oem-monitoring-solutions/oem-partners/nihon-kohden#row-3, Mar. 15, 2017.
Nihon Kohden Life Scope TR BSM-6000 Series (BSM-6301/6501/6701), http://www.medtronic.com/covidien/products/oem-monitoring-solutions/oem-partners/nihon-kohden#row-3, Mar. 15, 2017.
Nihon Kohden Life Scope VS BSM-3000 series (BSM-3500/3700), http://www.medtronic.com/covidien/products/oem-monitoring-solutions/oem-partners/nihon-kohden#row-3, Mar. 15, 2017.
Nihon Kohden Life Scope PT BSM-1700 series, http://www.medtronic.com/covidien/products/oem-monitoring-solutions/oem-partners/nihon-kohden#row-3, Mar. 15, 2017.
Nihon Kohden Vismo PVM-2703, http://www.medtronic.com/covidien/products/oem-monitoring-solutions/oem-partners/nihon-kohden#row-3, Mar. 15, 2017.
Nihon Kohden Bedside Monitor PVM-2701, http://www.medtronic.com/covidien/products/oem-monitoring-solutions/oem-partners/nihon-kohden#row-3, Mar. 15, 2017.
Nihon Kohden SVM-7500 series/SVM-7600 series, http://www.mbd-surgical.com/product/Ge_all/Patient_Monitoring/SVM-7600%20Series%20Bedside%20Monitor.pdf, Mar. 15, 2017.
Philips IntelliVue MX40, http://www.usa.philips.com/healthcare/product/HC865350/intellivue-mx40-wearable-patient-monitor, Mar. 15, 2017.
Philips IntelliVue MP40/MP50/MP60/MP70 Patient Monitor, http://www.philips.ie/healthcare/product/HC862116/intellivue-mp40-and-mp50-bedside-patient-monitors, Mar. 15, 2017.
IntelliVue MX400/MX450/MX 500/MX550, http://www.usa.philips.com/healthcare/product/HC866060/intellivue-mx400-patient-monitor, Mar. 15, 2017.
Philips IntelliVue MX600, MX700, http://www.yms.co.za/wp-content/uploads/2015/04/Philips-IntelliView-MX700-Patient-Monitor.pdf, Mar. 15, 2017.
Philips IntelliVue Mx800, Philips IntelliVue Mx800, Mar. 15, 2017.
Philips IntelliVue MP90, http://www.usa.philips.com/healthcare/product/HC862452/intellivue-mp90-bedside-patient-monitor, Mar. 15, 2017.
Philips IntelliVue MP5SC, http://www.usa.philips.com/healthcare/product/HC865322/intellivue-mp5sc-patient-monitor, Mar. 15, 2017.
Philips IntelliVue MMS X2, http://www.usa.philips.com/healthcare/product/HC865039/intellivue-mms-x2-measurement-module-monitor, Mar. 15, 2017.

(56) References Cited

OTHER PUBLICATIONS

Philips IntelliVue MP2, http://www.usa.philips.com/healthcare/product/HC865040/intellivue-mp2-wearable-patient-monitor, Mar. 15, 2017.
Philips IntelliVue MP5, http://www.usa.philips.com/healthcare/product/HC865024/intellivue-mp5-bedside-patient-monitor, Mar. 15, 2017.
Philips SureSigns VM1, http://www.usa.philips.com/healthcare/product/HC863264/suresigns-vm1-vital-signs-monitor, Mar. 15, 2017.
Philips SureSigns VS2+, http://www.usa.philips.com/healthcare/product/HC863278/suresigns-vs2-plus-vital-signs-monitor, Mar. 15, 2017.
Philips SureSigns VSi, http://www.usa.philips.com/healthcare/product/HC863275/suresigns-vsi-vital-signs-monitor, Mar. 15, 2017.
Philips SureSigns VS3, http://www.philips.ie/healthcare/product/HC863069/suresigns-vs3-vital-signs-monitor, Mar. 15, 2017.
Philips SureSigns VS4, http://www.usa.philips.com/healthcare/product/HC863283/suresigns-vs4-vital-signs-monitor, Mar. 15, 2017.
Philips IntelliVue Cableless Measurement NOTCN62, http://www.usa.philips.com/healthcare/product/HCNOCTN62/intellivue-cableless-patient-monitoring, Mar. 15, 2017.
Nellcor Flexible SpO2 Reusable Sensors (FLEXMAX/FLEXMAX-P/FLEXMAX-HC/FLEXMAX-PHC), http://www.medtronic.com/covidien/products/pulse-oximetry/nellcor-flexible-spo2-reusable-sensor, Mar. 15, 2017.
Nellcor Reusable SpO2 Sensors with OxiMax Technology, http://www.medtronic.com/covidien/products/pulse-oximetry/nellcor-reusable-spo2-sensors, Mar. 15, 2017.
Nellcor Disposable Sensor—Forehead SpO2 Sensor and Headband (Reflectance), http://www.medtronic.com/covidien/products/pulse-oximetry/nellcor-spo2-forehead-sensor, Mar. 15, 2017.
Nellcor Adhesive SpO2 Sensors, http://www.medtronic.com/covidien/products/pulse-oximetry/nellcor-spo2-adhesive-sensors, Mar. 15, 2017.
Nellcor Disposable Sensor—Adult/Neonatal SpO2 sensor, http://www.covidien.com/imageServer.aspx/doc229982.pdf?contentID=30898&contenttype=application/pdf, Mar. 15, 2017.
Nellcor Single Patient Use Two Piece Sensors, http://www.medtronic.com/covidien/products/pulse-oximetry/nellcor-two-piece-spo2-sensors, Mar. 15, 2017.
Masimo Reusable Sensors (LNCS DC-I/LNCS DCI-P/LNCS DB-I/LNCS TC-I/LNCS TF-I/LCNS Y-I Multisite Sensor), http://www.masimo.com/horne/signal-extraction-pulse-oximetry/masimo-set-sensors/lncs-reusable-sensors/, Mar. 15, 2017.
Masimo Disposable Sensors (LNCS Adtx/LNCS Adtx-3/LNCS Inf/LNCS Inf-3/LNCS Inf-L/LNCS Neo/LNCS Neo-3/LNCS Neo-L/LNCS NeoPt/LNCS NeoPt-3/LNCS NeoPt-L/LNCS NeoPt-500/LNCS E1/LNCS TFS-1/M-LNCS E1 Sensor/, http://www.masimo.com/home/signal-extraction-pulse-oximetry/masimo-set-sensors/lncs-adhesive-sensors/, Mar. 15, 2017.
Masimo Rainbow ReSposable Sensors (R2-25/R2-20), http://www.masimo.fr/rainbow/rainbow%20Disposable%20and%20ReSposable.htm, Mar. 15, 2017.
Masimo Rainbow Adhesive Sensors (rainbow R1 25/rainbow R1 20/rainbow R1 25L/rainbow R1 20L/rainbow R25/rainbow R20/rainbow R25-L/rainbow R20-L), http://www.masimo.co.uk/rainbow/rainbow%20Disposable%20and%20ReSposable.htm, Mar. 15, 2017.
Masimo Respiratory Acoustic Sensor RAS 125c, http://www.masimo.com/home/rainbow-acoustic-monitoring/ras-sensors/, Mar. 15, 2017.
Masimo Pronto-7 Sensors, http://www.medline.com/product/Pronto-7-Rainbow-Sensors-by-Masimo-Corporation/Z05-PF71138, Mar. 15, 2017.
Masimo LNCS Patient Cables (Red LNC M20/Red LNC/Red 25 LNC/Red 25 LNC RA/LNC/LNC Ext/LNC MP4/LNC MP10/LNC GE/LNC-SL-10/LNC DB9/LNC NK/, http://www.masimo.com/home/signal-extraction-pulse-oximetry/masimo-set-sensors/lncs-patient-cables/ Mar. 15, 2017.
Masimo Adapter Cables (LNCS to RD Adapter Cable/LNCS to PC Adpater Cable/LNC CMS/LNC MAC-GE/LNC MAC-SL/LNC MAC-SL2/LNC MAC-180/LNC MAC-395), http://www.masimo.com/home/signal-extraction-pulse-oximetry/masimo-set-sensors/lncs-patient-cables/, Mar. 15, 2017.
Cercacor Ember Sensor, http://technology.cercacor.com/, Mar. 15, 2017.
Nonin 8000 Series Reusable SpO2 Sensors (8000SS/8000SM/8000SL/8000AP/8000AA/8-Q2 1M/8000R/8000R 1M), http://www.nonin.com/ReusableSensors, Mar. 15, 2017.
Nonin Disposable Sensors (6000C/6000CA/6000CI/6000CN/6000CO/7000A/7000I/7000N/7000P/6500SA/6500MA, http://www.nonin.com/DisposableSensors, Mar. 15, 2017.
Nonin Reusable Flex Sensor and Disposable Wraps, http://www.nonin.com/FlexSensors, Mar. 15, 2017.
Venni Adult Pulse Oximeter Probe for 60C/60D, http://www.susquemicro.com/nav/pages/probe/venni.shtml, Mar. 15, 2017.
Venni Infant/Neonate Pulse Oximeter Probe for 60C/60D, http://www.susquemicro.com/nav/pages/probe/venni.shtml, Mar. 15, 2017.
Venni Pediatric Pulse Oximeter Probe for 60C/60D, http://www.susquemicro.com/nav/pages/probe/venni.shtml, Mar. 15, 2017.
Venni Adult Pulse Oximeter Probe for 200 A, http://www.susquemicro.com/nav/pages/probe/venni.shtml, Mar. 15, 2017.
Venni Pediatric Pulse Oximeter Probe for 200 A, http://www.susquemicro.com/nav/pages/probe/venni.shtml, Mar. 15, 2017.
Venni Extension Cable for 200 A, http://www.susquemicro.com/nav/pages/probe/venni.shtml, Mar. 15, 2017.
Venni Adult Pulse Oximeter Probe for 3510, http://www.susquemicro.com/nav/pages/probe/venni.shtml, Mar. 15, 2017.
Venni Pediatric Pulse Oximeter Probe for 3510, http://www.susquemicro.com/nav/pages/probe/venni.shtml, Mar. 15, 2017.
GE Datex Ohmeda Sensor, http://pacificmedicalsupply.com/ge-datex-ohmeda-oxytip-3-ft-hard-shell-soft-multi-site-pediatric-infant-or-ear-clip-spo2-sensor/, Mar. 15, 2017.
GE TruSignal Connector, https://www.partsfinder.com/parts/ge-healthcare/TSG3, Mar. 15, 2017.
GE TruSAT Connector, https://www.mspinc.com/tru-signal-interconnect-cable-trusat-connector, Mar. 15, 2017.
Ohmeda Connector, https://www.google.com/url?sa=t&rct=j&q=&esrc=s&source=web&cd=1&cad=rja&uact=8&ved=0ahUKEwj0jeXDy8_TAhUhxVQKHQffDI0QFghIMAA&url=http%3A%2F%2Fwww3.gehealthcare.nl%2F~%2Fmedia%2Fdownloads%2Fuk%2Fproduct%2Fclinical%2520consumables%2Ftrusignal_spu_sensors%2Ftrusignal%2520spo2%2520spec%2520sheet_doc1403853.pdf%3FParent%3D%257B9F2E8F8D-66B0-4017-9CF1-4328EA62F108%257D&usg=AFQjCNEf7_bYyoOeDJ_CiWA5R4JK7tj53Q&sig2=GbSA85o10z-MowEfcdA8EQ, Mar. 15, 2017.
Datex Connector, https://www.google.com/url?sa=t&rct=j&q=&esrc=s&source=web&cd=1&cad=rja&uact=8&ved=0ahUKEwj0jeXDy8_TAhUhxVQKHQffDI0QFghIMAA&url=http%3A%2F%2Fwww3.gehealthcare.nl%2F~%2Fmedia%2Fdownloads%2Fuk%2Fproduct%2Fclinical%2520consumables%2Ftrusignal_spu_sensors%2Ftrusignal%2520spo2%2520spec%2520sheet_doc1403853.pdf%3FParent%3D%257B9F2E8F8D-66B0-4017-9CF1-4328EA62F108%257D&usg=AFQjCNEf7_bYyoOeDJ_CiWA5R4JK7tj53Q&sig2=GbSA85o10z-MowEfcdA8EQ, Mar. 15, 2017.
Philips Sensors (M1131A/M1132A/M1133A/M1134A), http://www.pacificwestmedical.com/philips-healthcare/philips-medical-supplies/sp02-sensors/philips-m1131a-philips-disposable-adult-ped-spo2-sensors-20-box/, Mar. 15, 2017.
Smiths Medical BCI Sensors, https://www.smiths-medical.com/products/patient-monitoring/patient-monitoring-accessories/oximeter-accessories/disposable-sensors, Mar. 15, 2017.
Solaris Pulse Oximetry Sensors, http://www.solarismedtech.com/spo2.ntml, Mar. 15, 2017.
Edan Pulse Oximeter Sensors, https://mfimedical.com/products/edan-reusable-spo2-sensor?utm_source=google&utm_medium=cse&utm_term=199923581474&gclid=Cj0KEQjwuZvIBRD-8Z6B2M2Sy68BEiQAtjYS3CHMt-uuV97yCJozA0KK-dMkg8KU4JPAtNVCeI5_bz3oaAshu8P8HAQ, Mar. 15, 2017.
Edan Adult Reusable Sensor, https://mfimedical.com/products/edan-reusable-spo2-sensor?utm_source=google&utm_medium=cse&utm_term=19992358147&gclid=Cj0KEQjwuZvIBRD-8Z6B2M2Sy6-

(56) References Cited

OTHER PUBLICATIONS

8BEiQAtjYS3CHMt-uuV97yCjozA0KKdMkq8KU4JPAtNVCeI5_bz3oaAshu8P8HAQ, Mar. 15, 2017.
Edan Pediatric Silicon Soft Tip, https://mfimedical.com/products/edan-reusable-spo2-sensor?utm_source=google&utm_medium=cse&utm_term=19992358147&gclid=Cj0KEQjwuZvIBRD-8Z6B2M2Sy68BEiQAtjYS3CHMt-uuV97yCjozA0KKdMkq8KU4JPAtNVCeI5_bz3oaAshu8P8HAQ, Mar. 15, 2017.
Nihon Kohden Sensors Blue Pro SpO2 Sensors, http://www.nihonkohden.de/products/patient-monitoring/single-parameter-monitors/pulse-oximetry/blupro.html?L=1, Mar. 15, 2017.
William, New, Jr., Continuous Non-Invasive Measurement of Arterial Oxygen, Journal of the Japanese Society of Clinical Anesthesia, vol. 6, No. 6, Dec. 1986.
Extended European Search Report for European Patent Application No. 16874009.0, dated Apr. 2, 2019, 9 pages.
Notice of Allowance for U.S. Appl. No. 16/274,207, dated Oct. 3, 2019, 10 pages.
International Search Report and Written Opinion for PCT International Application No. PCT/US16/66016, dated May 18, 2017, 13 pages.
International Preliminary Report on Patentability for PCT International Application No. PCT/US16/66016, dated Jun. 12, 2018, 9 pages.
U.S. Appl. No. 16/274,207, Notice of Allowance (and 892) dated Jan. 13, 2020, 9 pages.
U.S. Appl. No. 15/372,341, Notice of Allowance dated Nov. 7, 2019, 6 pages.
PCT International Search Report and Written Opinion in International Application PCT/US2019/048189, dated Dec. 6, 2019, 17 pages.

\* cited by examiner

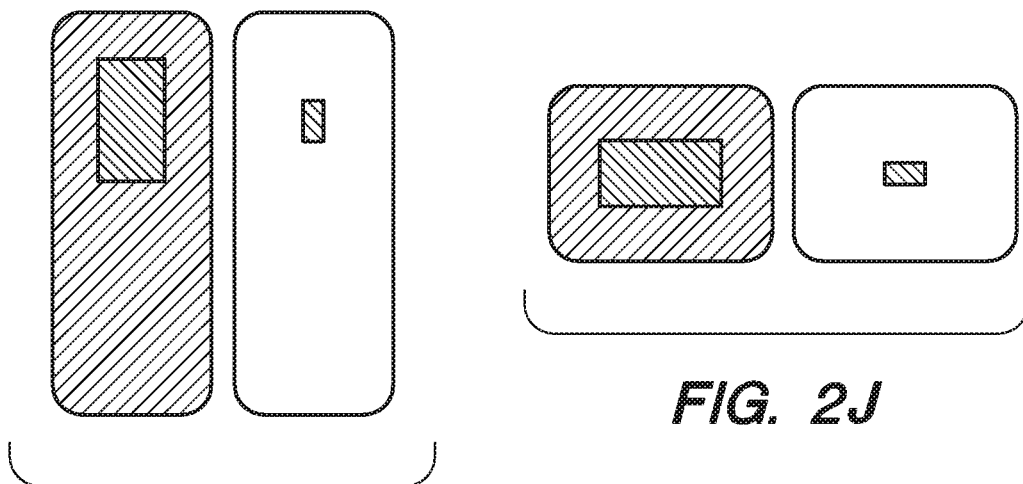
FIG. 2I
FIG. 2J
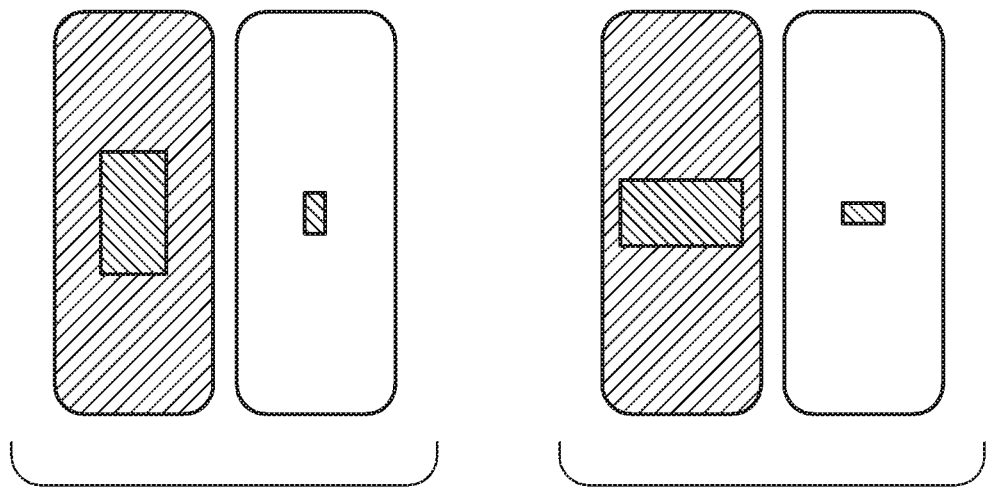
FIG. 2K
FIG. 2L

First (top) layer, top view

Fourth (bottom) layer, bottom view

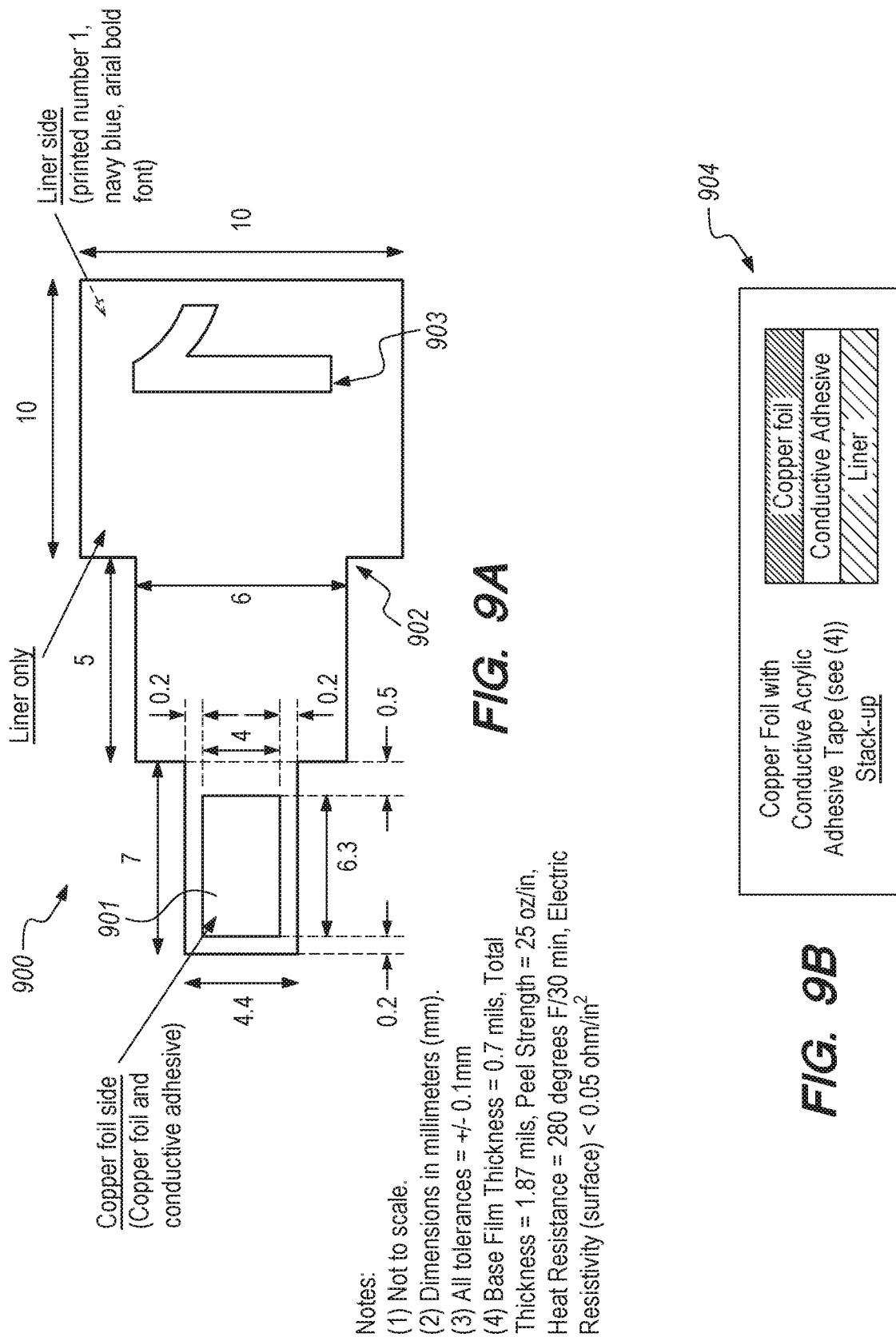

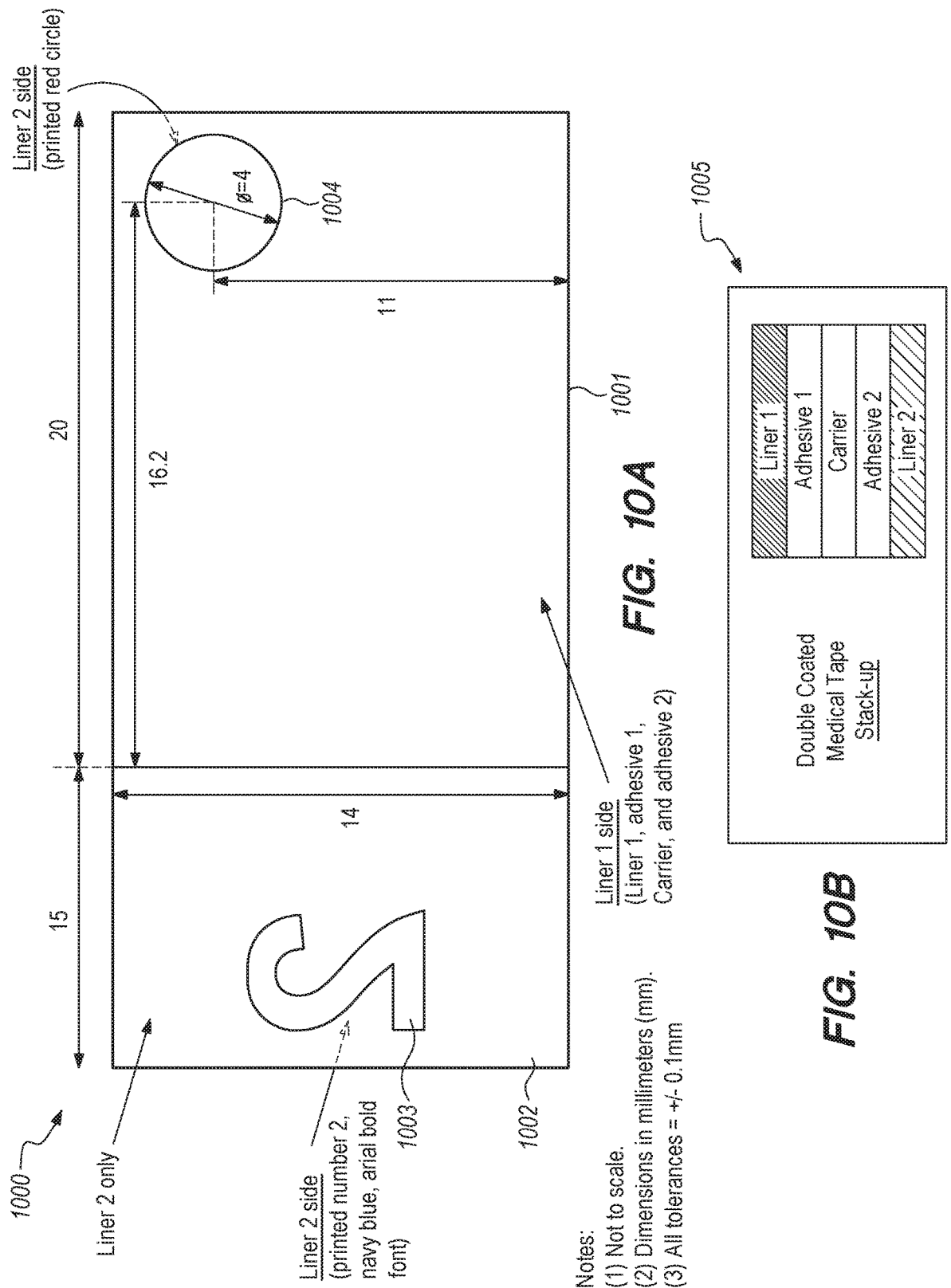

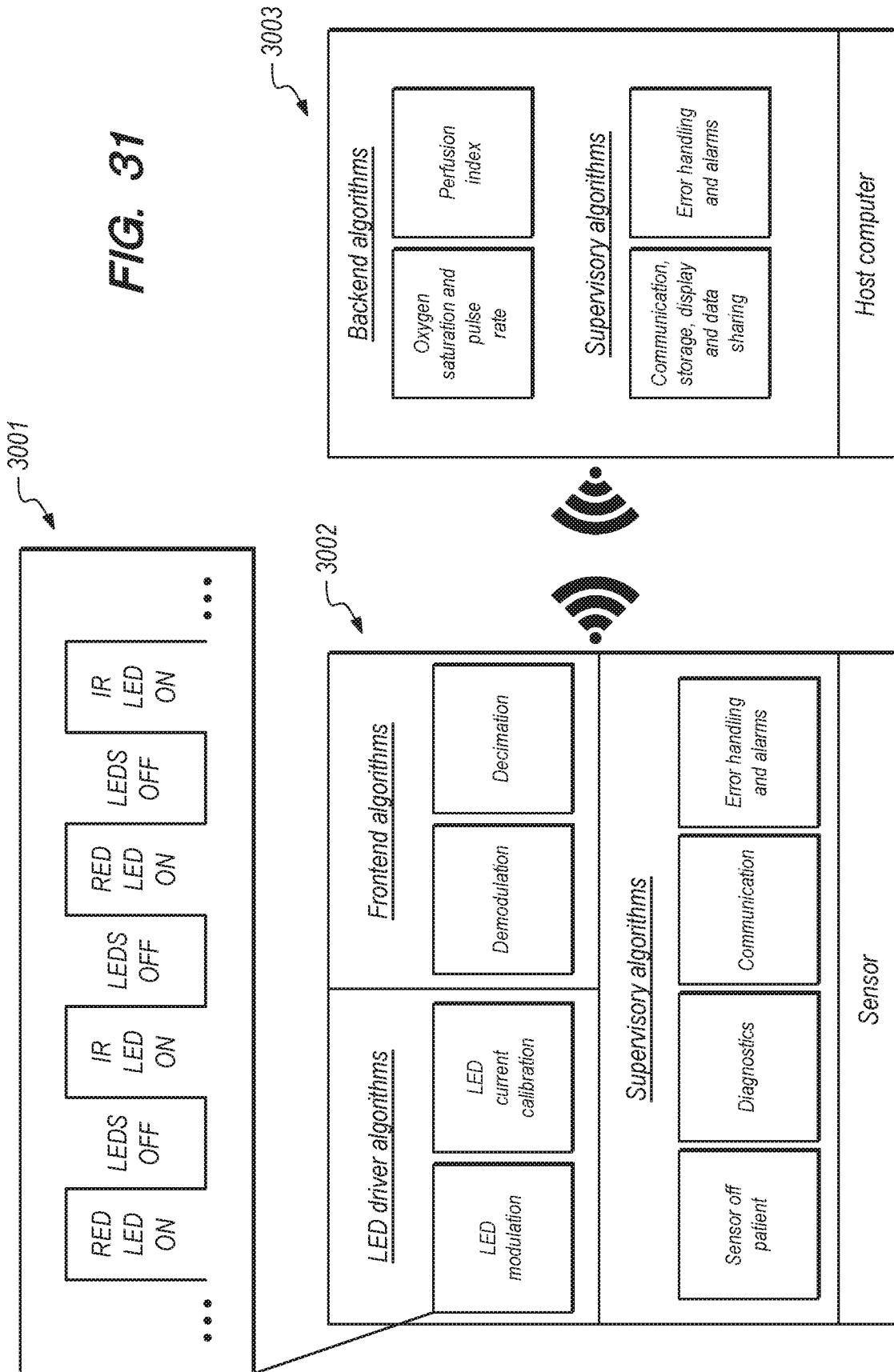

| Action 1 | | Action 2 | | Action 3 | | Net effect |
|---|---|---|---|---|---|---|
| Decreasing emitter-detector optical separation | + | Making the emitter-detector gap region optically dark | + | Applying slight pressure to sensor by means of adhesive bandage | = | Lowers required LED power, maintains optical probing depth, makes light piping likelihood acceptable, and increases photoplethysmograph amplitude |
| Decreases required LED optical power ☑ | + | Increases the required LED power ☒ | + | Decreases required LED optical power ☑ | = | Decreases required LED optical power ☑ |
| Increases likelihood of light piping ☒ | + | Reduces the likelihood of light piping ☑ | + | Reduces the likelihood of light piping ☑ | = | Reduces the likelihood of light piping ☑ |
| Reduces optical probing depth ☒ | + | No detectable reduction or increase in optical probing depth ☑ | + | Increases optical probing depth ☑ | = | Maintains optical probing depth ☑ |
| Reduces photoplethysmograph amplitude ☒ | + | Increases photoplethysmograph amplitude ☑ | + | Increase photoplethysmograph amplitude ☑ | = | Increase photoplethysmograph amplitude ☑ |

Tradeoffs

FIG. 32

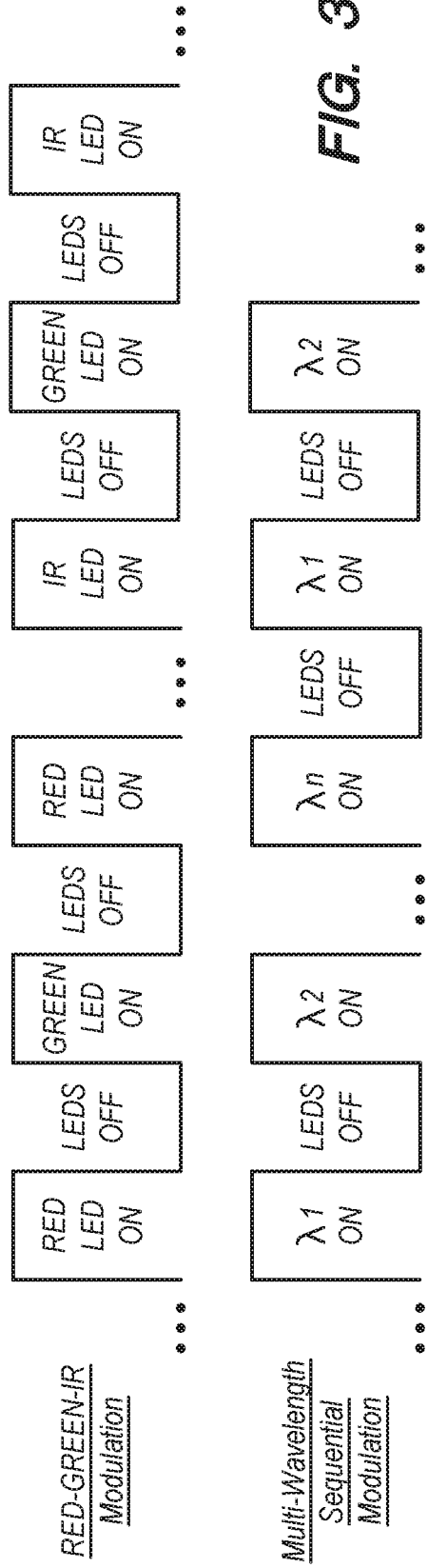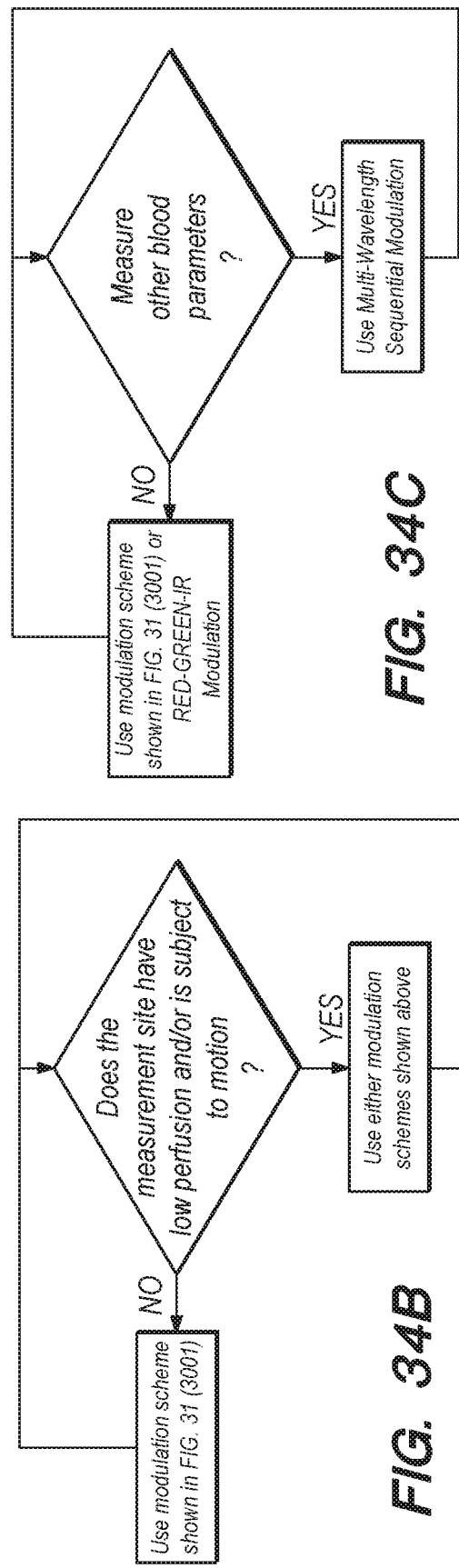
FIG. 34A
FIG. 34B
FIG. 34C

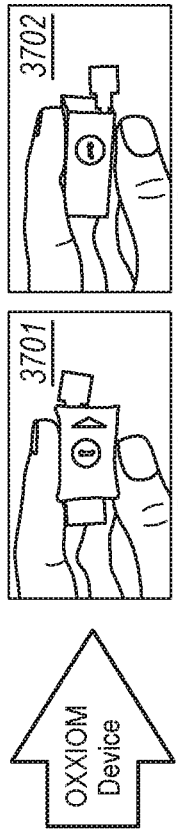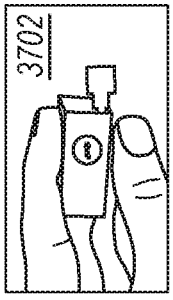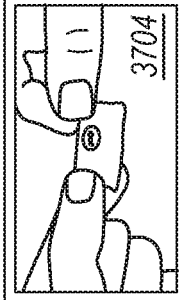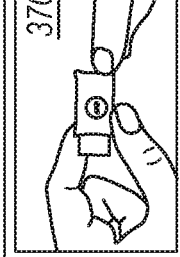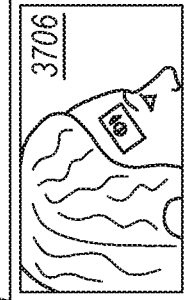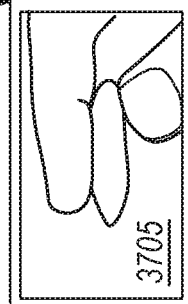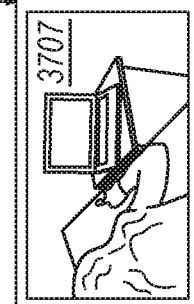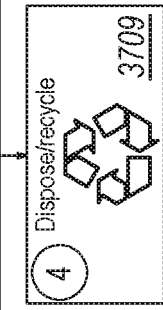
FIG. 37

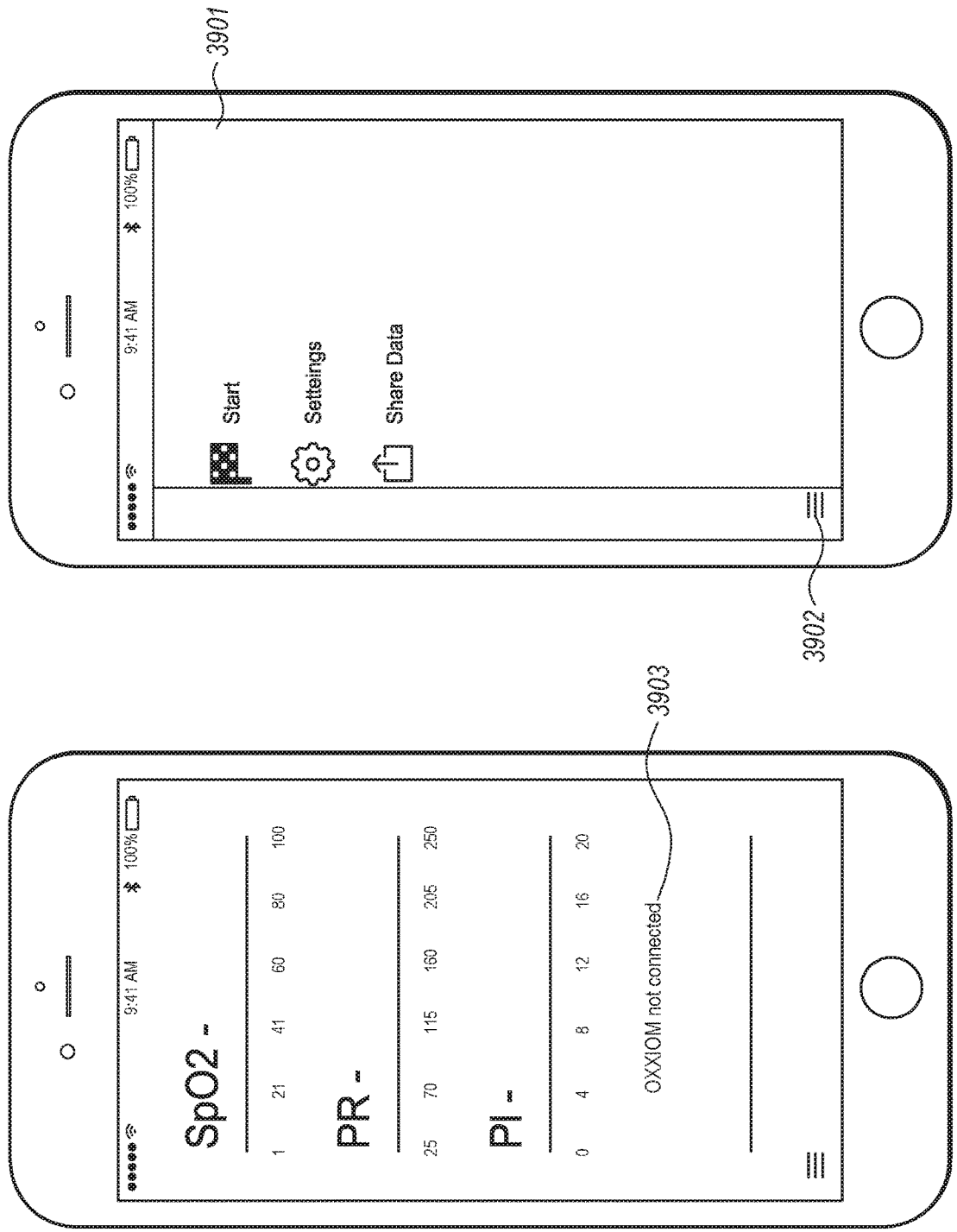

FIG. 45

| Date/Time | Oxxiom Barcode | ID # | Gender | DOB | SpO2 (%) | PR (BPM) | PI (%) |
|---|---|---|---|---|---|---|---|
| 11/17/16 15:59 | F5AA-EB78 | AB345-8932 | M | 1968-05-28 | 97 | 61 | 0.13 |
| 11/17/16 15:59 | F5AA-EB78 | AB345-8933 | M | 1968-05-28 | 97 | 61 | 0.16 |
| 11/17/16 15:59 | F5AA-EB78 | AB345-8934 | M | 1968-05-28 | 97 | 60 | 0.18 |
| 11/17/16 15:59 | F5AA-EB78 | AB345-8935 | M | 1968-05-28 | 97 | 60 | 0.19 |
| 11/17/16 15:59 | F5AA-EB78 | AB345-8936 | M | 1968-05-28 | 97 | 61 | 0.18 |
| 11/17/16 15:59 | F5AA-EB78 | AB345-8937 | M | 1968-05-28 | 96 | 62 | 0.18 |
| 11/17/16 15:59 | F5AA-EB78 | AB345-8938 | M | 1968-05-28 | 96 | 63 | 0.17 |
| 11/17/16 15:59 | F5AA-EB78 | AB345-8939 | M | 1968-05-28 | 96 | 64 | 0.17 |
| 11/17/16 15:59 | F5AA-EB78 | AB345-8940 | M | 1968-05-28 | 96 | 65 | 0.16 |
| 11/17/16 15:59 | F5AA-EB78 | AB345-8941 | M | 1968-05-28 | 97 | 65 | 0.12 |

Sleep Study Oximetry Report

Date: 12-16-2016  Age: 48
ID #: AB345-8934  Gender: Female
Oxxiom Barcode: F5AA-EB78  DOB: 05-28-1968
Total recording time: 450 min

| SpO2 | PR | PI |
|---|---|---|
| Average (%)..............87 | Average (BPM).........75 | Average (%).............2 |
| Median (%)................90 | Median (BPM)..........80 | Median (%)..............3.1 |
| Std (%).......................13 | Std (BPM).................25 | Std (%).....................0.7 |
| Max (%)....................100 | Max (BPM)...............125 | Max (%)....................5.3 |
| Min (%).......................70 | Min (BPM)................55 | Min (%).....................0.1 |
| < 90%......................60% | > Median + 1Std.......40% | > Median + 2Std......20% |
| < 80%......................35% | < Median - 1Std........45% | < Median - 2Std.......40% |
| < 70%........................5% | >Median + 2Std........10% | > Median + 4Std........0% |
| #Desaturations*.........40 | < Median - 2Std........0% | < Median - 4Std.......27% |
| Max desat (%)...........37 | | |
| Max desat dur (sec)...80 | | |

(*) Based on 4% or greater drop from SpO2 baseline.

*FIG. 46*

WIRELESS, DISPOSABLE, EXTENDED USE PULSE OXIMETER APPARATUS AND METHODS

CROSS REFERENCE TO RELATED APPLICATION

The present application is related to and claims the benefit of U.S. Provisional Application Ser. No. 62/264,233, filed Dec. 7, 2015, the contents of which are incorporated herein in their entirety.

FIELD OF THE INVENTION

The present inventions relate generally to the field of pulse oximetry, and more specifically to wireless, disposable, extended time period, continuous pulse oximeter sensor assemblies and related methods and apparatus.

BACKGROUND

Pulse oximetry is a technology that enables the noninvasive monitoring of a patient's arterial blood oxygen saturation and other parameters. The technology was first developed in the 1970s and has been successfully implemented in clinical settings as well as fitness and wellness applications.

In typical prior art pulse oximetry technology, oxygen saturation is measured by means of an optical probe (sensor). The sensor typically includes two light-emitting diodes (LEDs) in the visible (red) and near-infrared regions, and a silicon detector (photodiode) that detects the light emitted by those diodes after it has passed through some part of a patient's body. Typically, the sensor is attached to a blood perfused measurement site (the patient's digit, ear lobe, forehead, etc.), in a reflective or transmissive configuration, to create diffusive light paths through that measurement site. The diffusive light paths typically start at the LEDs and end at the photodiode. Because blood absorbs and scatters light at different rates depending on the applied light wavelength and the blood's oxygen saturation, the red and the near-infrared light wavelengths produced by the LEDs are attenuated at different rates by the site's optical paths (through the patient's body) before reaching the photo diode.

The pulsing of the patient's heart affects measurements with these sensors. For example, the heart's activity during its normal cardiac cycle produces a pulsatile arterial blood flow (plethysmograph) at the measurement site, and that pulsing modulates the light absorbed and scattered by the sensor throughout the site's optical paths. As a result, the red and near-infrared light signals reaching the photodiode also have a "pulsing" pattern, or a pulsatile component (photoplethysmograph), due to the heart/cardiac cycle. Measuring the red and the near-infrared photoplethysmographs over a series of cardiac cycles enables the sensor to noninvasively measure the patient's arterial blood oxygen saturation. This is because the oxygenated blood has higher optical absorption in the near-infrared wavelengths, while the deoxygenated blood has higher optical absorption at the red wavelengths. This property makes it easy to measure the ratio between oxygenated blood and deoxygenated blood (oxygen saturation).

As a consequence, the photoplethysmographs measured by the sensors also typically have fundamental periodicity identical to the heart rate and, therefore, can also be used to measure the patient's heart frequency (pulse rate). The photoplethysmograph intensities are a function of the measurement site's blood perfusion and, typically, the photoplethysmograph associated with the near-infrared wavelength is employed to estimate the site's blood perfusion. The near-infrared wavelength is chosen because it varies less with changes in oxygen saturation, given that the optical properties of oxygenated and deoxygenated blood are less discrepant at the near infrared region. Prior art pulse oximeters typically measure arterial oxygen saturation (SpO2), pulse rate (PR) and the site's blood perfusion (PI).

For clinical or otherwise "critical" applications, acceptable pulse oximeter measurement systems typically require complex electronics and signal processing, which typically requires relatively higher manufacturing costs and power consumption at some point in those systems. This economic and physical reality has a number of implications for the sensors used in such systems and technology.

Prior art pulse oximeters typically use optical sensors that are either reusable or disposable, either wired or wireless, and either "continuous" or "spot-check", depending on the particular application for which and situation in which the sensor is to be used and other factors. Some prior publications purport to disclose various combinations of those features, but for economic and other reasons, those apparently are not economically feasible, for the market today commonly uses only either (a) wired disposable sensors or (b) wireless reusable sensors. Because of power consumption issues (such as those discussed herein), the wireless sensors typically are only used for "spot-check" applications.

In passing, as discussed herein, "continuous" measurement of a parameter describes a sequence of measurements by a sensor, with sampling that is frequent enough to reliably capture all important parameter trend information of interest. In other words, "continuous" does not mean "absolutely without interruption." "Spot-check" describes when the oximeter measurements are for a generally short period of time, such as during a yearly physical or checkup at a doctor's office.

Each of the two main approaches mentioned above (wired disposable sensors or wireless reusable sensors) involves tradeoffs in costs, functionality, size, comfort, and other factors. For example, although prior art wireless sensors allow a user and/or doctor greater freedom of movement (because there are no wires to get tangled with other things, especially if the patient moves around while wearing the sensor), the power and functionality required to gather and transmit the sensor signals in prior art systems requires the wireless sensor to be relatively large and expensive. The power requirements for "continuous" sensing are also substantial in prior art systems, so typical prior art wireless sensors are only useful for "spot checking" oximeter measurements—the sensors must not only be cleaned between uses but also must be recharged or have their batteries replaced. In other words, the wireless reusable sensors have larger form factor and power consumption requirements, which make them not suitable for continuous use.

Disposable sensors have benefits such as helping reduce the need for cleaning the sensors between uses, but as noted above, because disposable sensors typically are thrown away after a single use, prior art disposable sensors typically are manufactured with relatively little onboard power or processing capability (so as to be less expensive). To achieve those goals, they typically are "wired" to some accompanying host device (because the sensor itself does not include the expensive power supply and complex electronics and required signal processing technology and power capabilities required for wireless sensors). Instead, the required complex electronics and signal processing are typically "offloaded" from the disposable sensors through the wires, to a nearby computer, monitor, or other host device, so that the "work" done by the sensor itself is relatively small. By using wired sensors, the electronics and signal processing can (to at least some degree) be accomplished on that "remote" machine rather than by the sensor assembly itself, and the "disposal" of the sensor does not involve throwing away something of greater cost.

These and other factors have prevented the implementation of a disposable wireless sensor product that can be used for an extended period of time and thus provide a "continuous" set of oximeter data for a patient with the convenience and other benefits of a wireless sensor, while still meeting the quality requirements for clinical and other critical data collection and monitoring.

Others have attempted hybrid systems such as the one in US 2014/0200420 A1, which uses a conventional disposable sensor (the lower cost component) wired to a sensor interface box (the higher cost component) wrapped around the subject's wrist that sends waveforms and or measurements wirelessly to a monitor so that measurements derived by the monitor are generally equivalent to measurements derived by the sensor. For the same reasons aforementioned, and because of the additional sensor wires and connectors required, such topologies have in general a relatively larger footprint, with excessive weight and required body area, making them not practical for continuous monitoring where the patient's comfort is a concern. In addition, the sensor interface box and cables are reusable and thus increase the risk of patient cross-contamination.

For applications that require continuous monitoring, the disposable sensor is preferred for a number of reasons, including:
(i) Lighter and smaller size. The plastic enclosure and mechanical components in reusable sensors typically must be somewhat more rugged to withstand multiple uses. For disposable versions, those components typically are replaced with single-use adhesive tapes.
(ii) More consistent sensor placement and compliance over time, given that the disposable sensor typically is adhered to the patient's measurement site and is less likely to shift from that location.
(iii) Less risk of contamination, given that the sensor is used in a single patient before being disposed.
(iv) Performs better during the patient's physical activity (motion), given that sensor is relatively firmly attached to the patient and the relative motion between sensor and patient's measurement site is minimized.

As mentioned above, in prior art systems the disposable sensors typically are hard-wired to the monitor by means of a reusable patient cable, to reduce sensor costs and increase reliability. Reusable cables between the sensor and monitor provide other benefits, such as enabling the connection of several disposable sensor models into a single monitor model by simply interchanging connection cables. Prior art connection cables commonly offer and/or use different types of hardware connections and also can be used to configure the behavior of a monitor for a particular sensor application.

Prior art disposable sensor technologies continue to have some risks and limitations, including (by way of example and not by way of limitation):
(i) The prior art connection cables used with the disposable sensors are relatively expensive, and therefore typically are reused. This typically requires that the cables be sterilized before they can be reused, especially in surgery rooms and areas where the risk of infections and contaminations are a concern.
(ii) In a hospital environment (and perhaps most environments), typically it is desirable to simplify the workflow. In that regard, management and sterilization of reusable patient cables adds complications and extra actions and measures to the workflow (rather than simplifying workflow). This in turn increases operating costs and can make the hospital staff and clinicians more prone to errors, including ones that may have a catastrophic effect on patients' safety, recovery, and prognosis.
(iii) The patient's mobility is reduced by use of the cables (since the disposable sensor typically is attached to a monitor by means of a patient cable).
(iv) For applications (such as sleep monitoring) where the subject's comfort is a very important aspect of the procedure outcome, using a cable (typically attached to the disposable sensor) limits the patient's mobility (while at sleep), causing discomfort and potential changes in the subject's sleeping patterns, and thus interfering with the accuracy and/or the monitoring itself.
(v) In the monitoring of patients with highly contagious diseases (such as Ebola, SARS, etc.), the need for a patient cable and monitor nearby the patient increases the chances of cross contamination.

Other factors affect and/or result in the foregoing and other limitations of prior art disposable sensor technology. As indicated above, clinical grade pulse oximeter system typically requires advanced instrumentation electronics combined with powerful digital signal processors (DSPs) in order to measure SpO2, PR and PI (especially under extreme cases, such as where blood perfusion is low and/or motion and/or physical activity is present or accentuated). In addition, ambient light interferences (such as those caused by exposure of the sensor photodiode to natural light and/or light sources connected to the electric grid) must be filtered out before reliable measurements may be taken. These and/or other requirements can make it difficult to miniaturize the sensor and monitoring technologies, leading to solutions that are relatively more expensive and have higher power consumption, dimensions, and weight.

To minimize customers' recurrent costs, medical device companies typically divide prior art clinical-grade pulse oximeter systems into three main components: (i) a low-cost disposable sensor, (ii) a reusable patient/connection cable, and (iii) a reusable monitor. In such systems, healthcare providers (hospital, clinics, etc.) typically will (a) purchase and reuse the expensive components (the patient cable and monitor) and (b) purchase and throw away after one use the less expensive components (the disposable sensors). The healthcare providers thus must make recurrent purchases of disposable sensors, to be used on new patients and even for subsequent/repeated tests on a single patient. However, this marketing approach has resulted in a relative low volume of sales of monitors and patient/connection cables (when compared to sales of devices in the consumer electronics market, for instance). Combined with the manufacturers' sometimes high operating and development costs in the clinical-grade patient monitoring market segment, the sale prices of those patient cables and monitors can become unaffordable to many or even most healthcare providers. In order to reduce capital expenditure by the healthcare providers and increase sales, medical device companies typically have decided to offer binding contracts for these prior art systems, which enable healthcare providers to obtain monitors and patient cables at a reduced (perhaps loss-leading) price provided that the healthcare providers commit to purchasing the disposable sensors components for a certain period of time (for the entire organization and/or for individual departments (i.e., pediatrics, anesthesia, etc.)). As part of such contracts, the medical device companies also commonly provide training and technical support for the systems. This contractual arrangement typically is referred to in the industry as a full-house conversion.

Even though such disposable sensor supply contract arrangements may be attractive at first (given the relative low initial investment required), the contracts can become expensive over time. In addition to the typical exclusivity clauses in the supply contracts, and even after those periods of exclusivity have expired, the typical hard-wired connections between the sensors and the cable/monitor components allow medical device manufacturers to create physical mechanisms that prevent the healthcare providers from using any competitors' disposable sensors on the manufacturer's proprietary monitors/cables. The proprietary physical cable/monitor/sensor connections can also increase the costs and efforts and risks to healthcare providers if they try to change to a competitors' technology, because they (among other things) have to retrain personnel and change workflow to switch to a new monitoring solution. This puts healthcare providers in a position of very little control over, and relatively few good/flexible/economic options for their patient monitoring needs. It results in relatively higher costs to the healthcare providers and eventually to patients and our healthcare system generally.

Examples of wireless oximeters in the form of a wireless monitoring device which may be connected to a disposable adhesive sensor via a cable connection, are disclosed in U.S. Pat. No. 7,387,607. Other examples of wireless, disposable oximeters are disclosed in U.S. Pat. Nos. 7,486,977, 7,499,739, 8,457,704, and 8,903,467. In these prior art devices, a bandage comprising a single-use, disposable pulse oximeter is self-powered and transmits information wirelessly. In these prior art reflective oximeters, the light emitter and sensor are separated with a foam material. Such foam material may accentuate light piping between the emitter and sensor, and thereby artificially reduce the photoplethysmograph amplitude and accentuate measurement errors due to the position and pressure applied to the measurement site by the adhesive tape. Further, the required larger emitter-detector separation of these prior art oximeters would cause an exponential attenuation of light (not taught in the accompanying disclosures) due to the current and power levels required by both reflective or transmissive oximeters in order to create measurable signals at the sensor/detector with reasonable signal-to-noise ratios. In addition, the small emitter-detector separation necessitated by the required power consumption would create a very shallow penetration depth of the red and near-infrared wavelengths, thus preventing the probing of layers at the measurement site where the pulsatile capillary blood flow modulates the light signals in order to create the photoplethysmographs used to estimate oxygen saturation, pulse rate, perfusion, and their derivative measurements.

The above-mentioned power consumption required to perform both high quality demodulation of optical signals (in order to prevent ambient light interferences) and further estimation of interesting parameters is not accounted for in the disclosed architectures of these prior art wireless oximeters and their host devices. To be feasible, a distributed architecture is necessary where several complex high-latency tasks with floating-point operations are executed by the host device(s). The disclosed prior art oximeters do not include fixed-point low-power and/or low-cost processors that are required for pulse oximeter algorithms of medical grade instrumentation in sensor patches for extended use.

Other prior art oximeters are disclosed in U.S. Pat. No. 8,761,852, which discloses an adhesive, disposable device which transmits data wirelessly and includes a sensor module, a pliable membrane, and a communication module. In this prior art oximeter, optical sensors are connected to a patient by means of a pliable membrane attached to a wristband. U.S. Pat. No. 8,214,007 discloses a patient monitoring device with a plurality of electrical connections to the body of a patient for monitoring the body's electrical activity. This prior art monitoring device suffers from much of the same limitations as the above-mentioned disclosures. Among other things, the emitter-detector separation is not addressed relative to light piping and pressure, and the signal processing and power consumption requirements.

SUMMARY

In a preferred embodiment, the present inventions provide a wireless, disposable pulse oximeter sensor apparatus and methods capable of providing real-time, continuous, extended time period measurement readings of a user's SpO2, PR and PI. Preferably, the wireless, disposable pulse oximeter sensor provides several benefits over conventional, wired prior art pulse oximeters (whether disposable or not disposable), including, by way of example and not by way of limitation, having a small footprint, requiring low power consumption, having low manufacturing costs, and being monitor-agnostic. In preferred embodiments, these advantages are achieved in a low-power, compact pulse oximeter having compact instrumentation electronics, advanced signal processing and estimation algorithms, low-energy wireless communication protocols, and distributed computing.

BRIEF DESCRIPTION OF THE DRAWINGS

The present inventions will become apparent from the textual description considered in connection with the accompanying drawings. It should be understood, however, that the drawings are intended for the purpose of illustration and not as limits of the inventions. In other words, the present inventions are illustrated by way of example, and not by way of limitation, in the text and the figures of the accompanying drawings. In those drawings, like reference numerals generally refer to similar elements. Persons of ordinary skill in the art will understand, however, that at times, different numbers refer to elements that may have similar or even identical or interchangeable characteristics and functions (e.g., optical sensor 110 in FIG. 1, and optical sensor 403 in FIG. 4).

FIGS. 2H-L illustrate some of the many more alternative additional adhesive tape layouts with adhesion areas suitable for different applications and measurement sites for practicing the inventions.

FIGS. 8A-B, 9A-B, and 10A-B show one of the many alternative ways in which the inventions can be packaged and delivered to a user, including a 3-part adhesive tape design, in accordance with an embodiment of the inventions. For the embodiment illustrated, the encapsulation tape design is shown in FIG. 8A and the corresponding tape stack-up in FIG. 8B; the tape design that enables the circuit board to be turned on by the clinician or user at the time of use is detailed in FIG. 9A and its corresponding tape stack-up in FIG. 9B; the tape design that enables skin-to-device adhesion is shown in FIG. 10A, and its stack up in FIG. 10B, respectively. Persons of ordinary skill in the art will understand that the dimensions and shapes shown in these and other drawings are not intended to be delimiting of the many different embodiments in which the inventions can be practiced. Instead, the dimensions and shapes are only intended to be illustrative of one of the many ways in which the inventions may be practiced.

of a disposable, wireless continuous pulse oximeter sensor, in accordance with an embodiment of the inventions.

Figure 28A:
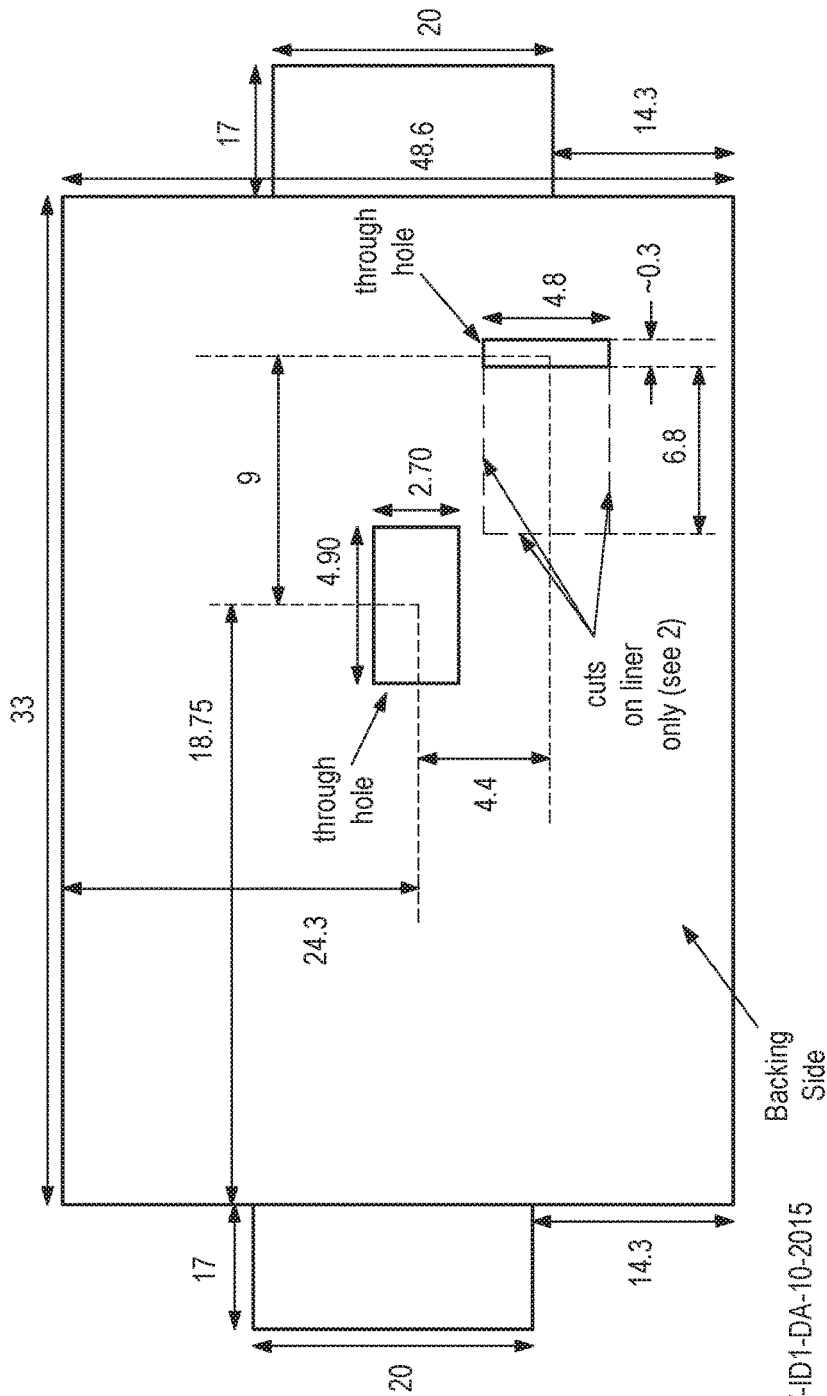
Figure 28B:
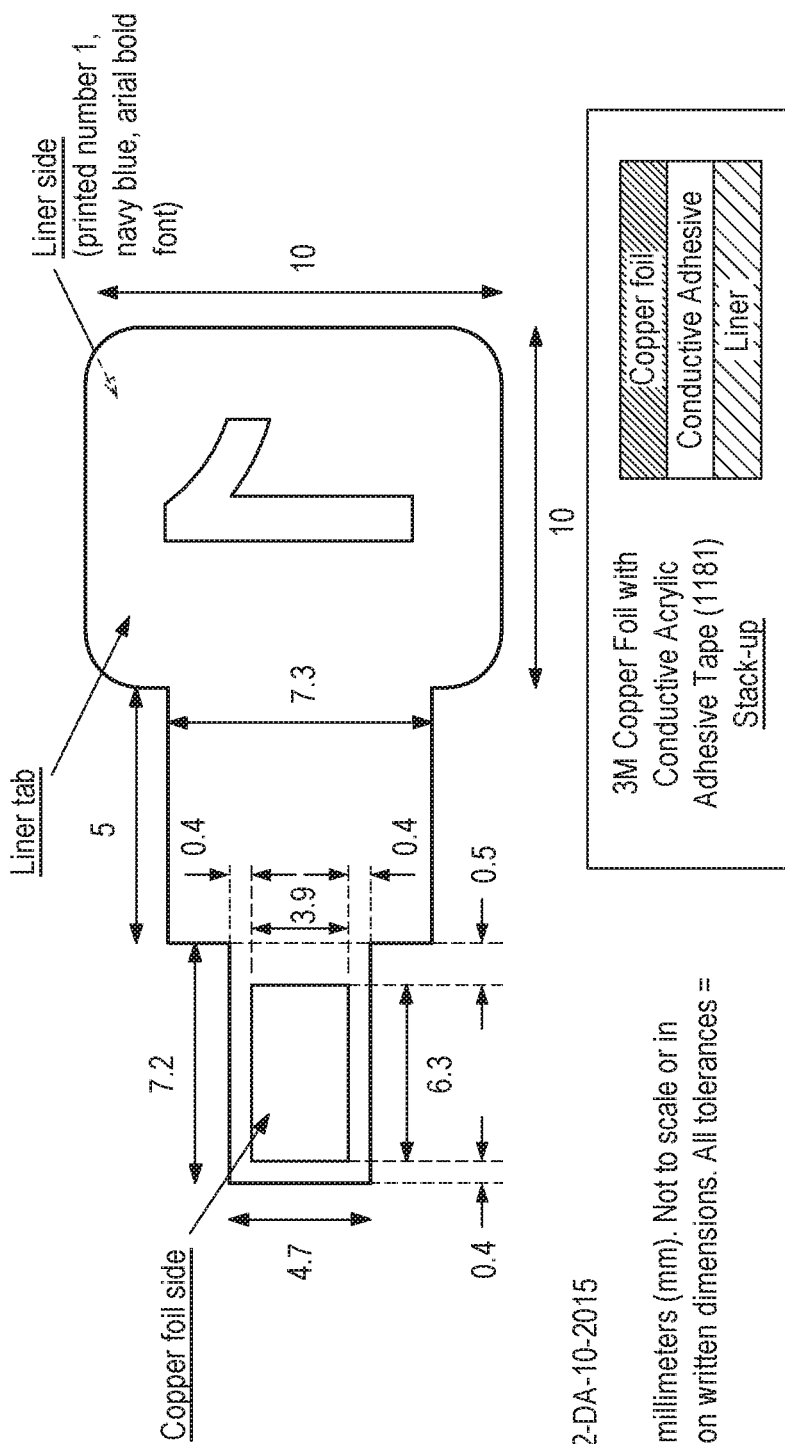
Figure 28C:
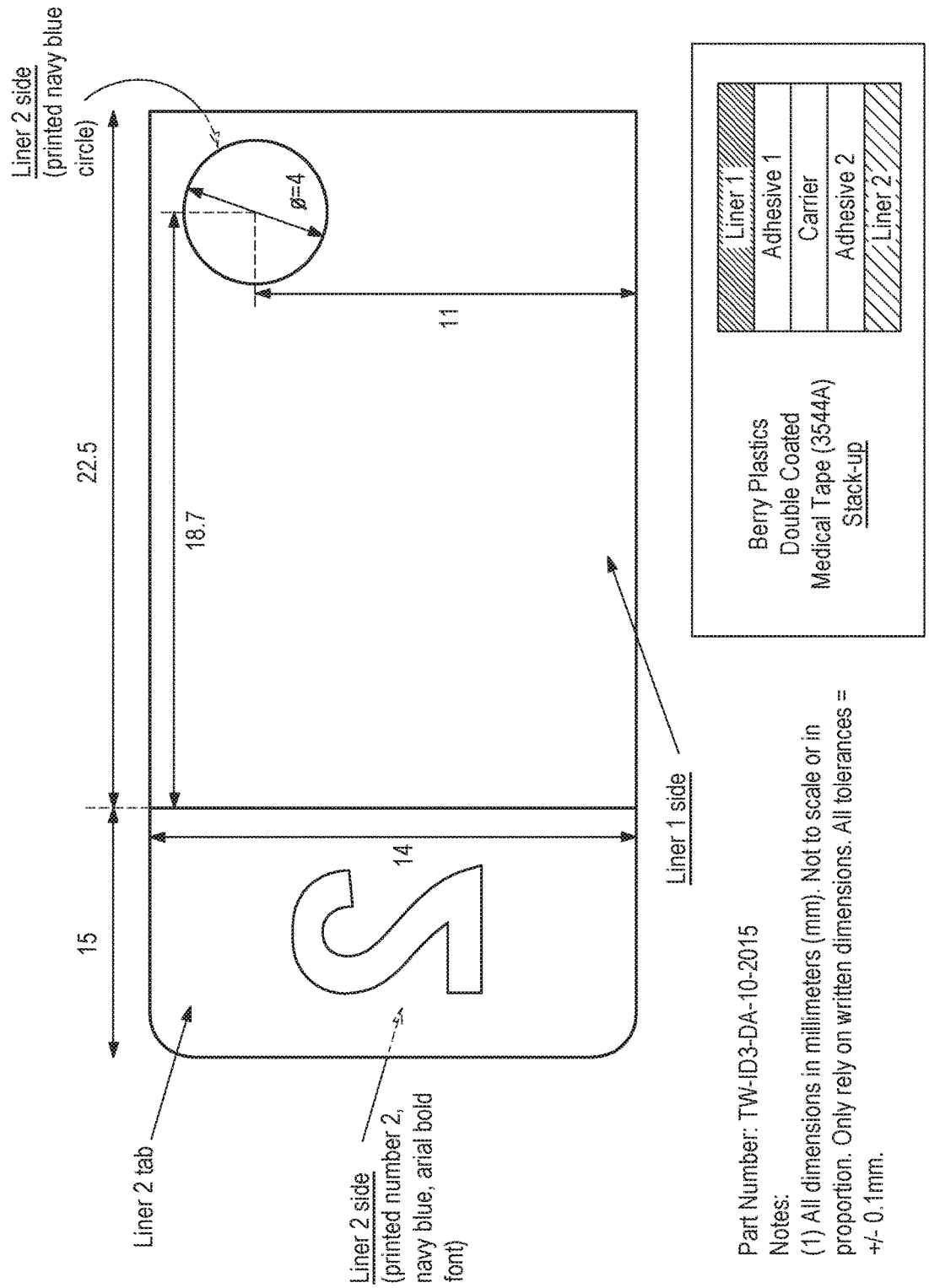

FIGS. 28A-C show one of the many alternative ways in which the wireless, disposable, continuous pulse oximeter sensor can be packaged, including a 3-part adhesive tape design, in accordance with an embodiment of the inventions.

Figure 29:
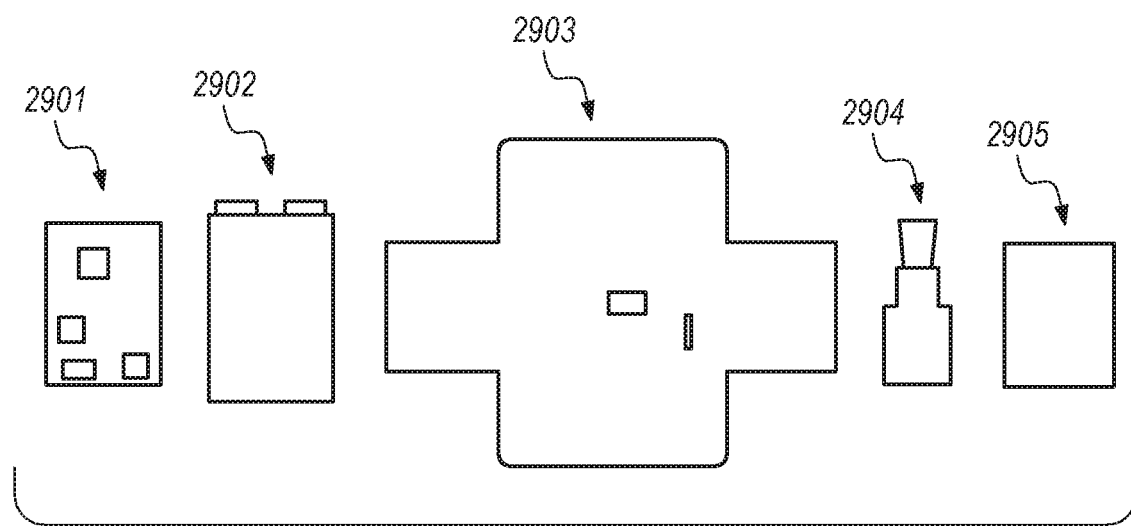
Figure 30A:
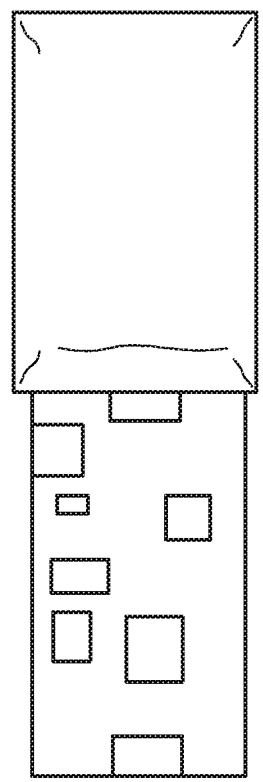
Figure 30B:
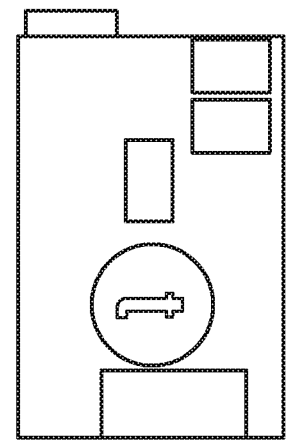
Figure 30C:
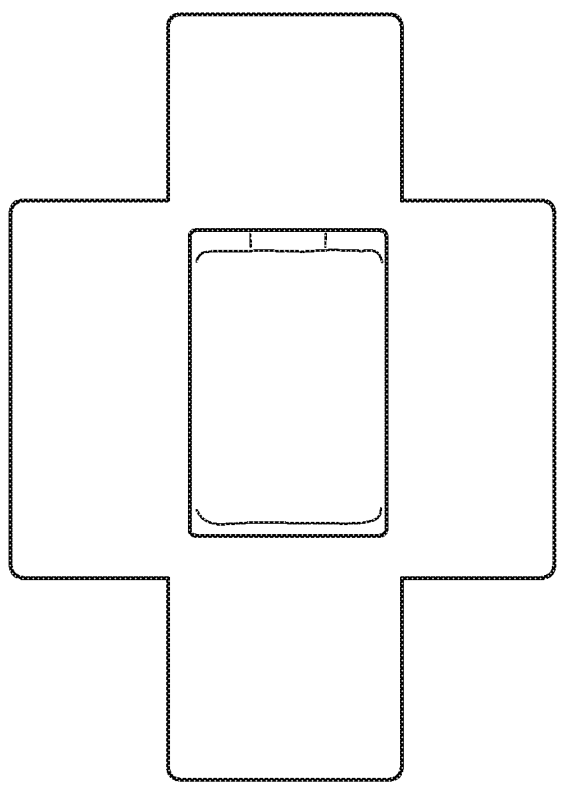
Figure 30D:
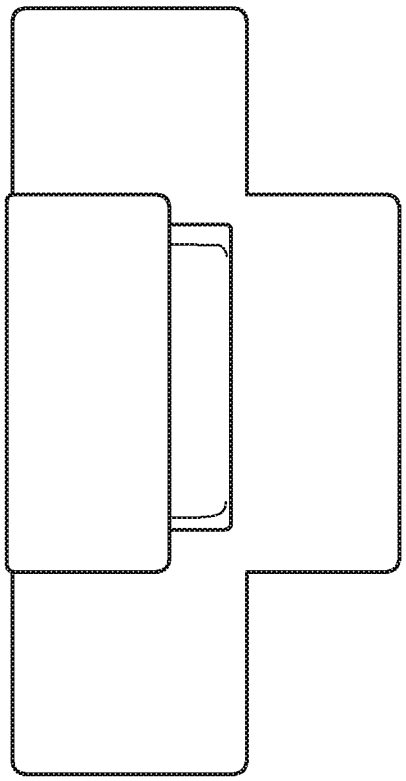
Figure 30E:
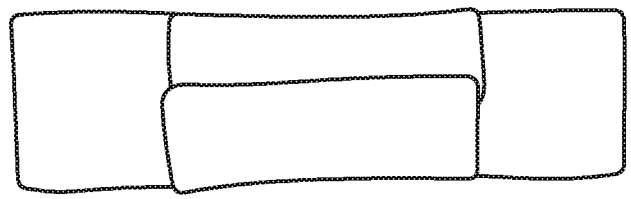
Figure 30F:
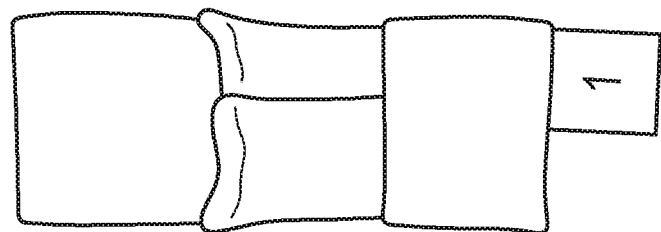
Figure 30G:
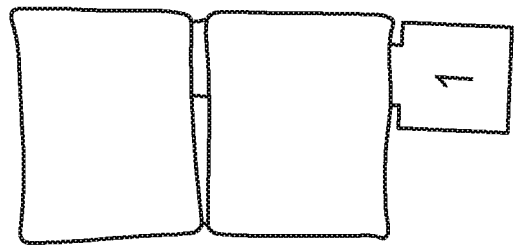
Figure 30H:
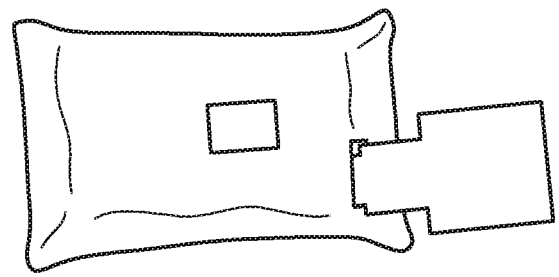

FIG. 29 shows a preferred exploded view of a wireless, disposable, continuous pulse oximeter sensor with a detuning resilient ceramic small-loop SMD antenna, in accordance with an embodiment of the inventions.

Figures 1, 27A:
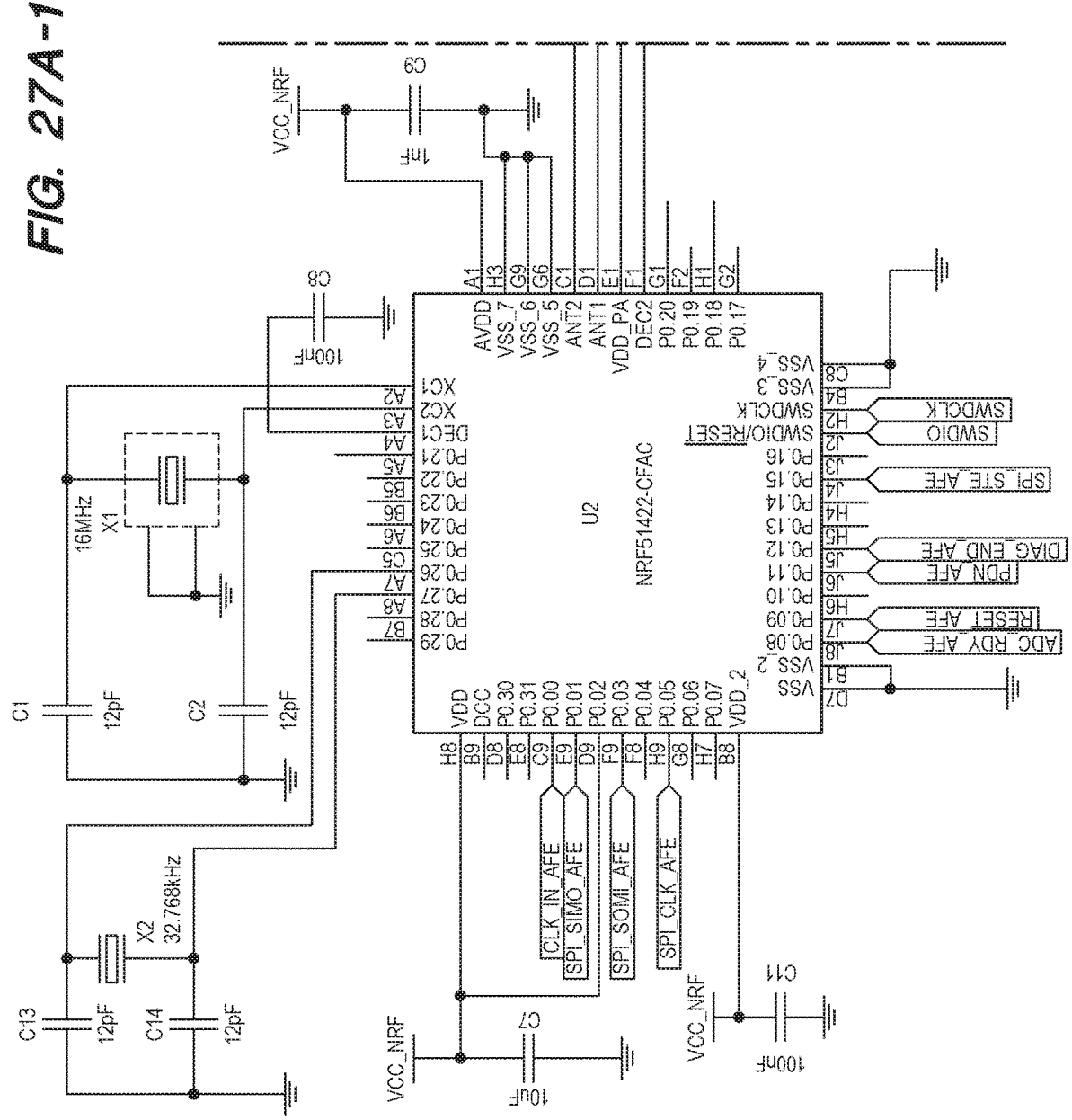
FIGS. 27A-C show a preferred signal processing unit and detuning resilient ceramic small-loop SMD antenna circuit schematic and printed circuit board layers (top and bottom)
Figures 2, 27A:
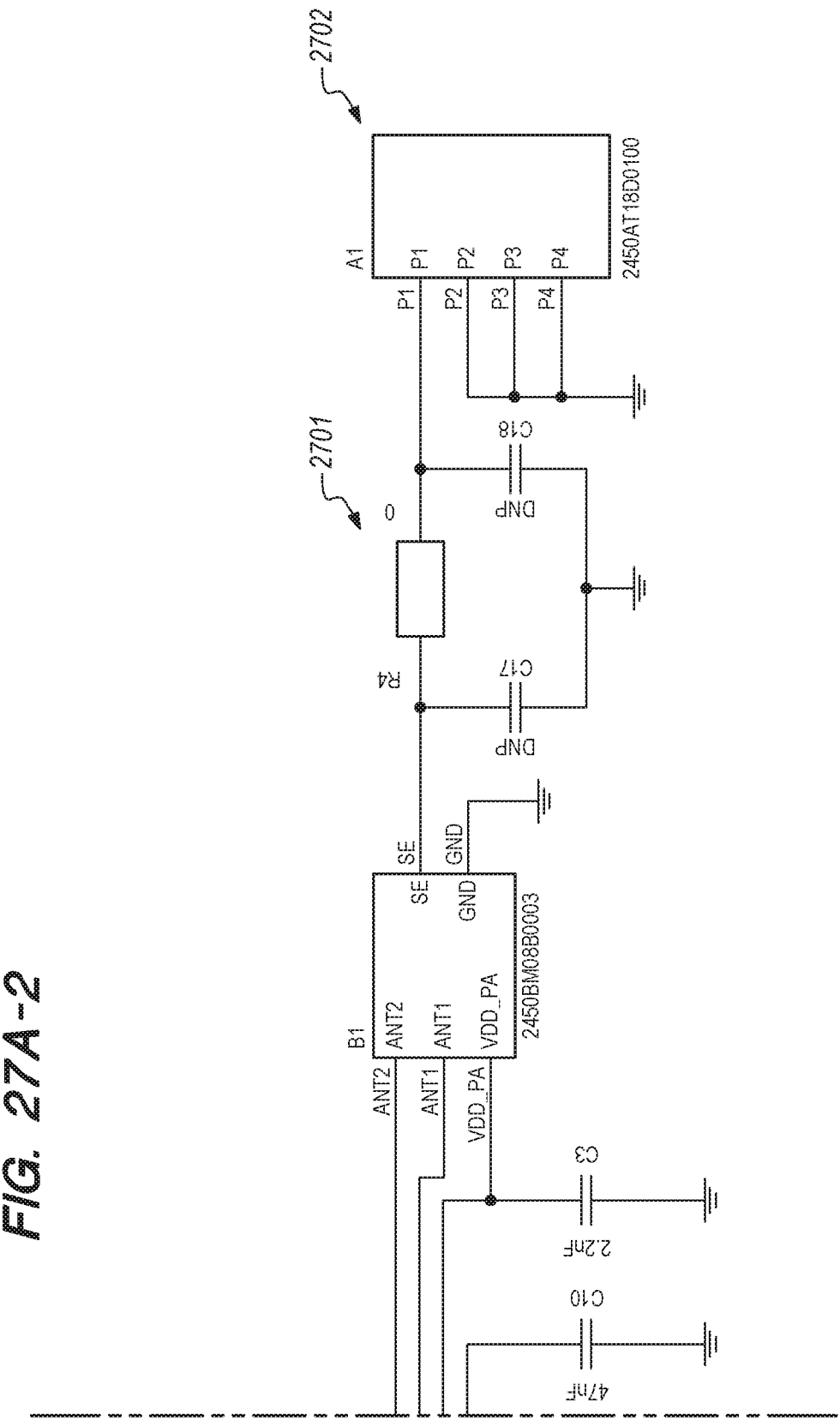
Figure 27B:
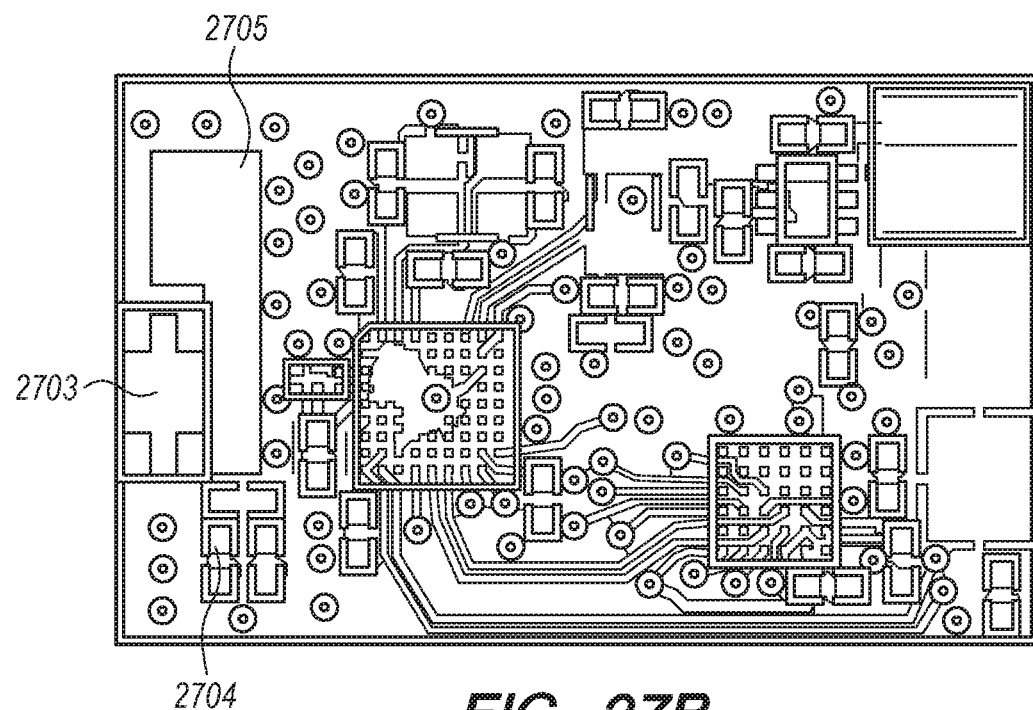
Figure 27C:
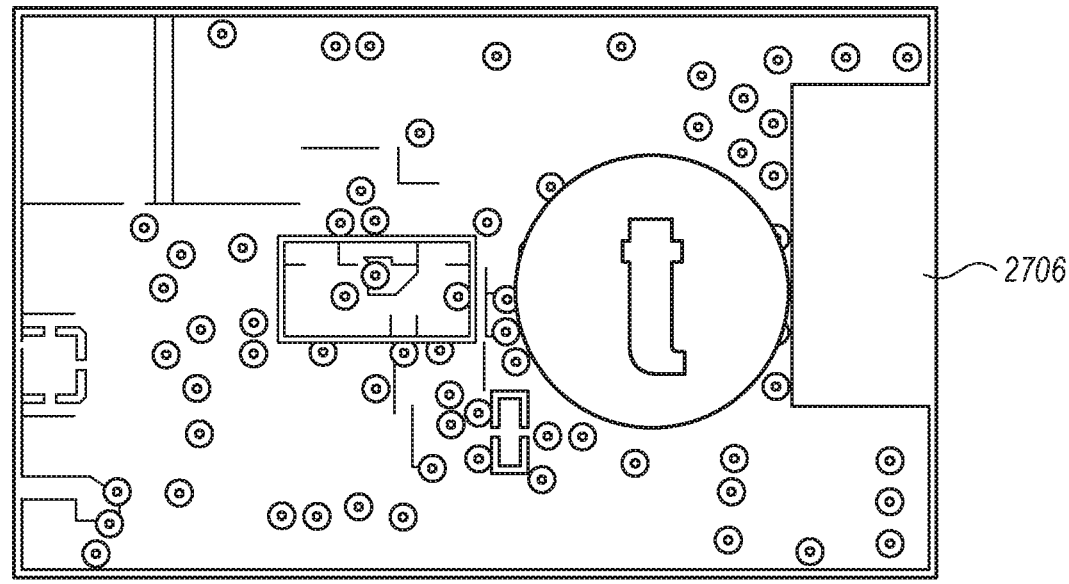

FIGS. 30A-H depict preferred example steps for attaching the adhesive tape assembly from FIGS. 28A-B to the pulse oximeter assembly-PCB assembly from FIGS. 27A-C, in accordance with an embodiment of the inventions.

FIG. 31 shows a preferred block diagram of the algorithms that may run on the sensor and the host, according to an embodiment of the inventions.

FIG. 32 highlights preferred design tradeoffs in the present inventions which enable the measurement of SpO2, PR, and PI using a small emitter-detector separation while still being able to produce acceptable signal-to-noise ratio figures.

Figure 33:
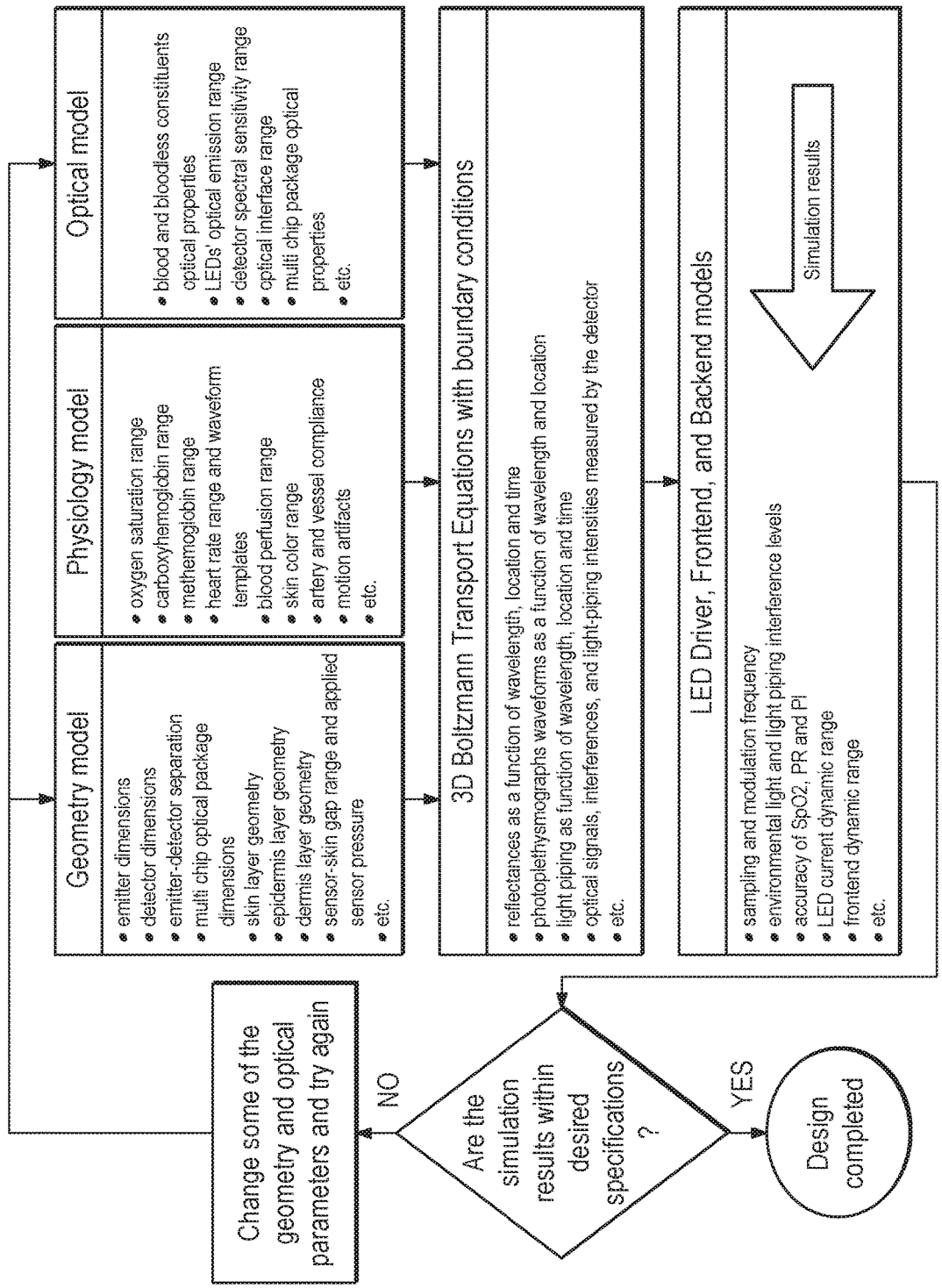

FIG. 33 details a preferred design methodology used in the present inventions to quantify the tradeoffs and actions defined in FIG. 32.

FIGS. 34A-C show some of the many additional/alternative modulation schemes that can be used in the present inventions depending on the measurement conditions and blood parameters of interest.

FIGS. 35A-D show some of the many examples of multi-chip packages with different optical and geometric configurations that may be used in the present inventions.

Figure 36A:
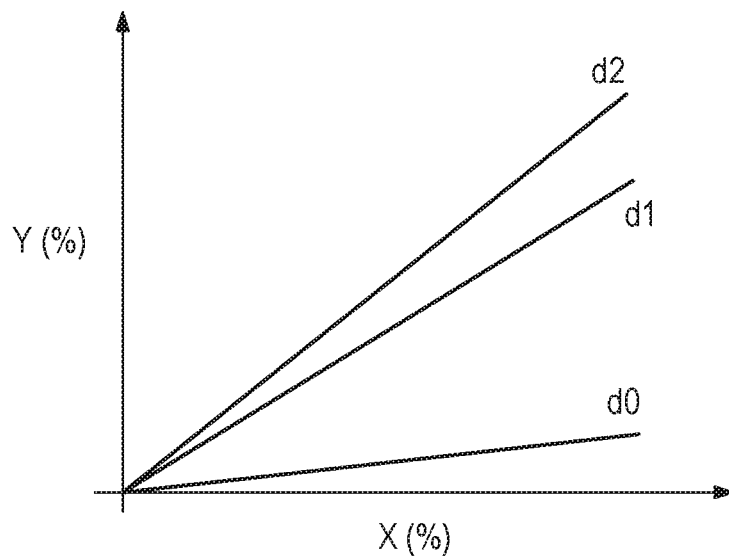
Figure 36B:
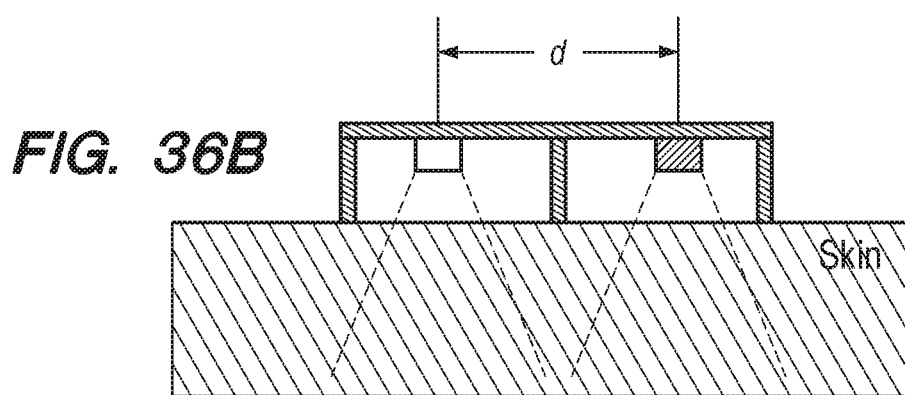
Figure 36C:
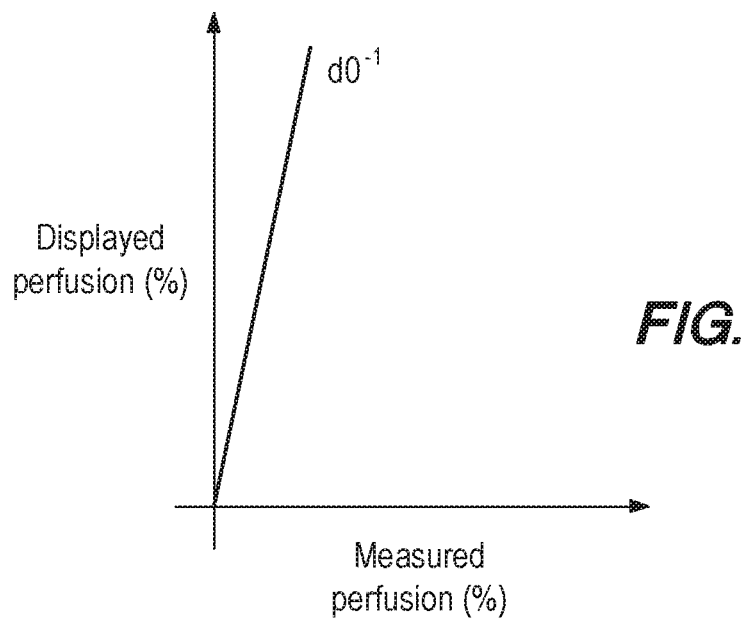
Figure 38B:
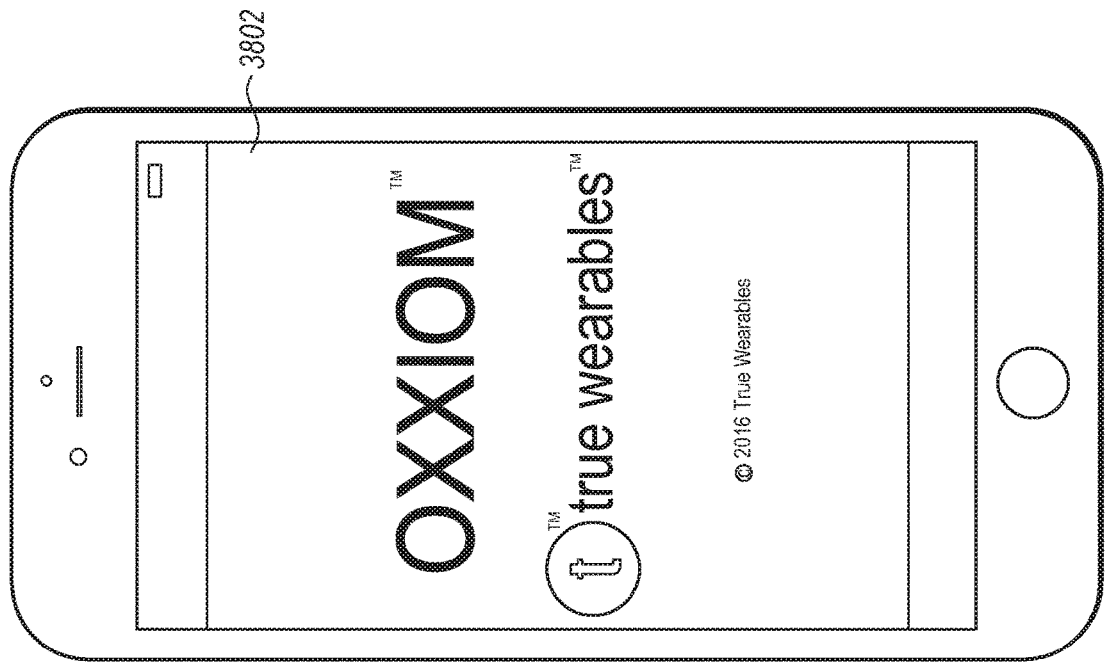
Figure 38A:
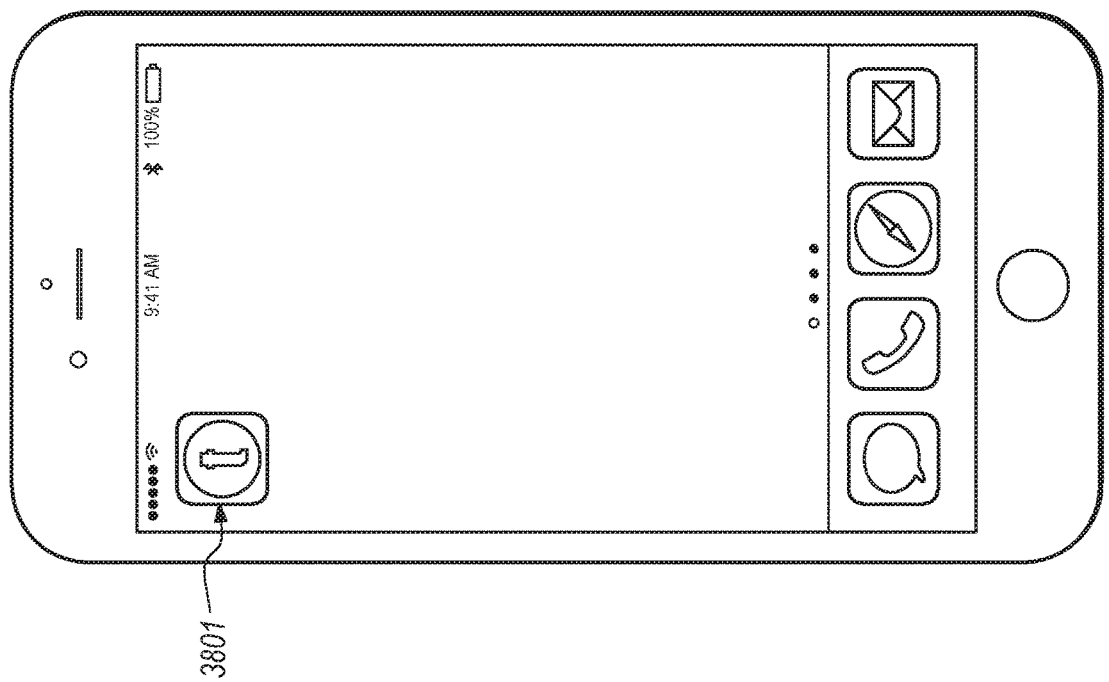
Figure 40A:
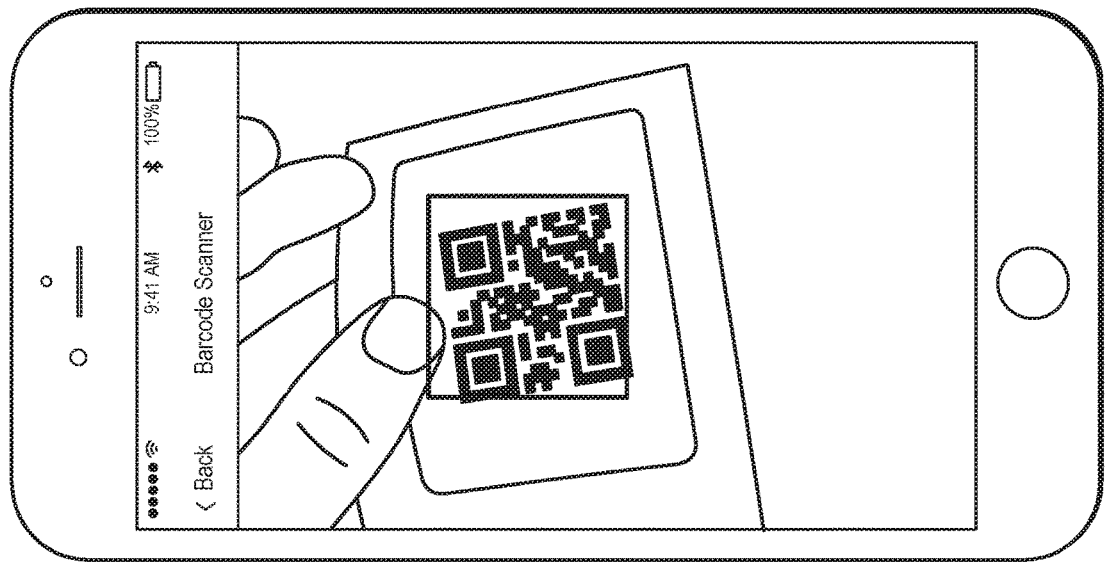
Figure 40B:
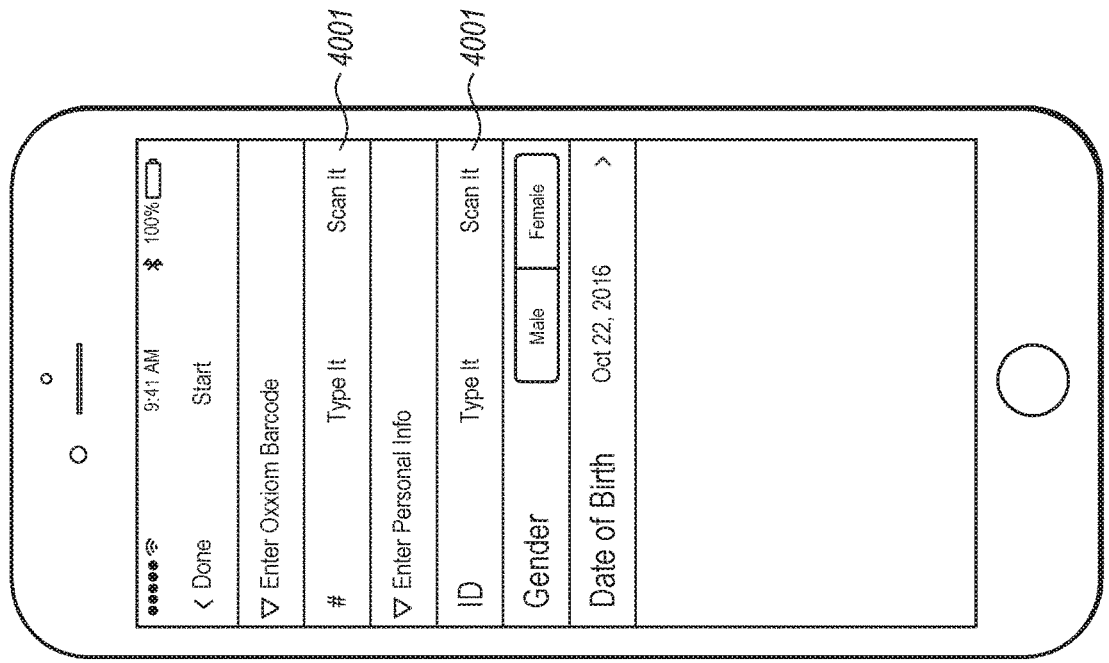
Figure 41B:
Figure 41A:
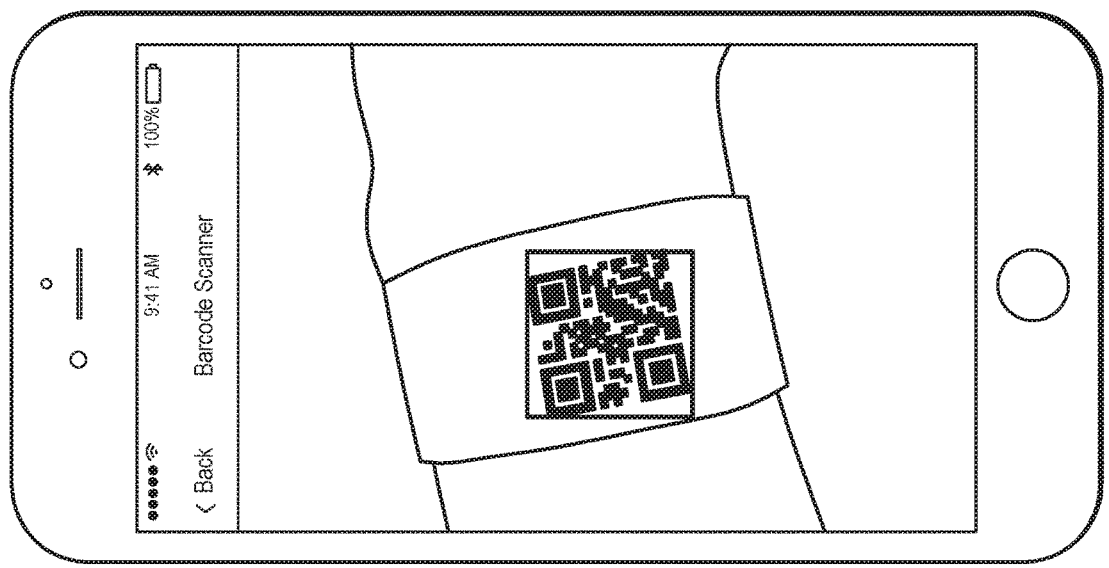

FIGS. 36A-C show how distance affects measured perfusion and the process of converting it to a displayed perfusion with levels that are compatible with conventional transmissive oximeters placed on a patent's digit.

FIG. 37 shows the typical workflow, advantages, and technical specifications of a wireless, fully disposable, single-use continuous clinical-grade oximeter (OXXIOM™) according to an embodiment of these inventions.

FIGS. 38-45 detail the features and workflow of the software that runs in the OXXIOM™'s host device (i.e, iPhone) so as to process, display, interact, and share the data received wirelessly from OXXIOM™.

FIG. 46 shows a sample of a Sleep Study Oximetry Report generated from the trend data for $SpO^2$, PR, and PI measured by OXXIOM™.

Figure 47:
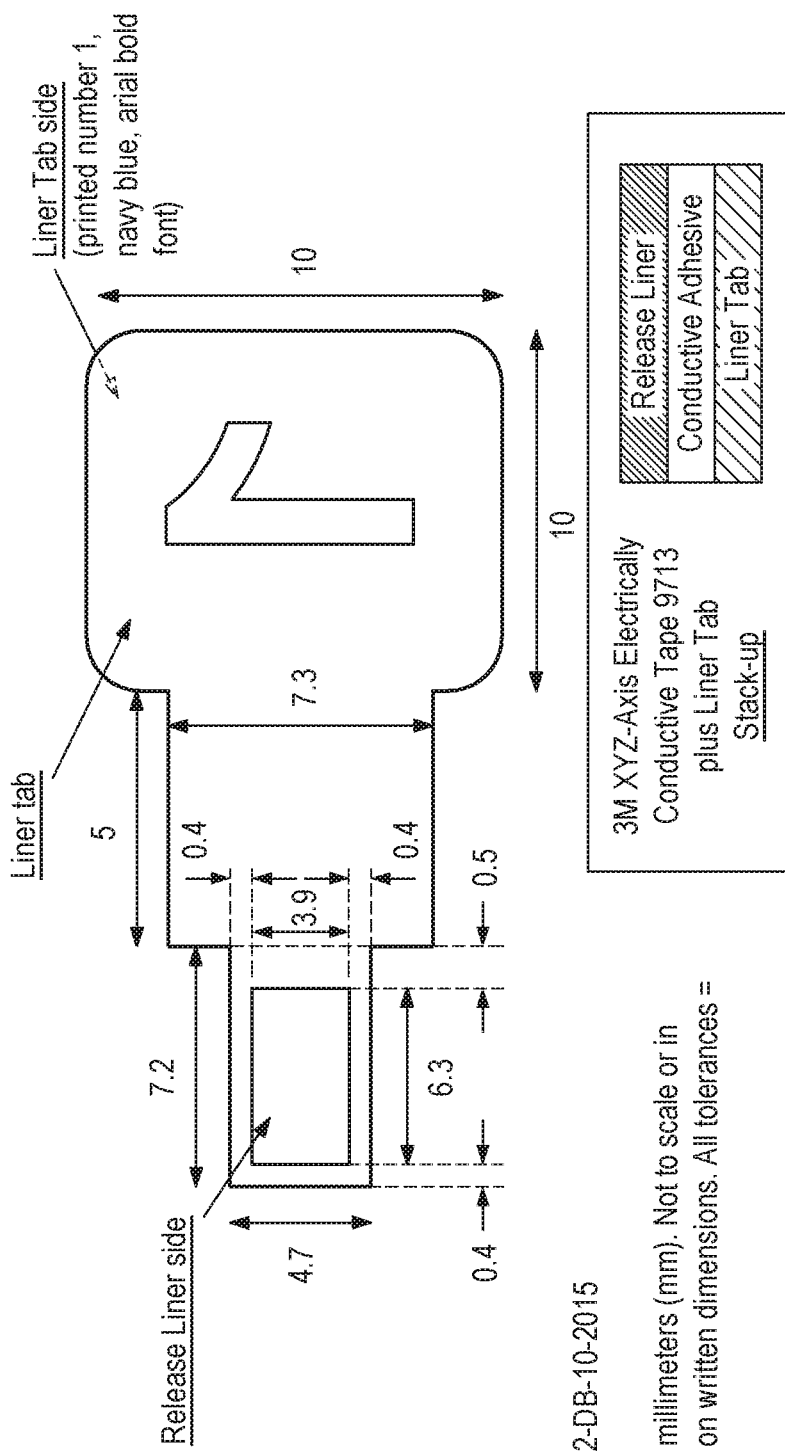

FIG. 47 shows an embodiment of a release liner with XYZ-Axis Electrically Conductive Tape needed to assemble the one-time ON switch that activates OXXIOM™.

Figure 48:
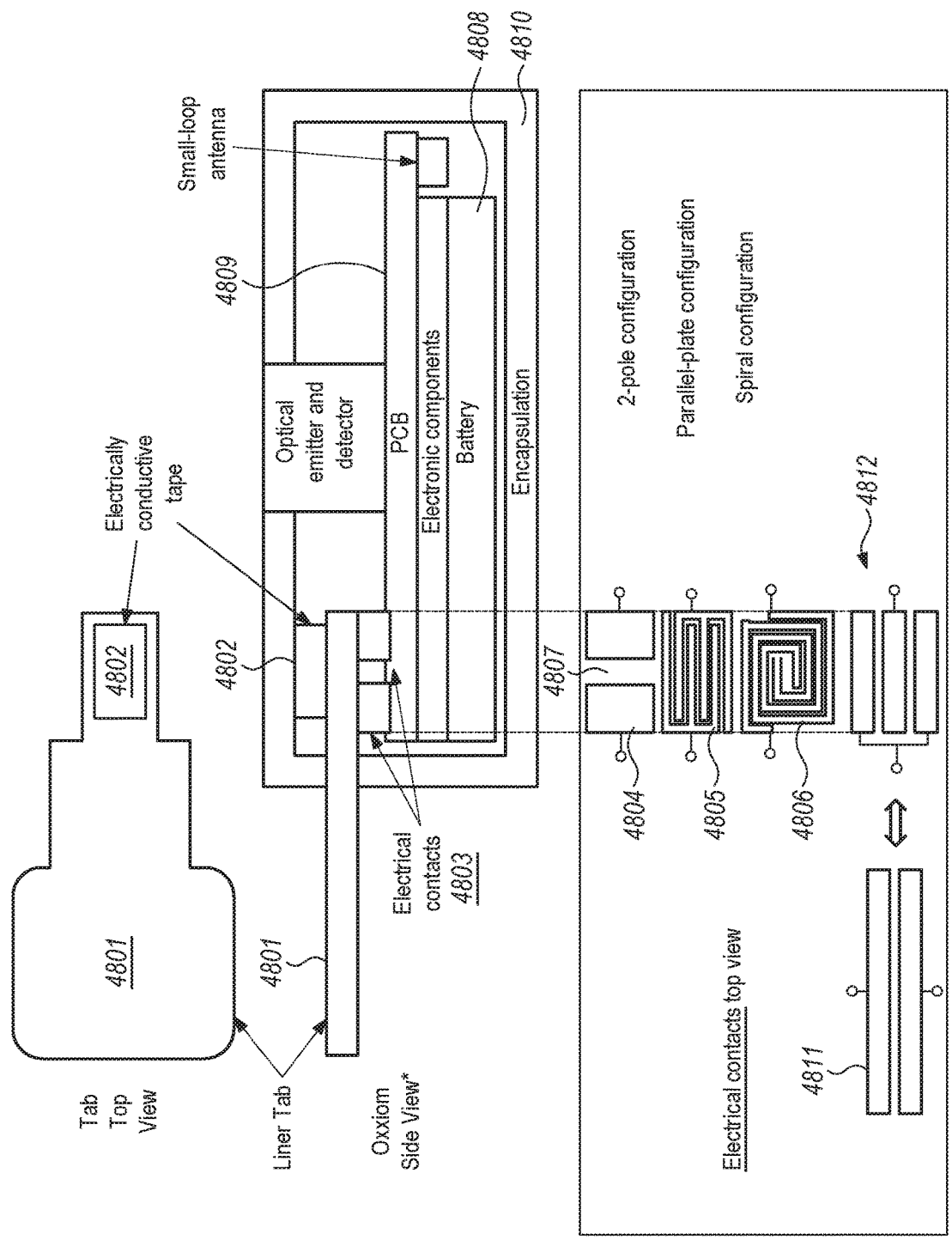

FIG. 48 depicts a detailed side view of OXXIOM™ with its main components as well as a top view of a few layout examples of electrical contact pads needed to create the one-time ON switch when combined (in the OXXIOM™ assembly) with the release liner shown in FIG. 47.

Figure 49:
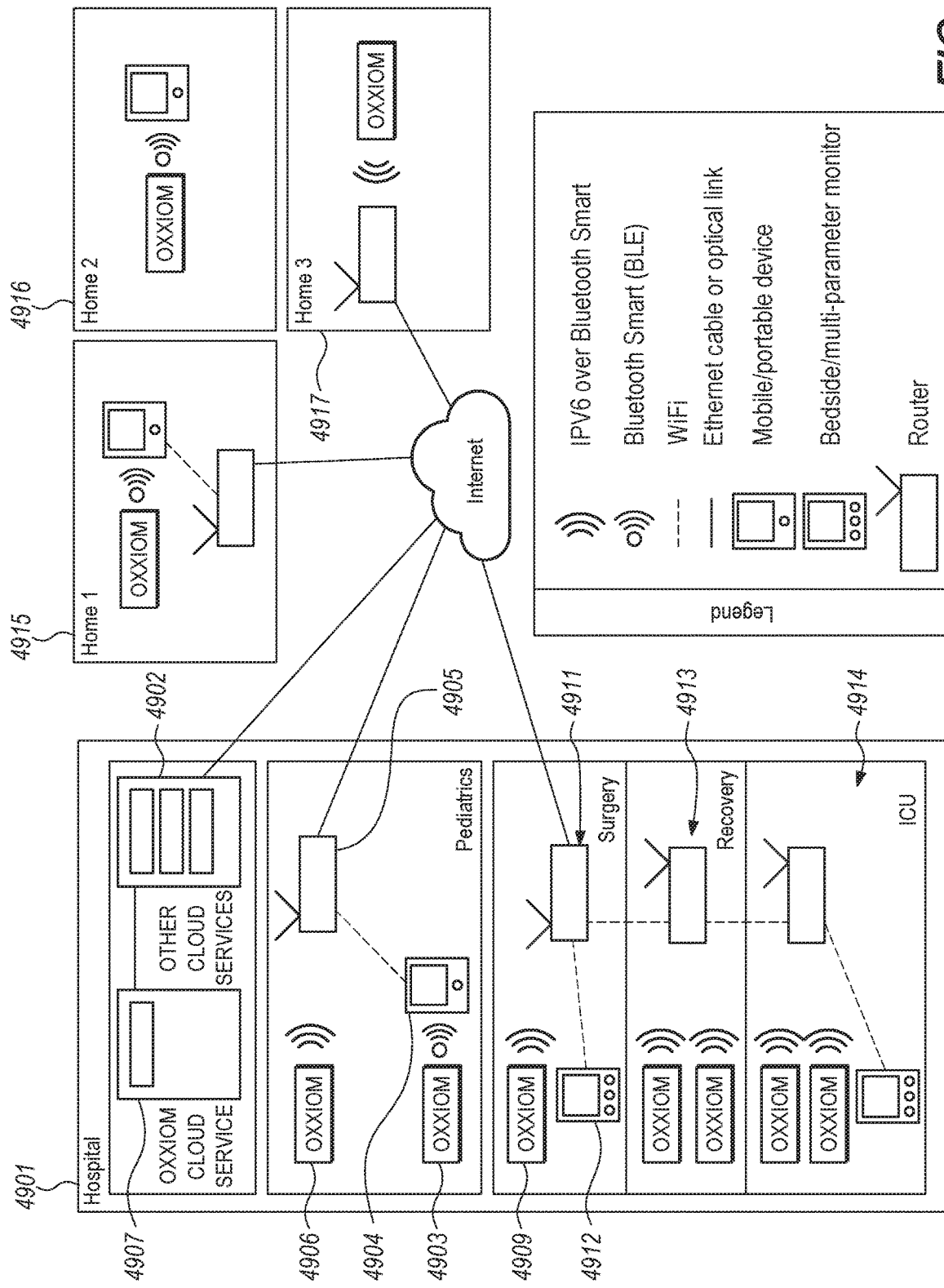

FIG. 49 shows several use cases for the OXXIOM™ oximeter aiming at delivering wireless, continuous, low-cost, clinical-grade monitoring solutions in home and hospital settings.

Figure 50:
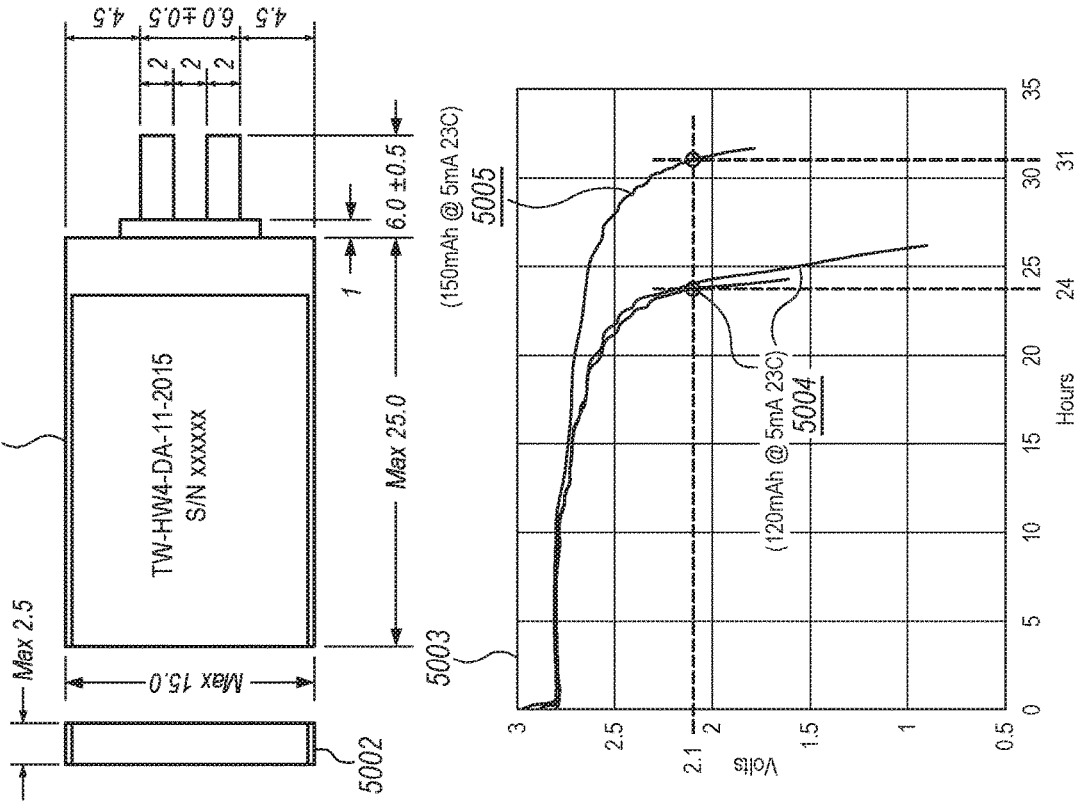

FIG. 50 depicts the drawings and technical specifications of OXXIOM™'s lithium manganese dioxide (Li—MnO2) custom primary (not rechargeable) battery.

Figure 51:
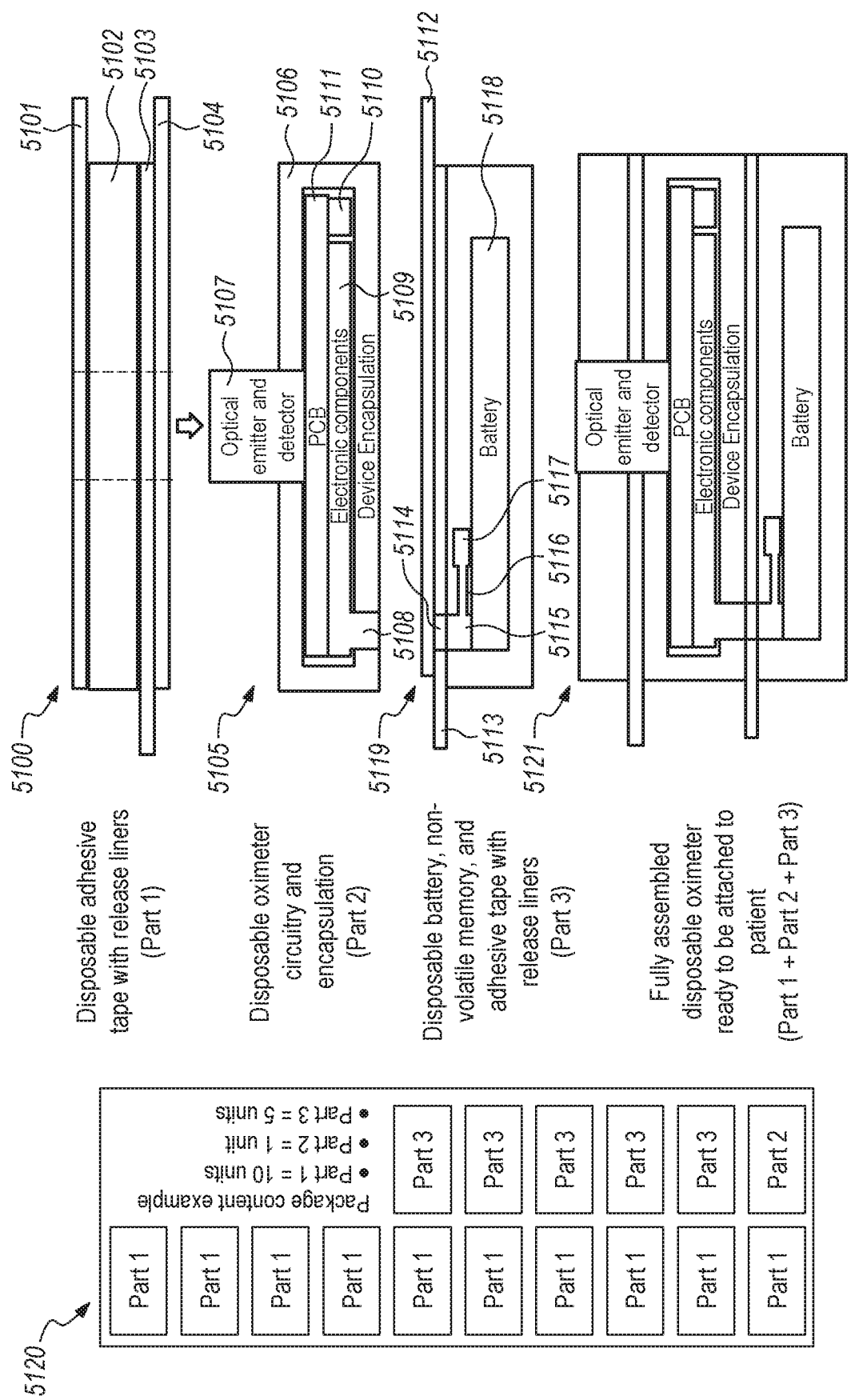

FIG. 51 shows an embodiment where a fully disposable single-use continuous wireless oximeter is divided into three main parts, in order to enable low-cost and long-term monitoring on a single patient.

Figure 52:
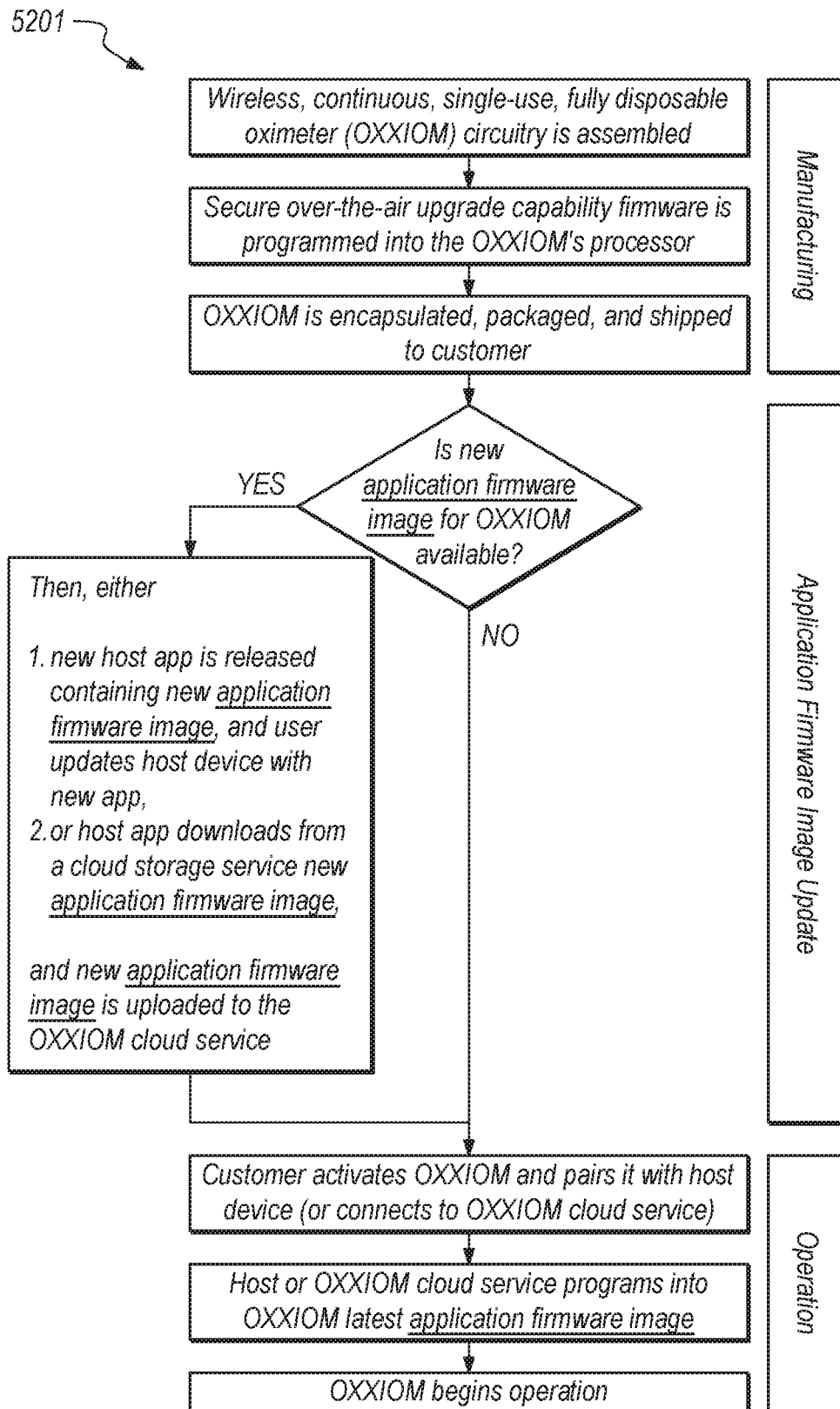

FIG. 52 shows a flowchart that describes the phases and main steps in OXXIOM™'s lifecycle when over-the-air firmware upgrade capability is available.

DETAILED DESCRIPTION

Various embodiments are now described with reference to the drawings, wherein like reference numerals are used to refer to like elements throughout. In the following description, for purposes of explanation, numerous specific details are set forth in order to provide a thorough understanding of one or more embodiments. It may be evident, however, that certain embodiment(s) of the invention(s) may be practiced without these specific details. In other instances, well-known structures and devices are shown in representative block diagram form in order to facilitate describing one or more embodiments.

In the following paragraphs, the present invention will be described in detail by way of example with reference to the attached drawings. Throughout this description, the preferred embodiment and examples shown should be considered as exemplars, rather than as limitations on the present invention. As used herein, the "present invention" or "the invention" or "the inventions" refers to any one of the embodiments of the invention described herein, and any lawfully-covered equivalents. Furthermore, reference to various feature(s) of the "present invention" throughout this document does not mean that all claimed embodiments or methods must include the referenced feature(s).

In a preferred embodiment, the present invention provides a wireless, disposable, continuous pulse oximeter sensor having a small footprint, requiring low power consumption and low manufacturing costs, and being monitor-agnostic. Preferably, the wireless, disposable, continuous pulse oximeter provides low power and compact instrumentation electronics, advanced signal processing and estimation algorithms, low-energy wireless communication protocols, and distributed computing as shown in FIG. 31. These and other benefits will become readily apparent in the following detailed description of the present invention(s).

Persons of ordinary skill in the art will understand that the various elements of the apparatus described herein can be made from a wide variety of suitable materials and processes. Preferably, the sensor of the invention is lightweight and sufficiently durable for its intended purposes, and is compatible with contact with human skin and does not pose any significant health hazard to most or all persons on whom the sensor may by applied. Similarly, the various communication technologies and protocols described herein can be any of a wide variety of suitable systems, preferably providing secure, low-energy, reliable communication between the sensor and other components of the invention(s).

Figure 1:
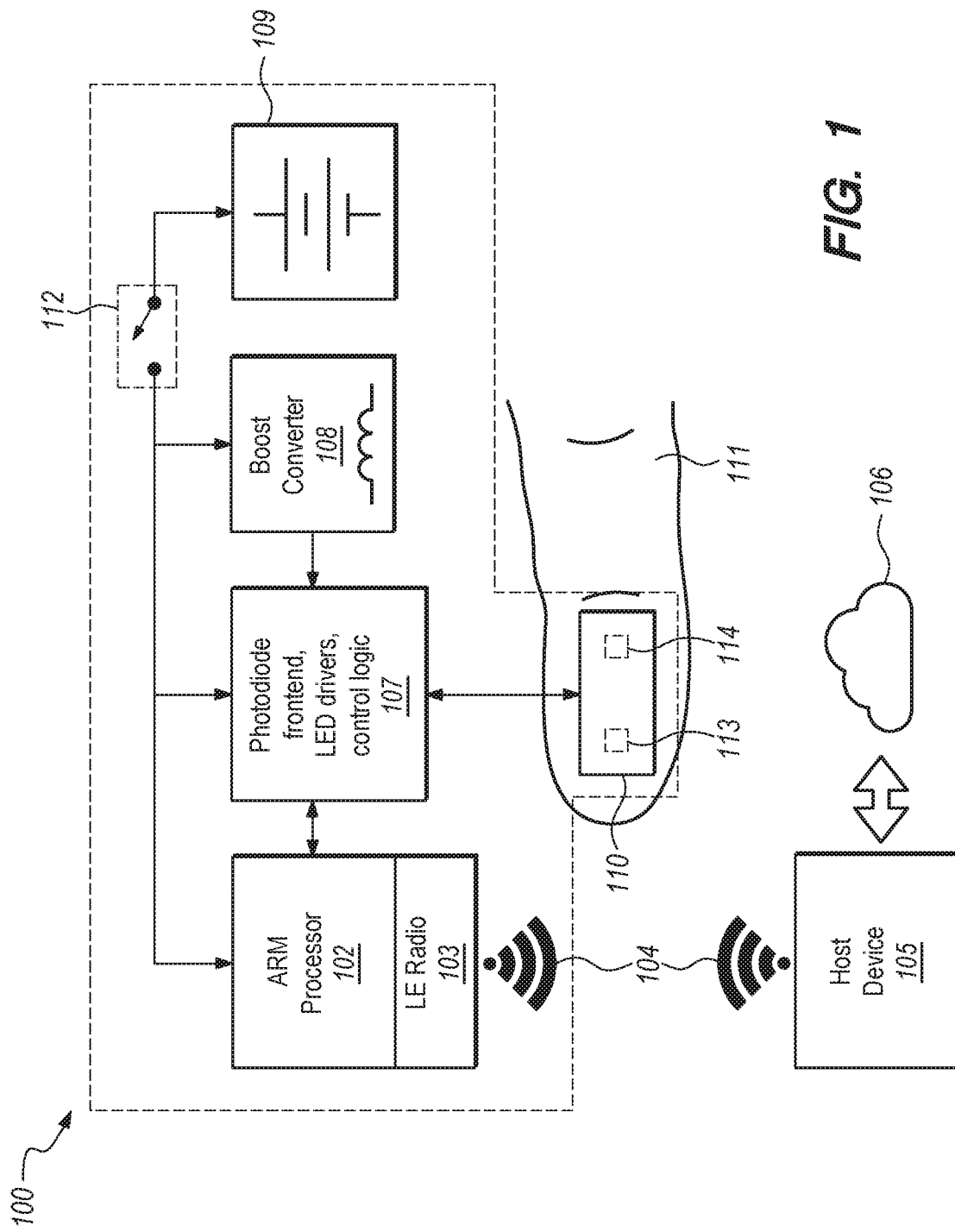
FIG. 1 is a block diagram of a wireless, disposable, continuous pulse oximeter sensor, according to an embodiment of the inventions.
Figure 2A:
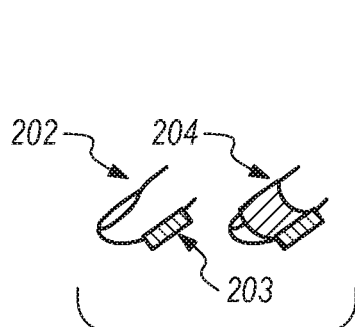
FIG. 2A shows two alternative embodiments of a wireless, disposable, continuous pulse oximeter sensor in accordance with the inventions, each of the embodiments attached to a digit, and each using a different adhesive tape layout (with those layouts depicted in greater detail in FIGS. 2G and 2H, respectively).
Figure 2B:
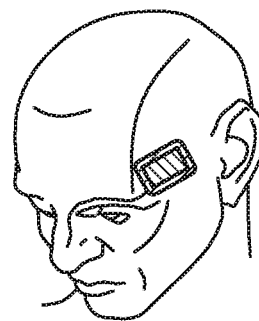
FIGS. 2B-F show additional measurement sites on a patient's body where disposable, wireless pulse oximeter sensors can be applied/mounted.
Figure 2C:
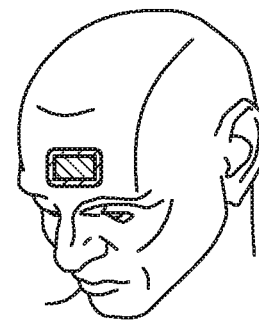
Figure 2D:
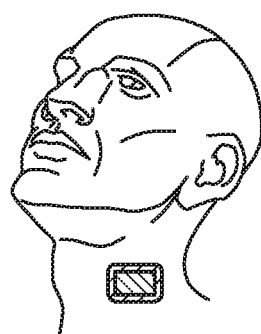
Figure 2E:
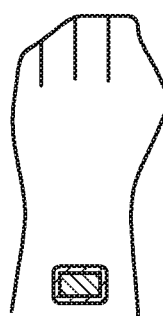
Figure 2F:
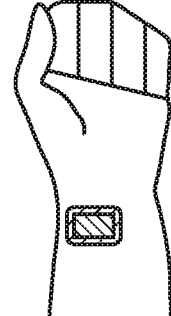

In a preferred embodiment of the invention, and as illustrated in FIG. 1, the wireless, disposable pulse oximeter sensor assembly 100 is attached to a patient's measurement site 111 such as a patient's digit (FIG. 2A), forehead (FIGS. 2B and 2C), or other site (such as shown in FIGS. 2D-2F) from which the sensor can readily access blood perfusion information. In a relatively simple embodiment, the pulse oximeter sensor assembly 100 is comprised of instrumentation electronics 107, a processor 102, a radio 103, adhesive tape, and a disposable battery 109. The sensor may be attached to a user's measurement site and turned on by means of a single-use, conductive tape-switch 112. The sensor assembly 100 may be wirelessly connected to a device 105 such as a smart phone, tablet, desktop or laptop computer, bedside monitor, or similar device so that measurement data may be transmitted from the sensor assembly 100 to the device 105 to be processed and/or displayed and/or stored, for alarms, for electronic medical record data transfer, and/or for data sharing, to name a few uses of the data provided by the sensor assembly 100.

Small Footprint

Preferably, the present invention provides a relatively small footprint (size) in its various components. Among other things, smaller size can require less material in manufacturing, improved ease of use, less room required for storage, less costs for transport, and a less intrusive device and instrument for patients' increased comfort and mobility when using the apparatus and methods of the inventions. In a preferred embodiment, the pulse oximeter sensor assembly 100 may contain a small printed circuit board (PCB) 1101 (FIG. 11) comprising a small footprint processor 102 with an integrated radio 103, a compact integrated circuit 107 containing instrumentation electronics for signal conditioning and LED current driving, and a built-in disposable battery 109 combined with a single DC-DC switched converter 108 to provide the required higher voltage to drive the LEDs 113 and/or a silicon photodiode 114 of the actual optical sensor 110. The processor 102 and instrumentation electronics 107 preferably are powered directly by the disposable battery 109. The optical sensor 110 preferably is encapsulated with the PCB by any of a wide variety of suitable apparatus and methods, including (by way of example) by attaching flexible adhesive tapes of various types (optionally combined with PTFE) to the PCB. Persons of ordinary skill in the art will understand that the PCB may be rigid or flexible, or be in the form of a substrate where some or all the components are die attached and wire bonded to the substrate, and encapsulated for protection using epoxy or some other encapsulation material. Further, the sensor element 110 may be attached to the patient 111 using any of a wide variety of suitable apparatus and methods, including (by way of example) by using the adhesive tapes that are part of the sensor 110 encapsulation structure (as described herein).

Low Power Consumption

In a preferred embodiment of the present invention, low power consumption may be attained using a low-power ARM processor 102 with dual functionality for controlling a wireless low energy radio 103 and instrumentation electronics 107. Preferably, the sensor element 110 comprises high efficiency LEDs 113 and at least one silicon photodiode (photodetector) 114, and are arranged in a reflective configuration such that the LEDs 113 and at least one silicon photodiode 114 are physically separated from each other in order to minimize the required LED currents and frontend gains in the instrumentation electronics. Preferably, the instrumentation electronics 107 have very low bias currents and also operate at low voltages. In a preferred embodiment of the invention, ambient light interferences may be avoided or at least reduced by modulating and time-multiplexing the LEDs' currents at a higher frequency in order to shift the spectral content of the generated and detected optical signals to a range in the spectrum where ambient light interferences are less likely to occur. A preferred modulation scheme 3101 as shown in FIG. 31 may reduce the complexity of the demodulation, decimation, LED current calibration, sensor off patient, error handling and alarms, diagnostics, and communication algorithms shown in sensor algorithm block diagram 3002 running on the sensor processor 102. In this type of preferred modulation, each LED is kept turned on for approximately 25% of the modulation time cycle (LED duty cycle). Smaller LED duty cycles can be used in order to reduce overall power consumption. The LEDs preferably are kept turned off for approximately 50% of the modulation time cycle. The intervals where the LEDs are turned off can also be increased if the LED duty cycles are to be reduced and if the modulation frequency is kept the same. The preferred two slots where the LEDs are turned off are used to probe and cancel the effects of ambient light. If sophisticated filtering and signal processing are employed in the demodulation scheme in order to recover the optical signals generated by the interplay of the LEDs optical signals and the attenuation caused by the measurement site's blood perfused tissue, then modulation frequencies as low as 1 KHz can be adopted with signal-to-noise ratio figures similar to medical-grade pulse oximeters. If the preferred low-cost low-power pulse oximeter frontend from Texas Instruments, AFE4403 is used as the instrumentation electronics 107, then it can be programmed to generate and control directly the required LED modulation scheme without the need for additional resources from the sensor processor 102.

Modulations as shown in FIG. 34A can also be adopted in the case of measurement sites with low perfusion and/or subject to excessive motion. FIGS. 34B-C show some of the possible scenarios where a particular type of modulation would be advantageous. A decision-making process algorithm is depicted in FIG. 34B, where the adopted modulation scheme depends on the factors aforementioned. For RED-GREEN-IR modulation shown, green and red LEDs are activated and modulated for a period of time according to the on-off pattern described, and then, the red LED (RED) is replaced with the near-infrared LED (IR) and also modulated for a period of time. This sequence of events repeats itself while the measurement site is subject to motion and/or low perfusion levels. When light in the wavelength range between violet and yellow (i.e., between 400 to 590 nm approximately) is applied to a blood-perfused measurement site, the higher light scattering and absorption seen in this region, create photoplethysmographs that are much larger in amplitude when compared to the ones in the red and near-infrared wavelength regions. Typically, the green wavelength is used because LEDs in this range offer good efficiency and reliability as well as lower cost when compared to other wavelengths in the violet-yellow range. Also, the optical properties of blood in the green region are desirable in terms of scattering and absorption levels. The photoplethysmograph associated with the green LED can be used to improve detection of the heart rate and/or the detection of the red and near-infrared true photoplethysmograph amplitudes and waveforms, which are required for an accurate measurement of the blood's oxygen saturation under low-perfusion and motion conditions.

The Multi-Wavelength Sequential Modulation can be used in case the parameters of interest require other wavelengths in addition to the red and near-infrared LEDs. Examples include the non-invasive measurement of other blood constituents (parameters), such as glucose, for diabetes disease management, water, for body hydration management, total hemoglobin, for anemia and/or blood transfusion management, etc. As shown in FIG. 34A, a number of light sources of various centroid wavelengths (i.e., $\lambda 1, \lambda 2, \ldots, \lambda n$ LEDs) are turned on and off sequentially over time. In the case of the non-invasive measurement of glucose, multiple LEDs in the range of 900 nm to 1700 nm can be adopted. In the case of the non-invasive measurement of total hemoglobin and/or water, wavelengths in the range of 600 nm to 1350 nm should be sufficient. The spectral ranges defined are sufficient because blood and bloodless components at the measurement site have spectral features that are typically quite distinctive depending on the wavelength sub-range under consideration. For instance, water and glucose have higher absorption in the 1550 nm to 1700 nm range than the other components, the hemoglobin species have pronounced features in the 600 nm to 1350 nm, fat has in general pronounced scattering properties throughout the whole range when compared to other blood components, and so on and so forth. The modulation schemes shown in FIG. 31 and FIG. 34A can be switched over time depending on the particular application and/or measurement conditions.

FIG. 34C shows the case of a multi-parameter sensor that continuously measures SpO2, PR and PI, using modulation shown in FIG. 31, and/or the RED-GREEN-IR modulation, shown in FIG. 34A, and perform lower-frequency periodic spot-check measurements of other blood parameters, such as the ones previously mentioned (i.e., glucose, water, etc.) using the Multi-Wavelength Modulation. Such a topology is possible because typically water, glucose, hemoglobin, etc. concentrations in blood vary slower when compared to SpO2, PR and PI. Because typical measurement periodicity for the said parameters is in general much longer (i.e., once every 30 minutes, once an hour, etc.), the increase in the sensor power consumption is not significant. The additional LEDs and detector technologies (i.e., silicon and indium gallium arsenide photodiodes for the 600 nm to 1700 nm wavelength measurement range) required represent small incremental cost and negligible increase in sensor footprint.

The Multi-Wavelength Modulation shown in FIG. 34A can also be used to measure SpO2, PR and PI. In this configuration, the red and near-infrared LEDs are combined with other wavelengths to create "n" photoplethysmographs that could be used to improve SpO2 accuracy or motion performance. Accuracy is improved because additional LEDs throughout the visible and near-infrared range enable estimation algorithms to counter the optical interference effects of other blood and bloodless components not needed in the measurement of oxygen saturation, pulse rate and/or perfusion. Operation under motion is improved because the effects of motion acceleration on the venous and capillary blood creates optical interferences in the measurement site that have distinct morphological features depending on the wavelength range, and hence are more likely to be eliminated from the photoplethysmographs through advanced signal processing.

Persons of ordinary skill in the art will understand that the wavelengths and other measurements and ranges discussed herein are generally intended to be representative of certain embodiments of the inventions, and not as delimiting as to the many ways in which the inventions can be practiced.

In certain embodiments of the invention, in order to compute SpO2, PR and PI, a distributed computing architecture may be used where SpO2, PR and PI are estimated on the host processor in order to increase the sensor's battery life as shown in block diagram 3003. Preferably, the sensor processor 102 may execute the time critical, high frequency, low latency and low complexity tasks. Data processed by the sensor processor 102 may be reduced in bandwidth by decimation algorithms, and sent wirelessly to a host processor 105. In a preferred embodiment, the host processor 105 may execute more complex, high latency tasks in order to calculate and continuously display the measurement values for SpO2, PR and PI.

Figure 4:
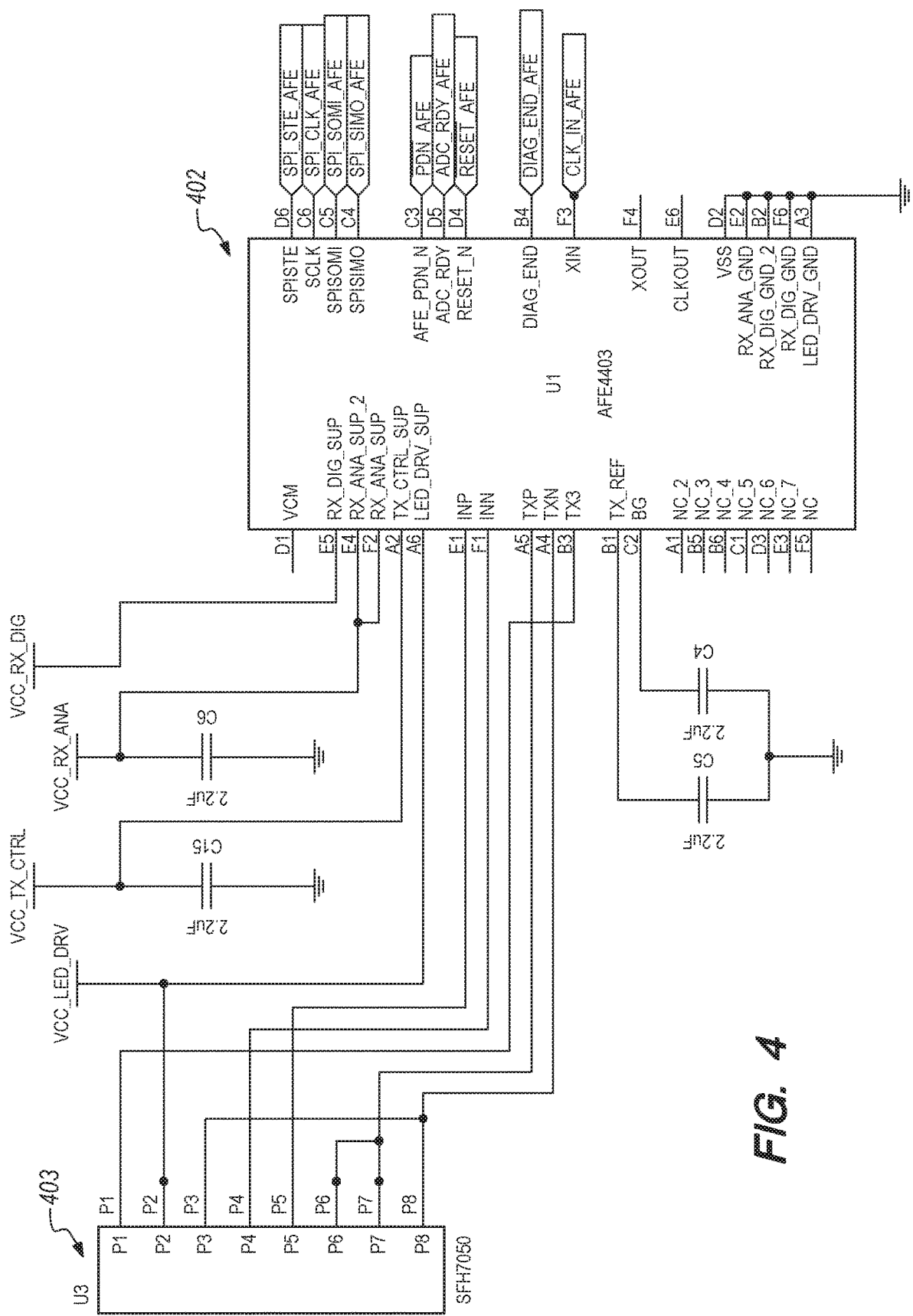
FIG. 4 shows a frontend circuit schematic of a wireless, disposable, continuous pulse oximeter sensor, in accordance with an embodiment of the inventions.
Figure 7A:
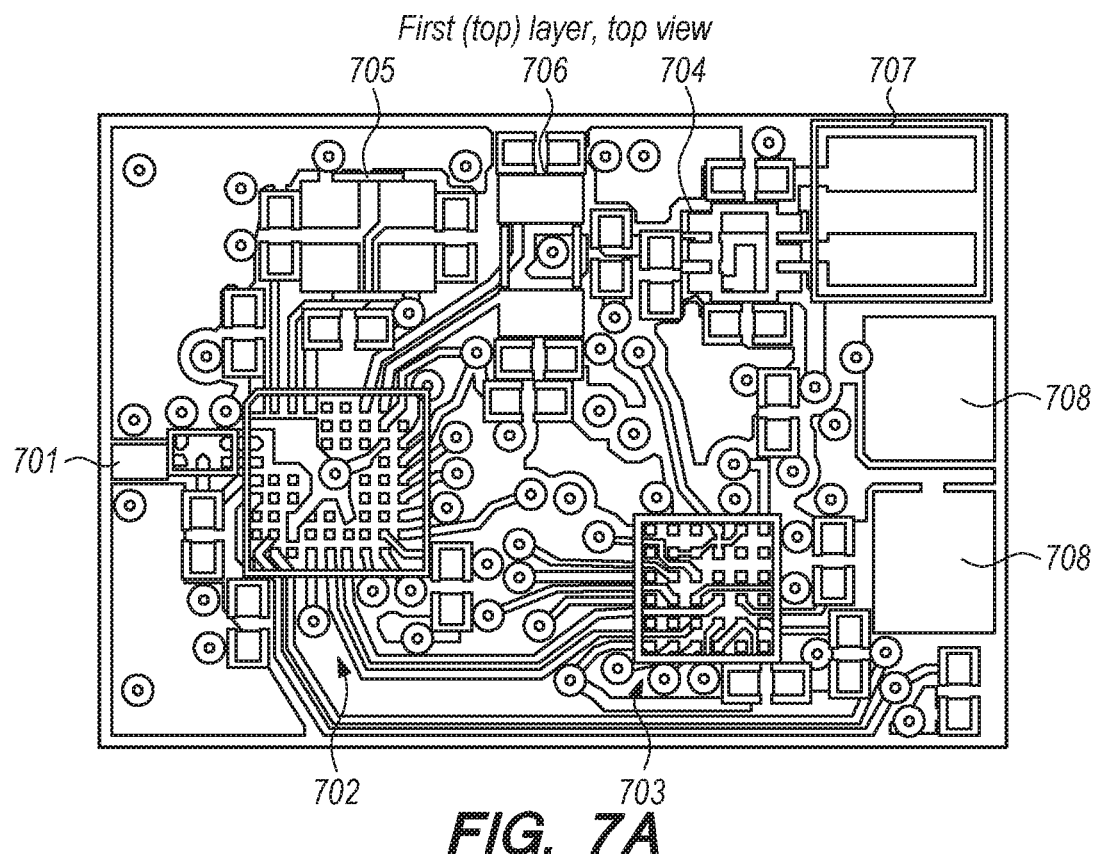
FIGS. 7A-D depict printed circuit board layers of a wireless, disposable, continuous pulse oximeter sensor, in accordance with an embodiment of the inventions.
Figure 7B:
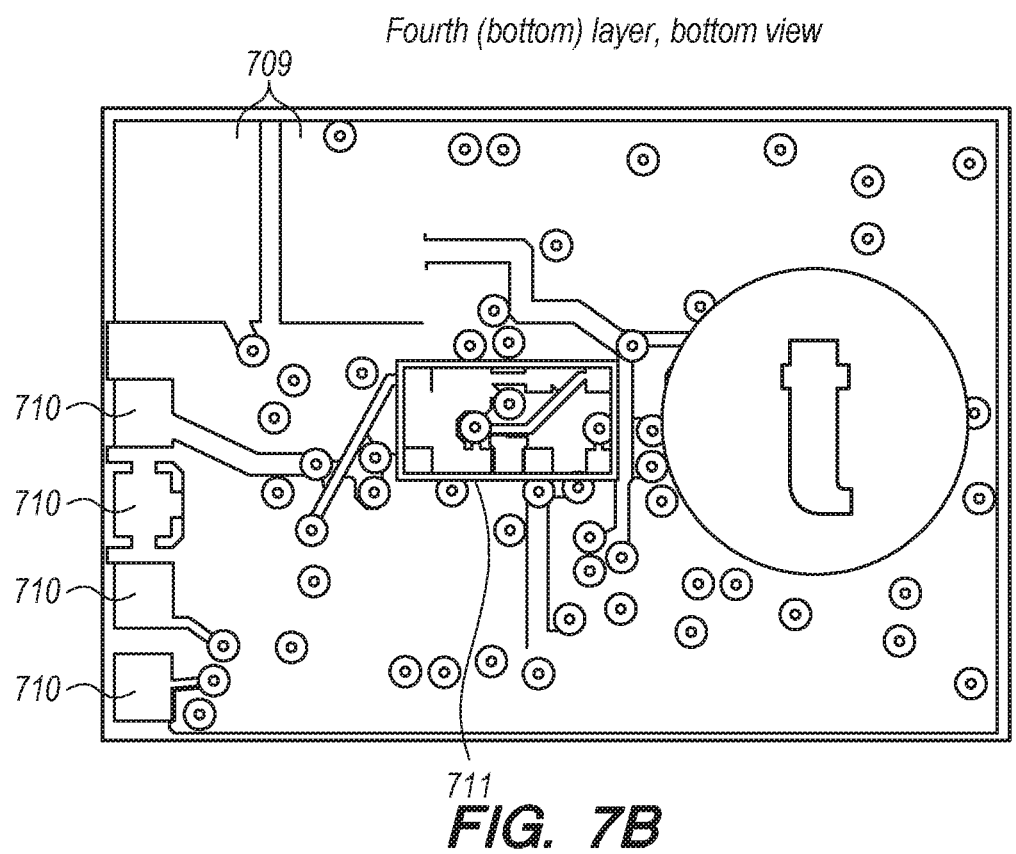
Figure 7C:
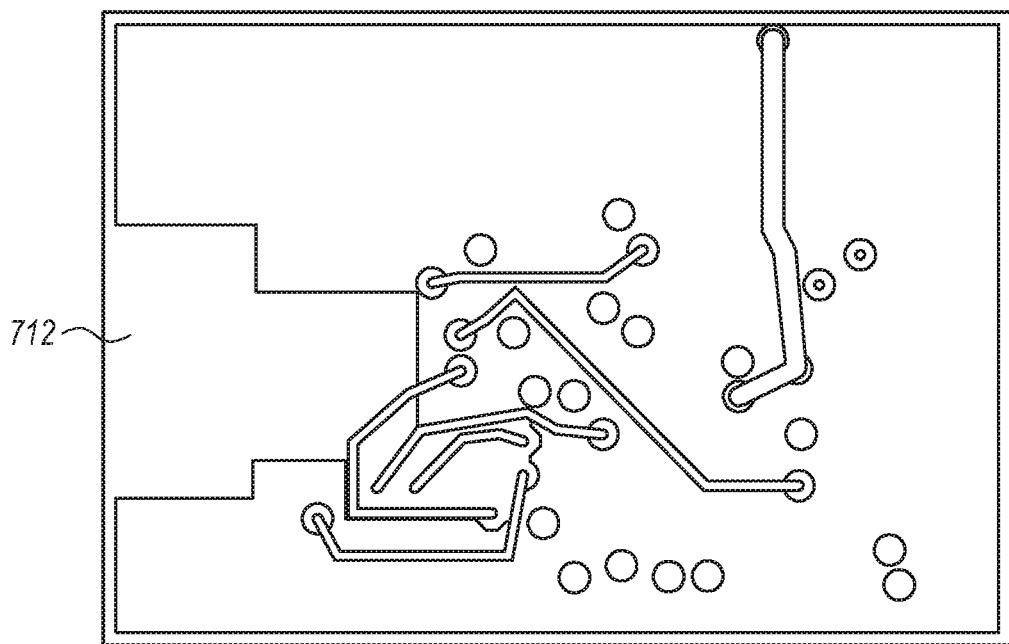
Figure 7D:
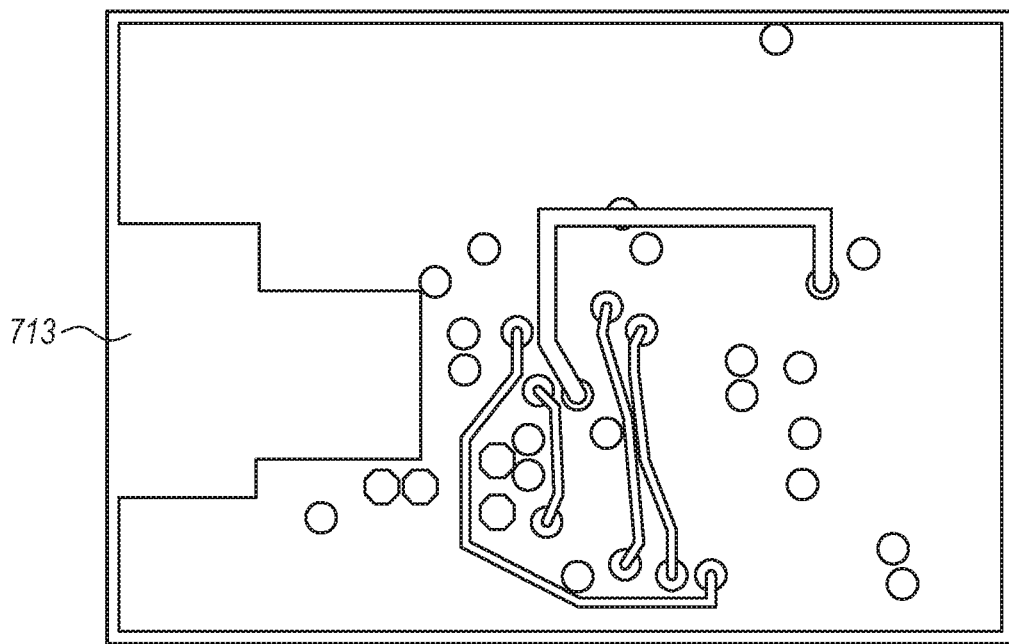

Another issue related to power consumption has to do with the current levels the LEDs are required to operate. In order to obtain photoplethysmographs with acceptable signal-to-noise ratio, the LEDs must be driven by appropriate current levels that are functions of the optical path between emitter and detector for a given subject state and sensor frontend electronics and signal processing configurations. The larger the optical path, the higher the required LED currents and the deeper the optical penetration. In order to reduce the power consumption by the LEDs, it is desirable to use a very small emitter-detector separation. However, small emitter-detector separations create shallow optical probing and increase the chances of the light generated at the emitter to reach the detector without passing through the tissue's blood perfused inner layers (light piping). In some preferred embodiments of the inventions, the use of small emitter-detector separation is obtained by using a multi chip package 403, 711 such as the SFH7050 from OSRAM Opto Semiconductors as shown in FIGS. 4 and 7B with picture showing it attached to a PCB in FIG. 13A, and a bandage that increases the optical coupling between sensor and skin as shown in FIGS. 25A-H. The multi chip package SFH7050 has an optically dark background in the emitter-detector gap region, and a small wall separating physically the emitter and detector regions. The tradeoffs involving emitter-detector separation, applied sensor pressure, light piping, photoplethysmograph amplitude, and LED power consumption are shown in FIG. 32.

An optically "dark" background as discussed herein preferably is a surface that absorbs most of the optical energy received in the wavelength of interest without reflecting it back. It is not only associated with the color of the background but also with the optical and mechanical properties of the chip or multi-chip package background and/or cavities that prevent light from being reflected back to the measurement site for a given wavelength range. This distinction can be important for certain embodiments, because materials that are regarded as opaque in the visible region might not be opaque in the near-infrared region, and vice-versa. Also, mechanical/geometric features of a surface will change the reflective properties of a material regardless of its color.

Figure 35A:
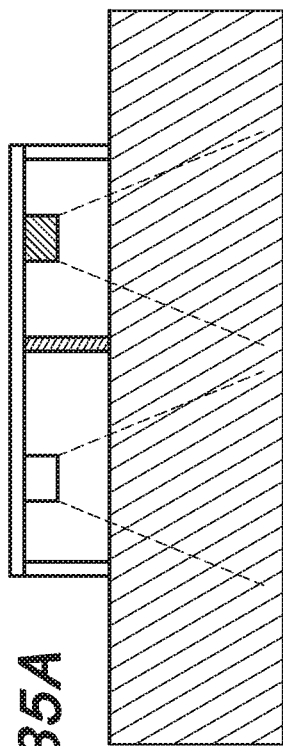
Figure 35B:
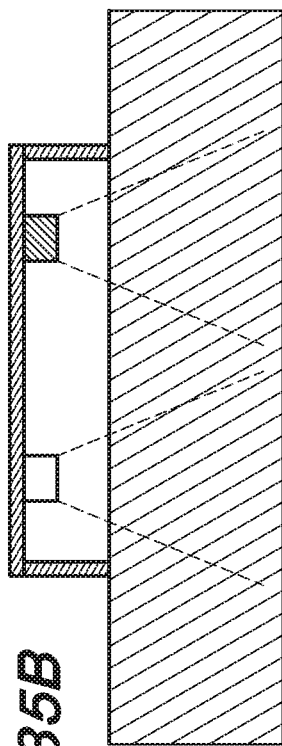
Figure 35C:
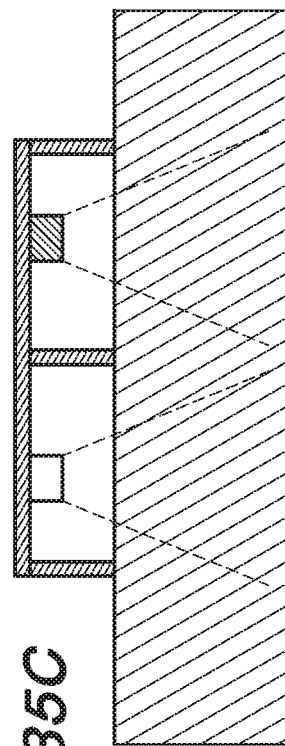
Figure 35D:
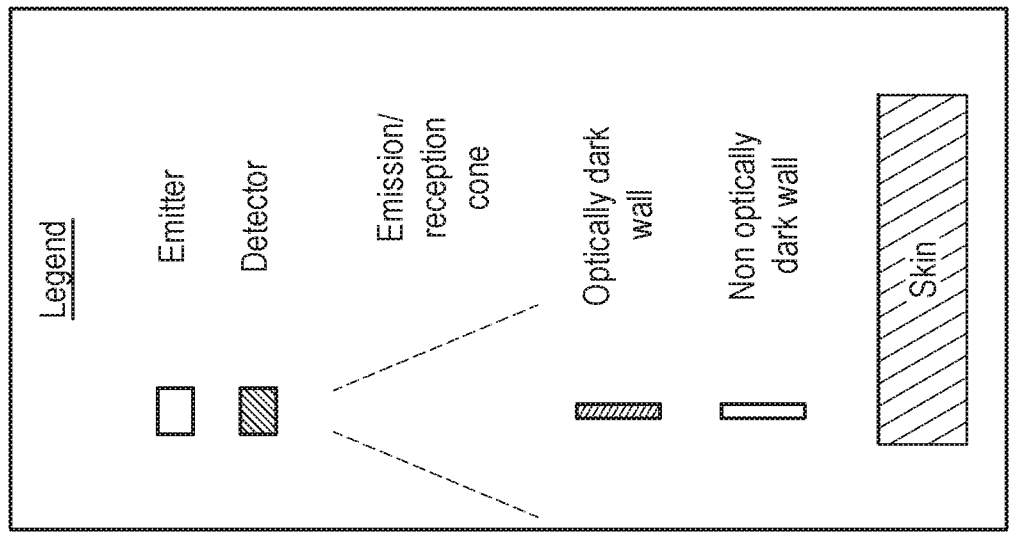

FIGS. 35A-C show some of the many configurations of a multi-chip package with optical emitter(s) and detector(s) inside optical cavities. Their components are defined in FIG. 35D. In various embodiments, the optical cavity can be filled with a material with optical refractive index closer to the skin in order to improve the sensor-skin optical coupling. In FIG. 35A, there are two optical cavities, one for the emitter and one for the detector, with walls that reflects light in order to improve sensor efficiency. Light piping is minimized by introducing an optically dark wall that minimizes the light transmitted directly from the recessed emitter to the recessed detector given their reception/emission cone. In FIG. 35B, the same functionality can be accomplished with a single cavity by making its walls optically dark. Another configuration is shown in FIG. 35C where two cavities have their walls optically dark, which offer improved performance in terms of reduced light piping figures. A drawback in the configurations shown in FIGS. 35B-C is the required relative higher LED power levels. However, they enable a reduced distance between emitter and detector for light-piping figures comparable to the configuration in FIG. 35A. This, in turn, reduces the required LED power levels given the exponential nature of light attenuation between emitter and detector as a function of the distance (emitter-detector separation). The configuration in FIG. 35C is similar to the one found in the multi chip package SFH7050 OSRAM Opto Semiconductors previously described.

The optimal emitter-detector separation and applied pressure range by means of a bandage can be estimated by solving a Photon diffusion problem with boundaries conditions represented by 3D Boltzmann Transport Equations. Finite-element and finite-difference methods can be used to numerically solve the problem for various scenarios and conditions. In the case of the sensor shown in FIGS. 17A-B with LEDs turned on shown in FIG. 18F, the optimal emitter-detector separation preferably is between 2.5 to 7 mm. The SFH7050 component preferably has a detector separation of approximately 3 mm and thus is suitable for preferred embodiments of the invention. Pressure ranges created by conventional adhesive bandages preferably are enough to prevent light piping from occurring as well as to substantially increase the photoplethysmograph amplitudes by improving significantly the optical compliance and coupling between the sensor and the patient's skin.

FIGS. 36A-B show the typical functional relations (mapping) between perfusion (perfusion index) measured by a conventional transmissive oximeter placed on a patient's finger or digit (X) and the measured perfusion of a reflective oximeter also placed on a digit (Y) as a function of the emitter-detector separation "d" depicted in FIG. 36B. Each curve (i.e., d=d0, d1, or d2) represents a different emitter-detector separation so that d2>d1>d0. In the case of the reduced emitter-detector separations adopted in these inventions, mappings (linear or nonlinear) such as the one shown in FIG. 36C ($d0^{-1}$) can be used in order to convert the measured perfusion to a displayed perfusion so as to be compatible with the perfusion measured and displayed by a conventional transmissive oximeter placed on a digit. Depending on the measurement site where the reflective pulse oximeter sensor is placed (i.e., temple, arm, leg, digit, etc.), different curves can be used in order to refine conversion between measured and displayed perfusions.

Low Manufacturing/Overhead/Maintenance Costs

In certain embodiments, the present invention may provide relatively low manufacturing costs, such as by using an integrated sensor solution. Preferably, the sensor assembly 100 may include a reduced number of components and simple encapsulation, thus enabling the use of a simple manufacturing process with reduced number of stages and very high yields. In some embodiments, the inventions can eliminate the need for patient/connection cables/or and proprietary monitors, by use of wireless communication over standard technologies (such as Bluetooth) to a computer (such as a laptop or tablet or smart phone or other device) running an app or other software that can be readily distributed via the Internet or otherwise. The preferred wireless communication in combination with a host device that can be used for processing, storage and data visualization, reduces tremendously the complexity of wireless disposable continuous pulse oximeter sensors. FIGS. 4, 6, and 27A-C through 30A-H show a sensor embodiment with reduced number of components and assemblies. The PCB board 2901 preferably has only 3 small integrated circuits, a multi chip optical sensor package, a SMD antenna, two crystal oscillators, an inductor, and little over 20 passive components including resistors and capacitors. The integrated circuits preferably are a low-cost low-power fixed point ARM processor with Bluetooth Low Energy (BLE) radio from Nordic, NRF51422, a low-cost low-power pulse oximeter frontend from Texas Instruments, AFE4403, and a low-cost high-efficiency boost converter from Texas Instruments, TPS61220. The other components required to assemble the full sensor preferably are a lithium manganese dioxide battery 2902, and a set of 3 adhesive tapes 2903, 2904, 2905 as shown in FIG. 29, totaling 5 component assemblies if we consider the assembled PCB board 2901 (FIG. 29) as a single component assembly. Given its simplicity, it is expected that the total manufacturing cost of a wireless disposable continuous pulse oximeter sensor unit with the above description may be comparable to the total manufacturing cost of conventional wired disposable oximeter sensors, especially on scales of production for 1 million or more sensor units manufactured yearly. Given its preferred relatively small footprint, the inventions can be packaged and used in a wide variety of useful situations and applications.

Preferably, the inventions are practiced in embodiments that reduce their power consumption. For example, regarding "continuous" pulse oximeter monitoring, according to the Nyquist-Shannon sampling theorem, one can define the lowest sampling frequency for a parameter trend as a number strictly greater than twice the highest frequency component of the parameter trend. Thus, under that theorem, if a parameter trend has spectral content of interest with no frequencies higher than F Hertz, then the said trend can be completely recovered by a series of measurements that are spaced by no more than the 1/(2F) seconds. In this way, the same information conveyed by a "continuous" trend can be provided by its sampled trend counterpart provided that the sampling obeys the Nyquist-Shannon sampling theorem. Such approximation of continuous parameter trends by sampled ones allows the sensor to save power since its hardware can be partially or totally turned off between measurements. It also reduces the wireless bandwidth required to transmit the said trends, which in turn not only reduces consumed power, but also enables for the same radio power levels a longer sensor-to-host distance.

Monitor Agnostic

Preferably, and as indicated above, the present invention may be used with a wide variety of monitors. In a preferred embodiment, a wireless connection between the sensor and a host device (e.g., monitor), combined with portable algorithms for processing, displaying, etc. the measurements of SpO2, PR and PI, may enable the use of several types of monitors (e.g., smartphones, tablets, desktop and laptop computers, bedside monitors, etc.) with the sensor assembly 100. This feature may give a healthcare provider the freedom and flexibility to choose the monitoring solution that best fits their needs in terms of cost and functionality and immediate circumstances of the patient, among other factors.

Referring further now to the drawings, FIG. 1 shows a block diagram for a disposable, wireless pulse oximeter sensor 100, according to a preferred embodiment of the invention. As shown in the figure, the sensor 100 includes a main processor 102, such as the ARM Cortex M0 processor from Nordic Semiconductors. The processor may control a low energy radio 103, through a Bluetooth connection, for example. The sensor 100 may be wirelessly connected 104 to a host device 105 such as, but not limited to, a laptop computer, desktop computer, smart tablet, smart phone, smart watch, wireless appliance, etc. In a preferred embodiment of the invention, a cloud connection 106 may connect to the host device 105 for storage, processing, and visualization of the data. In alternative embodiments (not shown), the sensor 100 itself may connect to the cloud, without the intermediate application software and/or hardware and/or steps of a host device 105. The Internet Protocol Support Profile (IPSP) from the Bluetooth SIG and 6LoWPAN technology from the Internet Engineering Task Force (IETF), for instance, can be used to enable the sensor 100 with radio 103 to communicate with the Internet and cloud servers as well as other wireless sensors directly.

Referring back to the pulse oximeter sensor 100 components, the sensor 100 may include an integrated circuit 107, such as Texas Instruments' AFE4403, comprising a photodiode frontend, LED drivers, and control logic. Further, a DC-DC boost converter 108 may preferably power the LED driver circuit. Preferably, the sensor 100 may be powered by a disposable, long-lasting battery 109 such as a lithium manganese dioxide battery. An optical sensor 110 may include red and near-infrared LEDs and silicon photodiodes, such as the multi-chip package sensor SFH7050 available from OSRAM. Persons of ordinary skill in the art will understand that the number of chips for the optical sensor for any given embodiment of the inventions can be selected depending on costs and other factors. Red and near-infrared LEDs 113 and a silicon photodiode 114 may direct light onto a patient's measurement site such as a fingertip 111. Preferably, a single-use ON switch 112 may be made from conductive adhesive copper foil tape.

Figure 2G:
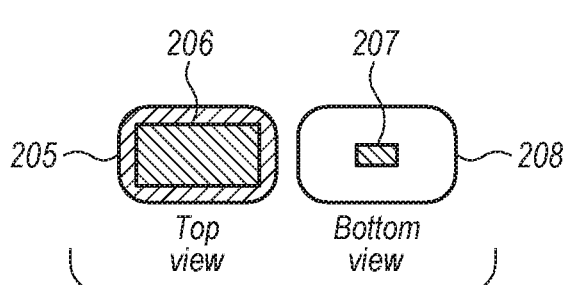
FIG. 2G is a wireless, disposable, continuous pulse oximeter sensor with adhesive tape layout similar to a patch (with small adhesion area required), according to an embodiment of the inventions.
Figure 2H:
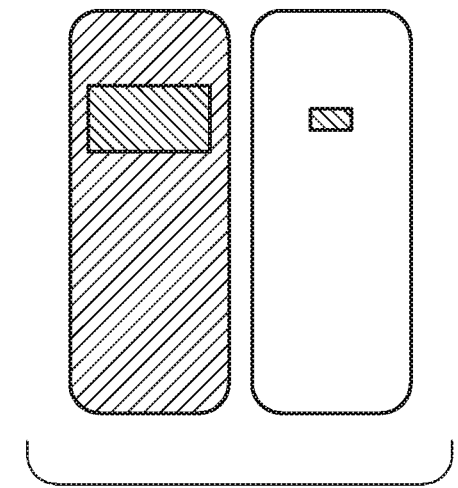

FIG. 2A shows some of the many alternative embodiments of wireless, disposable, continuous pulse oximeter sensors attached to a patient's digit. In the figure, each pulse oximeter sensor uses a different adhesive tape layout, such as those depicted in FIGS. 2G and 2H, respectively. Specifically, pulse oximeter 203 is attached to a patient's fingertip 202 using a flat adhesive bandage 205 encapsulated in a PTFE pocket 206, as shown in FIG. 2G. A sensor 207 on the underside 208 of the pulse oximeter 203 may contact the patient's skin when the underside 208 is adhered to the patient's skin. In some of the many alternative embodiments of the inventions such as those shown in FIGS. 2H through 2L, an adhesive bandage or tape 204 may be used to attach the pulse oximeter 203 to a patient's digit, or other measurement site.

The pulse oximeter of the present invention may be attached to any one or more of a range of suitable alternative measurement sites, including without limitation a patient's temple (FIG. 2B), forehead (FIG. 2C), neck (FIG. 2D), and/or wrist (FIGS. 2E and 2F).

Figure 3:
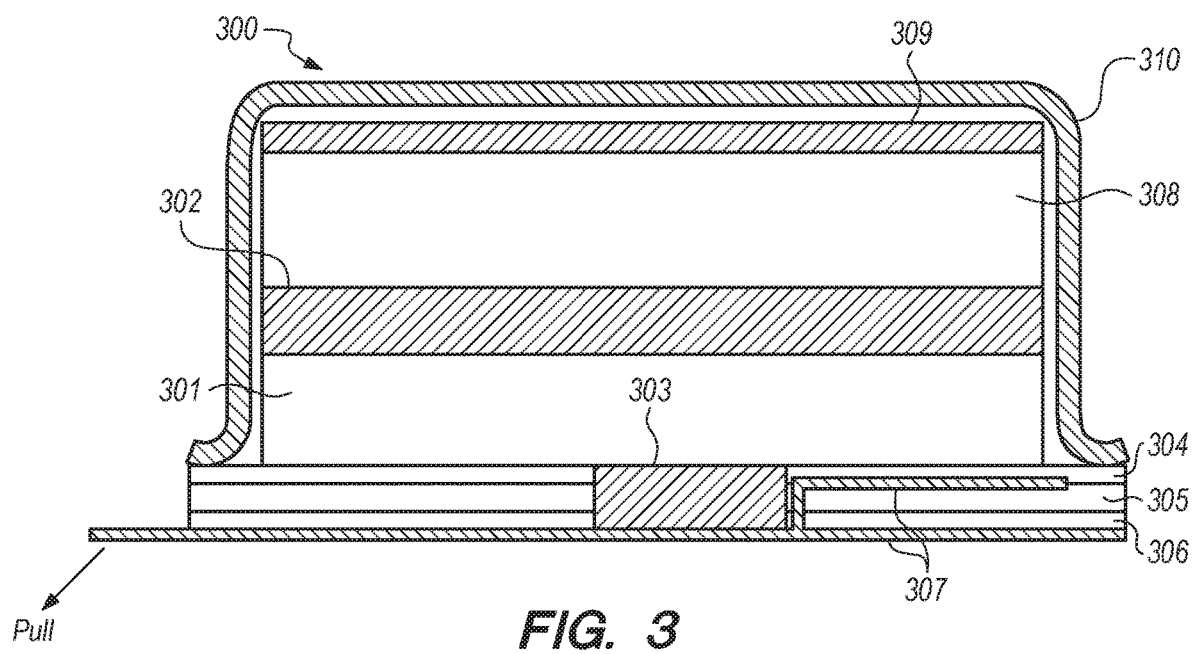
FIG. 3 is a cross-section view of a wireless, disposable, continuous pulse oximeter sensor (with adhesive tape layout as depicted in FIG. 2G), according to one of the many embodiments of the inventions.

In FIG. 3, a pulse oximeter similar to the one shown in FIG. 2G is shown in a cross-section view, depicting one of the many ways of fabricating a stack-up of the various components of a wireless, disposable, continuous pulse oximeter 300. A PTFE encapsulation pocket 310 may house the components of the pulse oximeter 300. From top-down, the pulse oximeter may include: an antenna 309, a battery 308, a printed circuit board (PCB) 301 and PCB components 302, and an optical sensor 303. For attachment to a patient's measurement site such as a fingertip, the pulse oximeter 300 may include PCB-to-skin adhesive layer and multiple biocompatible adhesive layers 305, 306. A release liner 307 may be disposed between the adhesive layers 304, 305, 306 such that when the release liner is pulled, it exposes the optical sensor 303 and the adhesive layers 304, 305, 306 for attachment to a patient's measurement site.

FIG. 4 shows an example of one of the many suitable frontend circuit schematics of a wireless, disposable, continuous pulse oximeter sensor, according to an embodiment of the invention. The pulse oximeter sensor may include an integrated circuit 402 such as the AFE4403, or the AFE4490 circuits available by Texas Instruments, including a photodiode frontend, LED drivers, and control logic. An optical sensor 403 such as the SFH7050 sensor available by OSRAM, may include red and near-infrared LEDs and silicon photodiode.

Figures 1, 5:
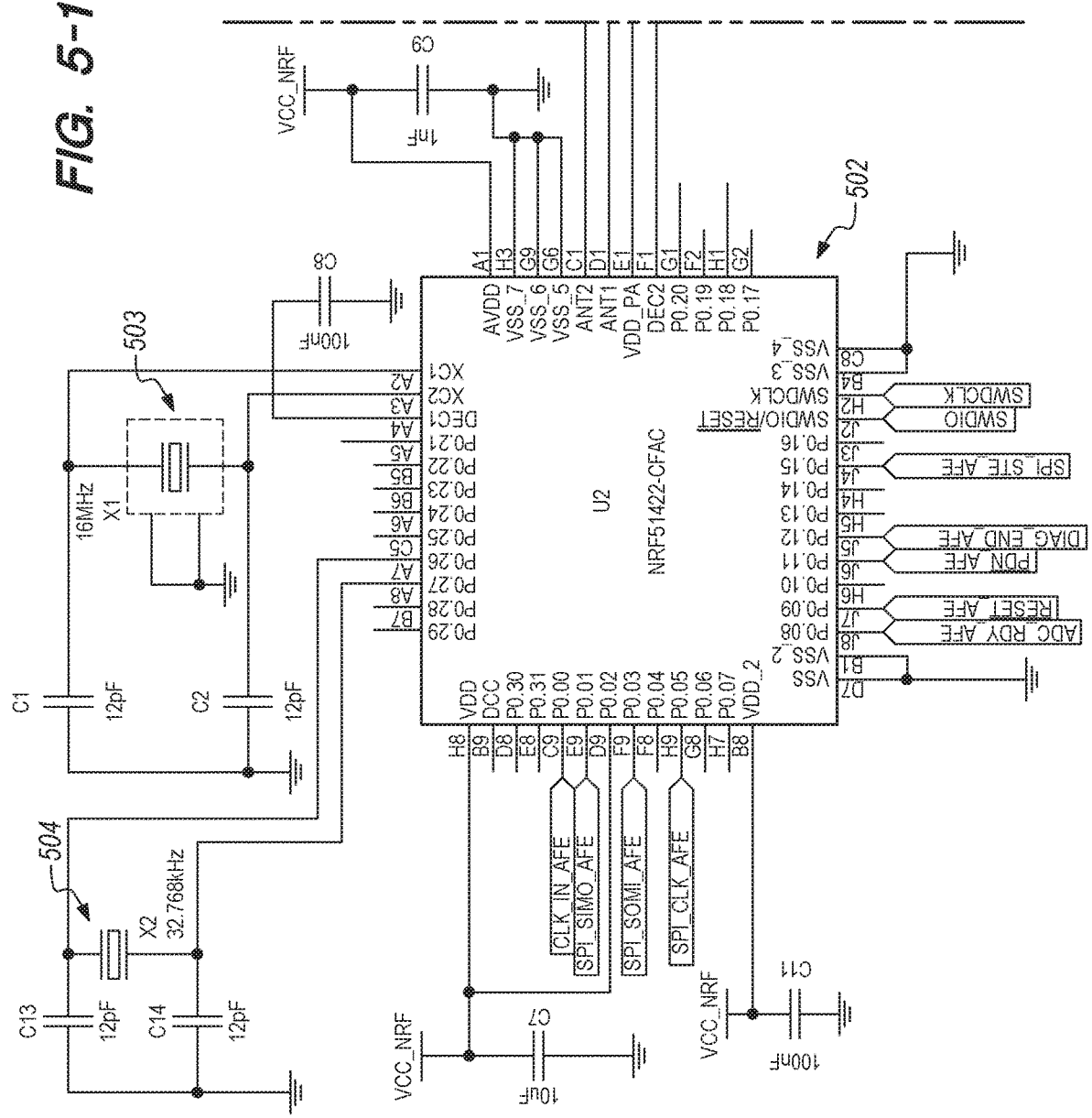
FIG. 5 shows a signal processing unit and antenna circuit schematic of a wireless, disposable, continuous pulse oximeter sensor, in accordance with an embodiment of the inventions.
Figures 2, 5:
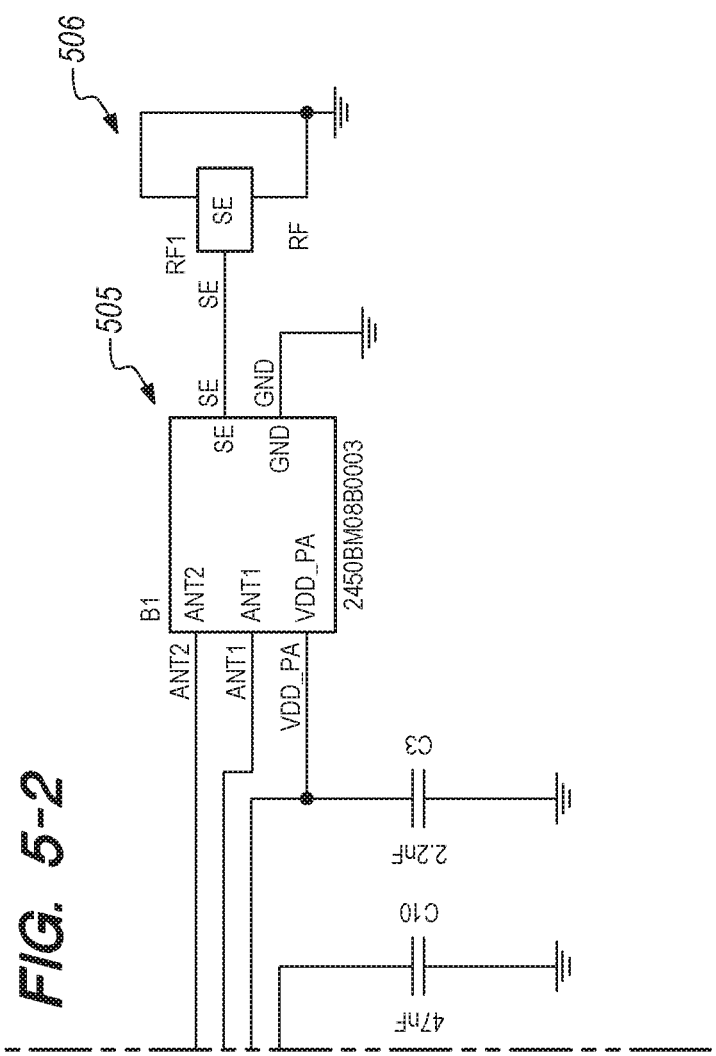

FIG. 5 shows a signal processing unit and antenna circuit schematic of a wireless, disposable, continuous pulse oximeter sensor, according to an embodiment of the invention. The pulse oximeter may include a main processor 502 such as the ARM Cortex M0 processor available from Nordic Semiconductors. Further, the pulse oximeter may include a 16 MHz crystal oscillator 503, a 32.768 kHz crystal oscillator 504, a 2.45 GHz impedance balloon filter (single to differential) 505, and antenna feed 506.

Figure 6:
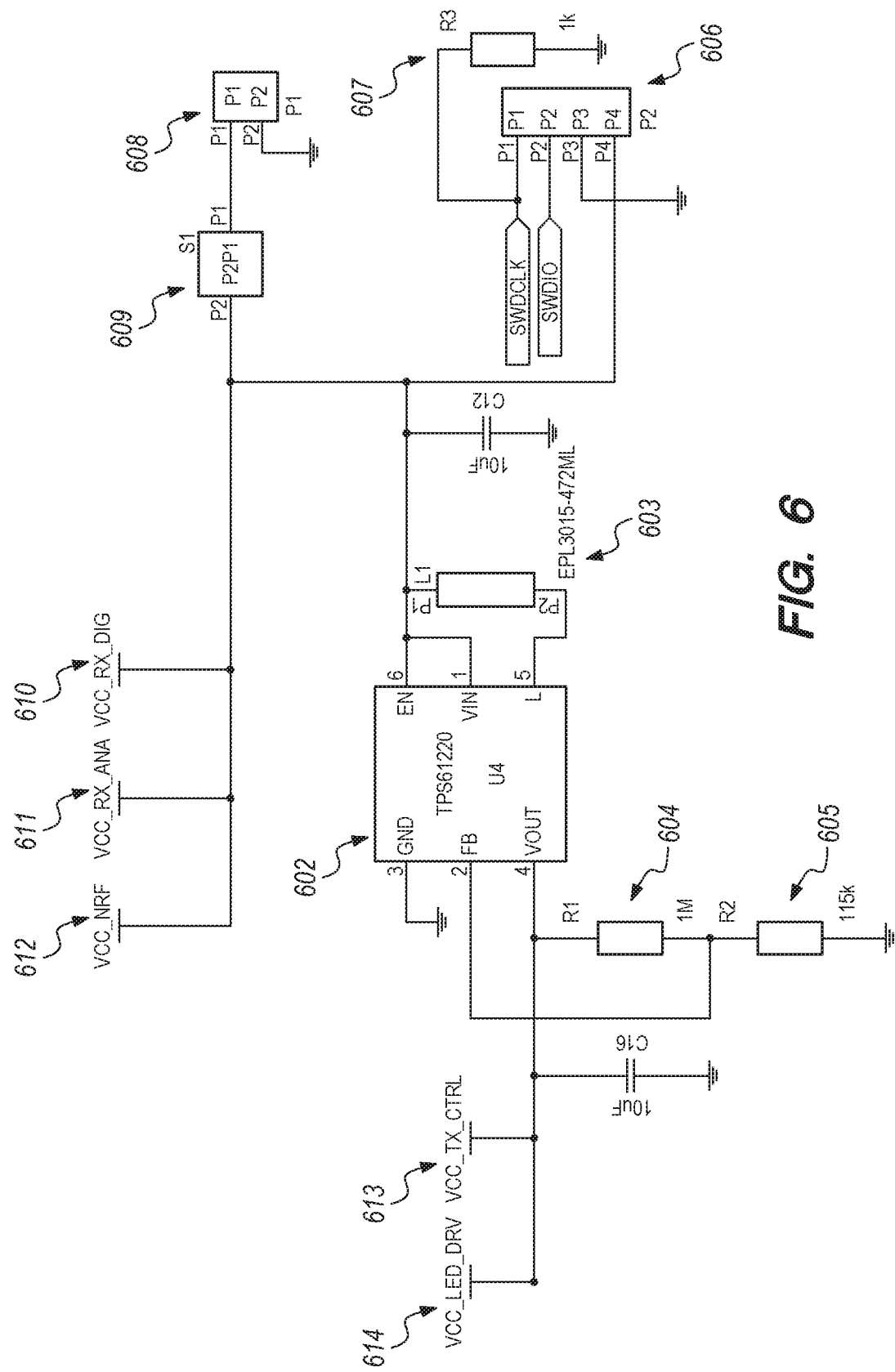
FIG. 6 shows a power management circuit schematic of a wireless, disposable, continuous pulse oximeter sensor, in accordance with an embodiment of the inventions.

FIG. 6 shows a power management circuit schematic of a wireless, disposable, continuous pulse oximeter sensor, according to an embodiment of the invention. Preferably, the power management circuit of the pulse oximeter may include: a boost convertor 602 such as TPS61220 from Texas Instruments, a ferrite inductor 603, boost converter voltage setting resistors 604, 605, debug pads 606 for the main processor, noise rejection pull down resistor 607, battery voltage terminals 608, ON switch pads (single use) 609, and voltages for the main processor and integrated circuit 610, 611, 612, 613, 614.

FIGS. 7A-D depict printed circuit board layers of a disposable, wireless pulse oximeter sensor, including: antenna feed 701, main processor 702, integrated circuit 703, boost converter 704, crystal oscillators 705, 706, ferrite inductor 707, battery voltage terminals 708, ON switch pad 709, debug pads 710 for main processor 702, optical sensor 711, and antenna "keep out" areas 712, 713.

FIGS. 8A-B, 9A-B, and 10A-B show a 3-part adhesive tape design, according to some of the many various embodiments of the present invention. As mentioned above, persons of ordinary skill in the art will understand that the dimensions and shapes shown in these and other drawings are not intended to be delimiting of the many different embodiments in which the inventions can be practiced. Instead, the dimensions and shapes are only intended to be illustrative of one of the many ways in which the inventions may be practiced.

Figures 8A, 8B:
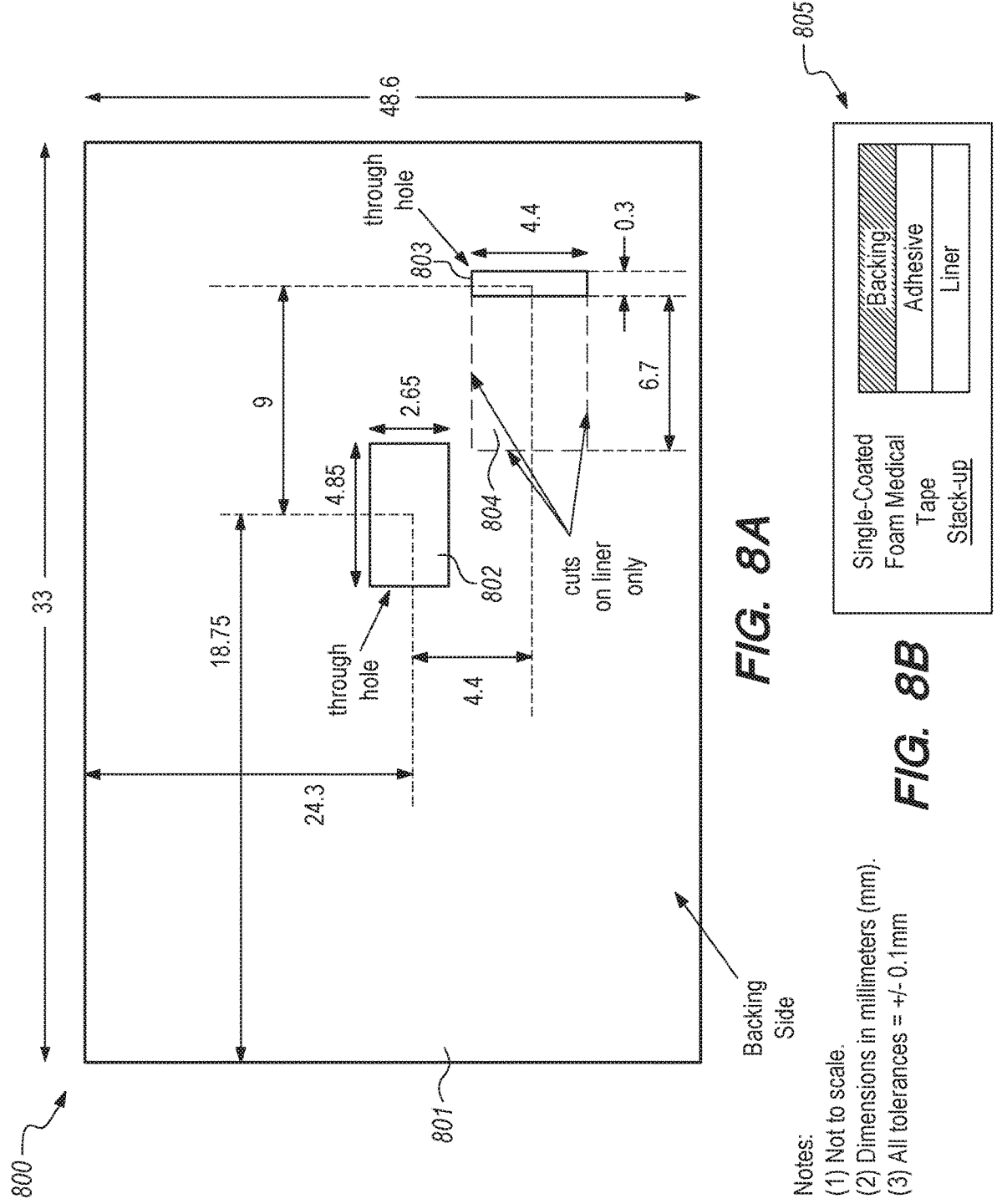

FIG. 8A shows an encapsulation tape design, and FIG. 8B shows the corresponding tape stack-up. As shown in the figures, an encapsulated tape design may include a single coated foam medical tape 800 with a biocompatible foam backing 801. A window 802 and through hole 803 may be cut out of the encapsulation tape 800. The liner may include cuts 804 which do not extend through to the adhesive tape layers in order to facilitate the attachment of tab 900 to the encapsulation tape 800.

FIG. 9A shows a tape design that enables the circuit board to be "turned on" or activated by the clinician or user at the time of use, and FIG. 9B shows the corresponding tape stack-up. In a preferred embodiment, the present invention includes a tab 900 comprising a copper foil 901 and conductive adhesive which are used to activate an ON switch. A release liner 902 may be gripped by the clinician and/or user and peeled back via tab 900, thereby exposing the conductive adhesive shown in 904 and completing and activating the circuit (and the battery power to the sensor 110 and other components of the sensor assembly 100). Thus, preferably the clinician or user at the time of use pulls tab 900 in order to activate the sensor assembly 100. Persons of ordinary skill in the art will understand that any of a wide range of suitable switches can be fabricated and/or used to practice the inventions.

For the assembly 100 to work in its preferred manner, it must be positioned and held in contact on the patient's skin 111. An example of one of the many ways in which this can be accomplished is illustrated in FIG. 10A, which shows a tape design that enables skin-to-device adhesion. A corresponding stack-up is shown in FIG. 10B. As shown in the figures, a double coated biocompatible tape 1000 may be provided and include: a first liner layer 1001, a first adhesive layer, a carrier layer, a second adhesive layer, and a second releasable liner layer 1002.

Figure 11:
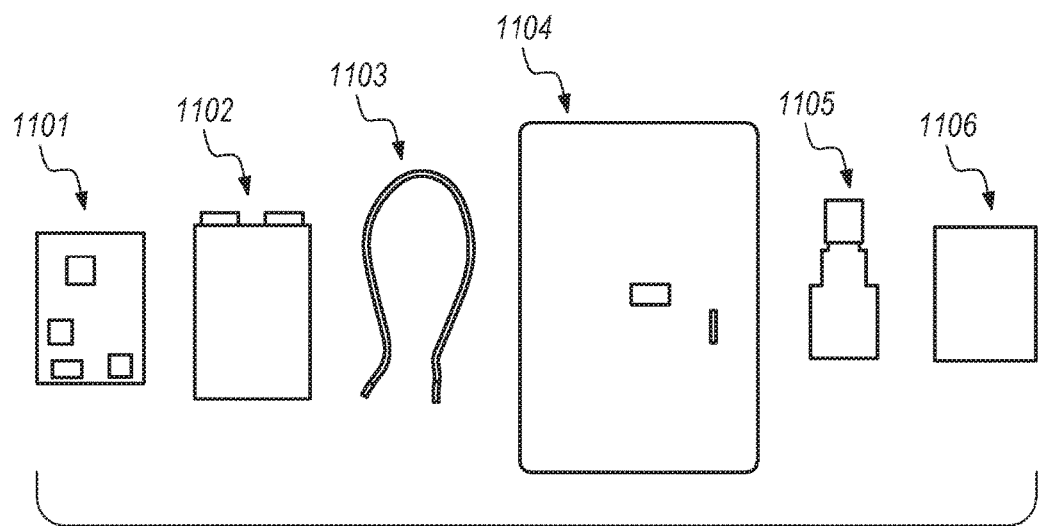
FIG. 11 shows an exploded view of a wireless, disposable, continuous pulse oximeter sensor, in accordance with an embodiment of the inventions. As illustrated, FIG. 11 includes embodiments of the apparatus shown in FIGS. 8 (element 1104), 9 (element 1105), and 10 (element 1106) above.

FIG. 11 shows an exploded view of a disposable, wireless pulse oximeter, according to an embodiment of the inventions. Persons of ordinary skill in the art will understand that certain components in FIG. 11 correspond to those discussed above. Preferably, the present inventions include a printed circuit board (PCB) 1101, a disposable, lithium manganese dioxide battery 1102, a wired loop antenna 1103, an encapsulated adhesive tape 1104, a conductive adhesive tape assembly 1105, and double-layer adhesive tape assembly 1106.

Figure 12:
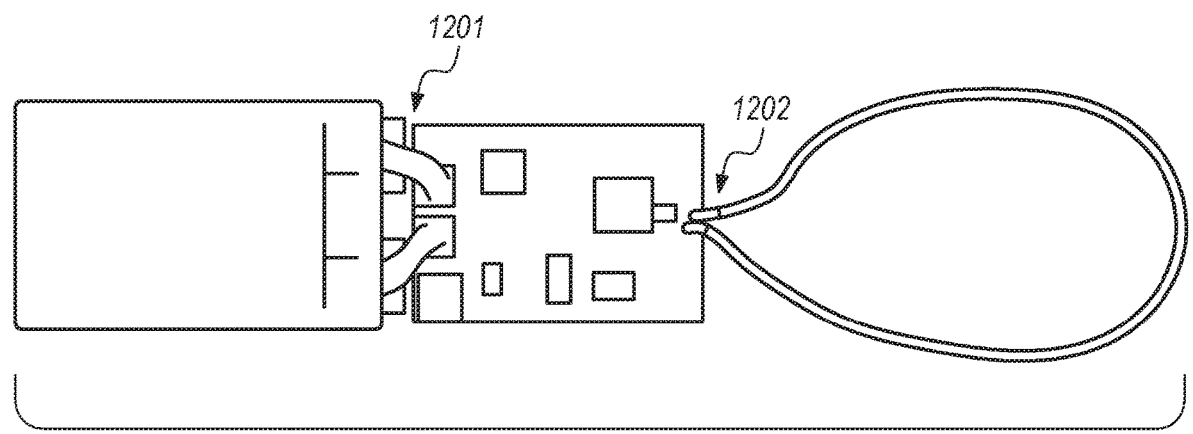
FIG. 12 shows a loop antenna (such as element 1103 from FIG. 11) and battery soldered to a pulse oximeter printed circuit board (PCB), in accordance with an embodiment of the inventions.
Figure 13A:
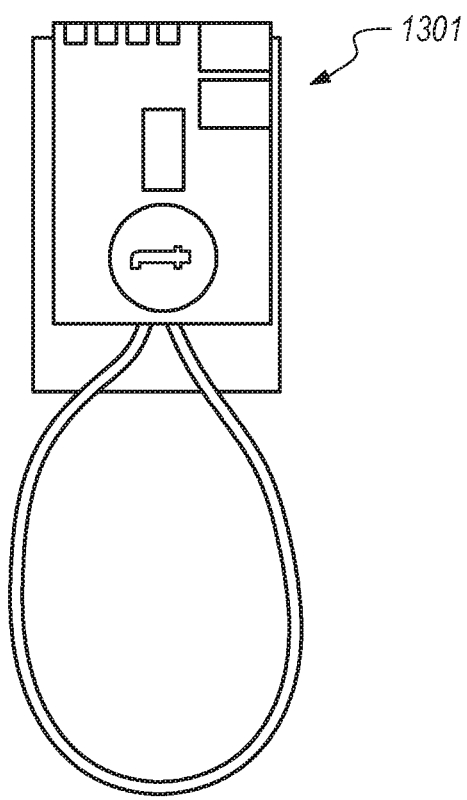
FIGS. 13A-B are similar to FIG. 12, but show a battery and antenna being folded onto a PCB to give shape to the pulse oximeter-PCB assembly, in accordance with an embodiment of the inventions.
Figure 13B:
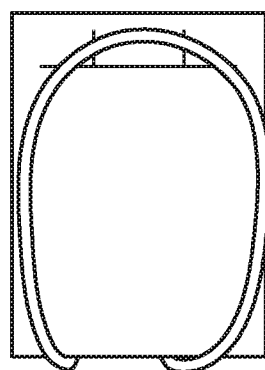
Figure 14A:
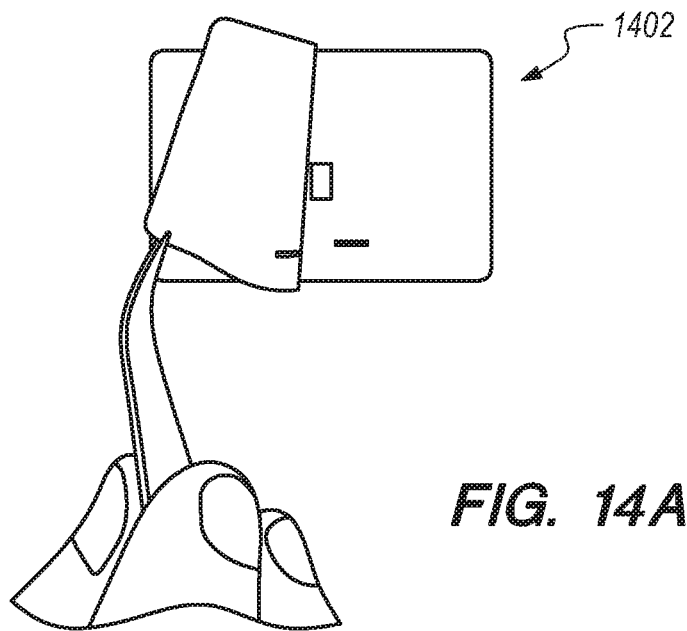
FIGS. 14A-D show the adhesive tape from FIGS. 9A-B being attached to the adhesive tape depicted in FIGS. 8A-B, in accordance with an embodiment of the inventions.
Figure 14B:
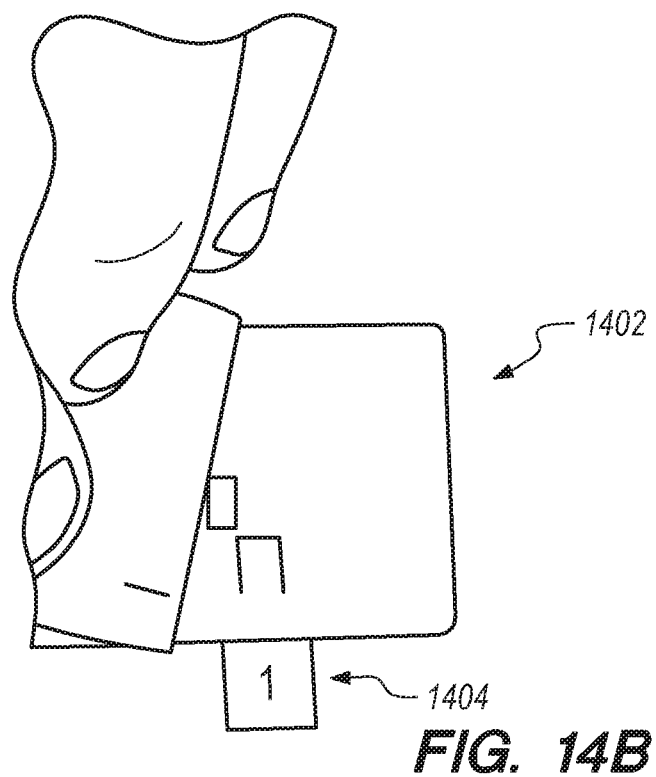
Figure 14C:
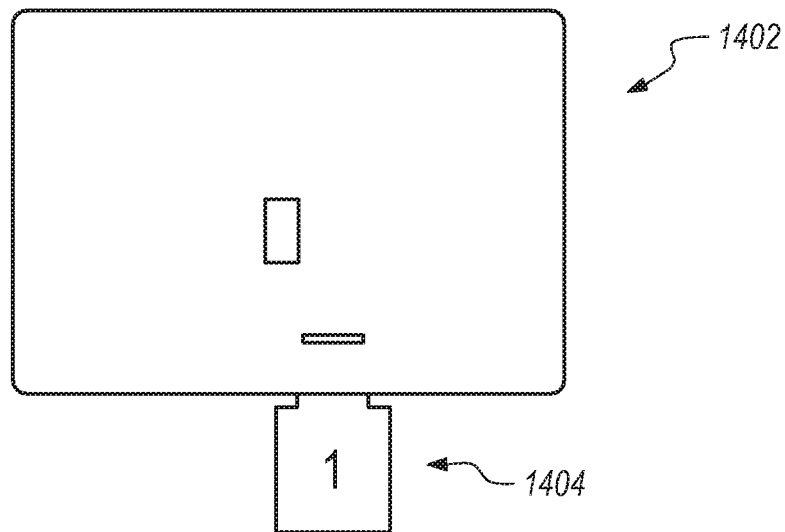
Figure 14D:
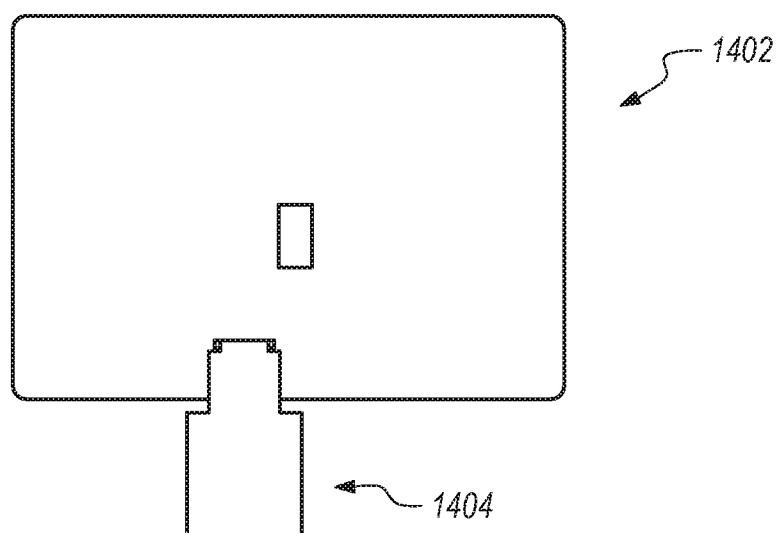
Figure 15A:
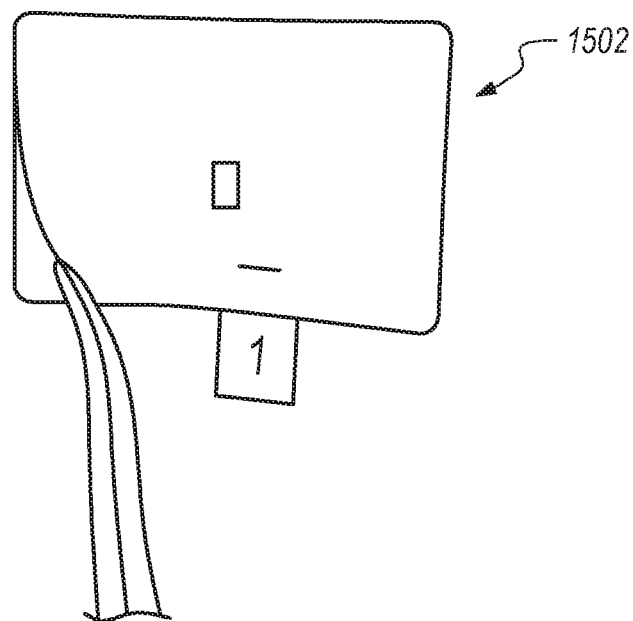
FIGS. 15A-J depict one of the preferred embodiment of steps for attaching an adhesive tape assembly from FIGS. 14A-D to a pulse oximeter assembly PCB assembly from FIGS. 13A-B, in accordance with an embodiment of the inventions.
Figure 15B:
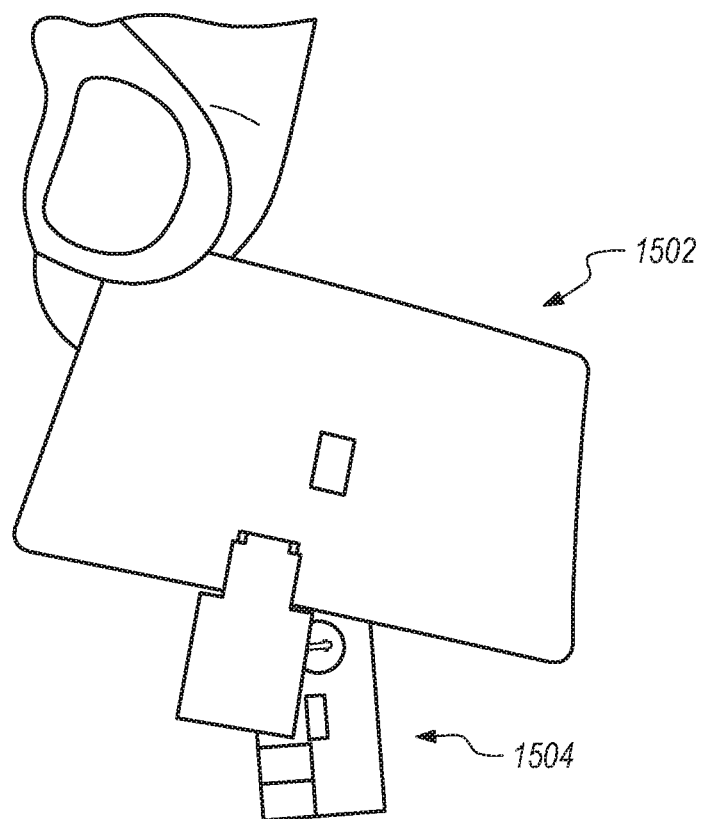
Figure 15C:
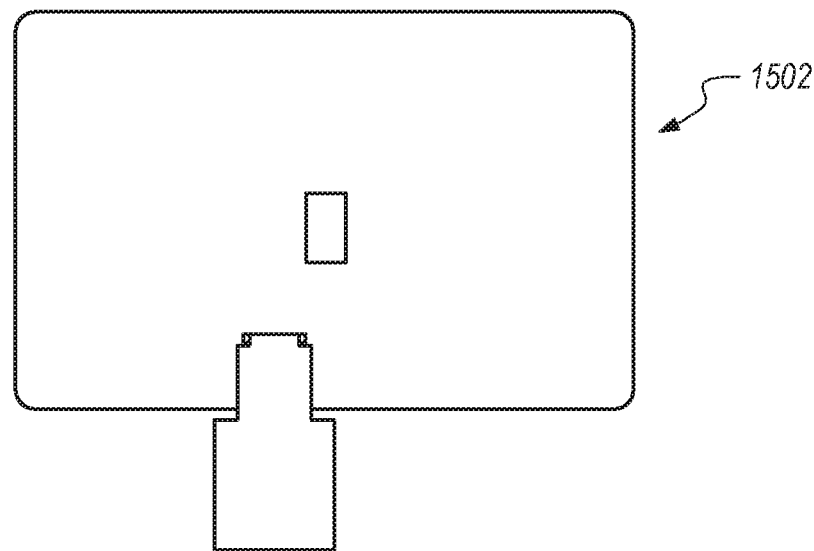
Figure 15D:
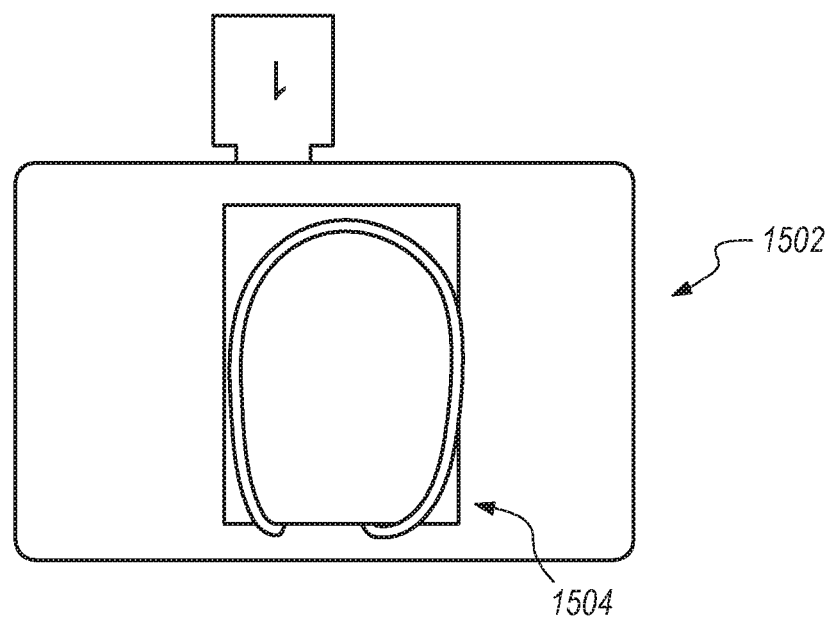
Figure 15E:
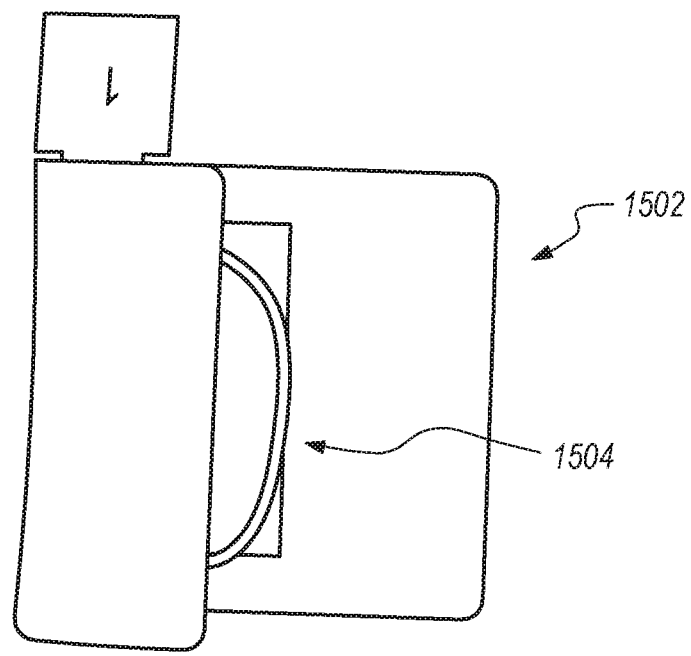
Figure 15F:
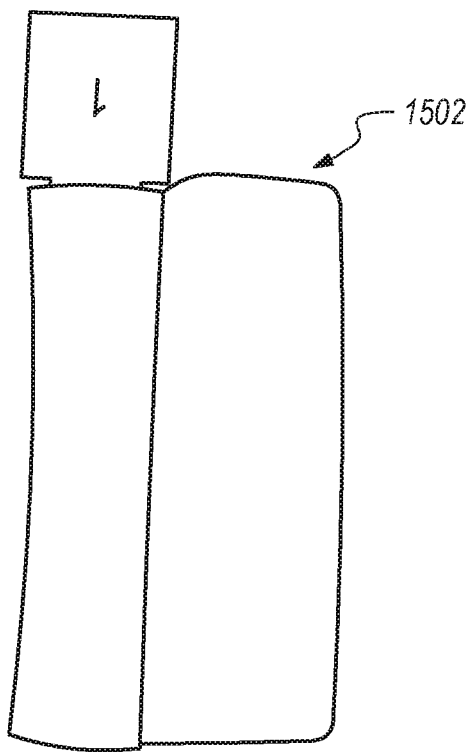
Figure 15G:
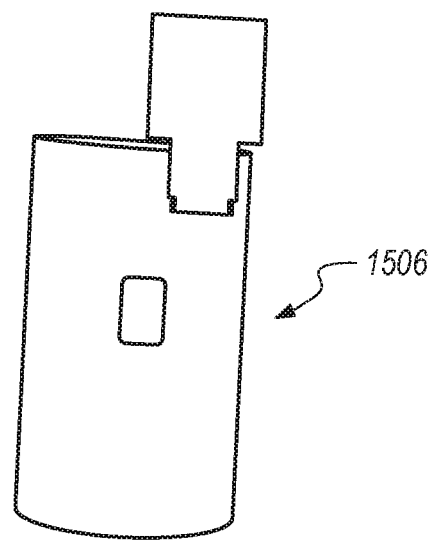
Figure 15H:
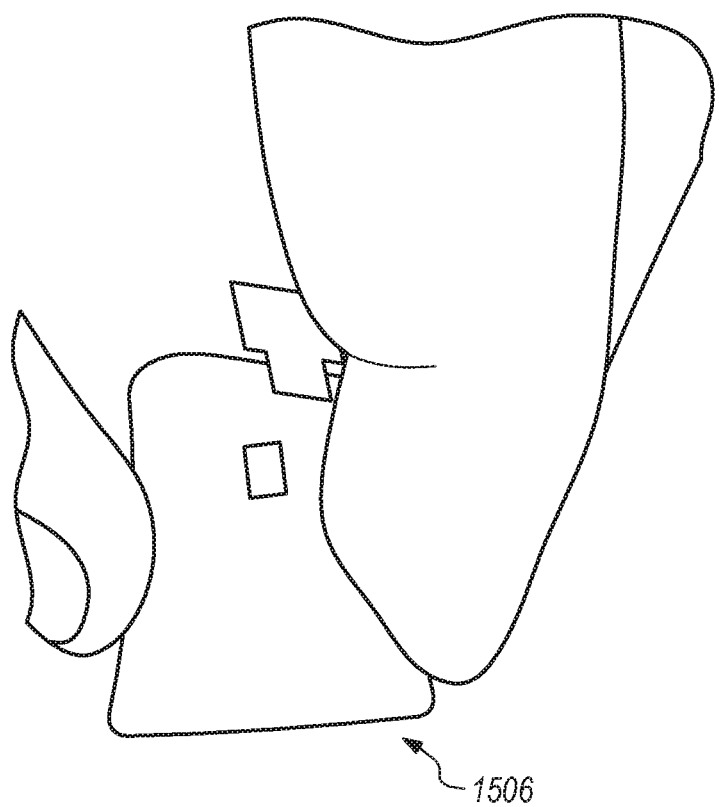
Figure 15I:
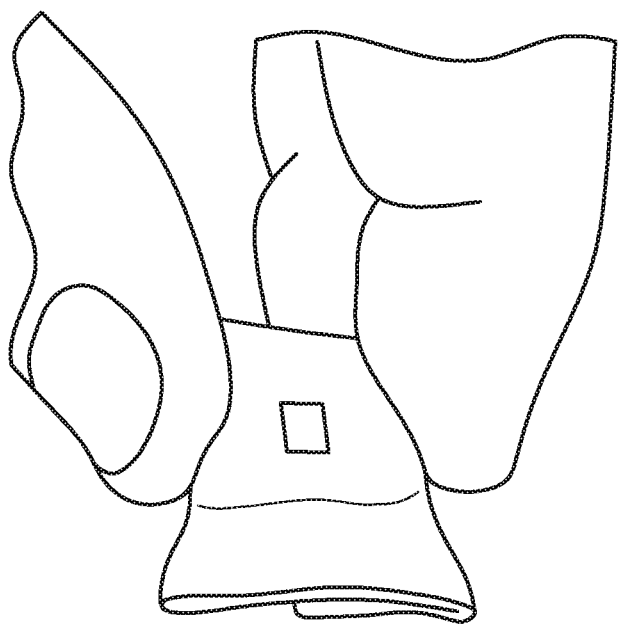
Figure 15J:
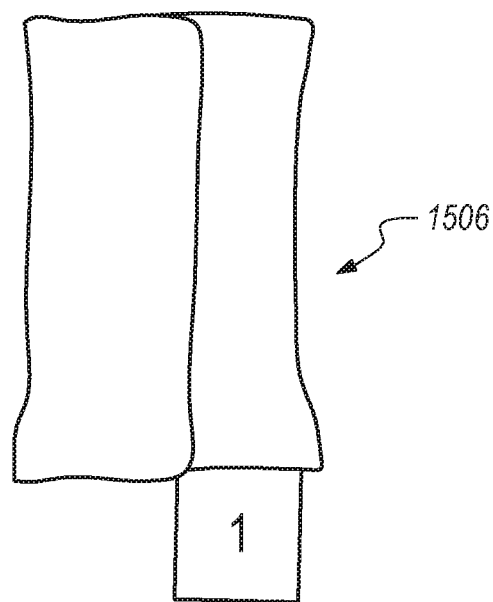

FIG. 12 shows one of the many embodiments of the ways in which the inventions can be practiced, including a loop antenna and battery soldered to a pulse oximeter printed circuit board (PCB). Related FIGS. 13A-B show one of the many embodiments of the ways in which such a battery and antenna can be folded onto a PCB to give shape to the pulse oximeter-PCB assembly 100.

Figure 17A:
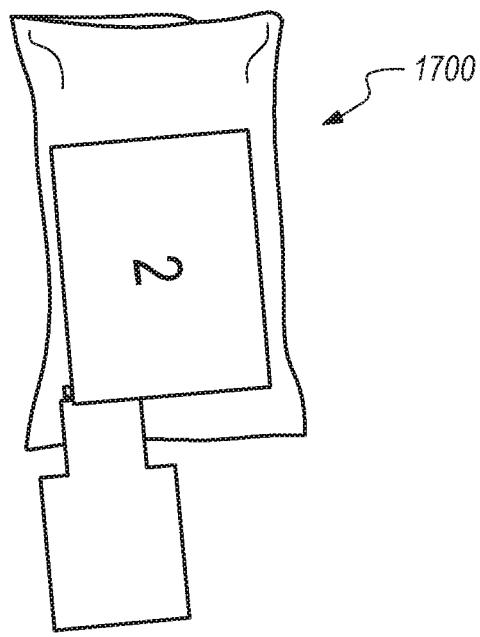
FIGS. 17A-B are a front view and a back view of a preferred embodiment of a wireless, disposable, continuous pulse oximeter sensor fully assembled, in accordance with an embodiment of the inventions.
Figure 17B:
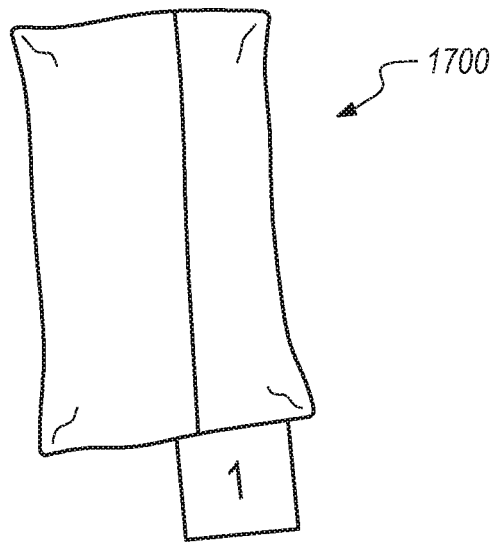
Figure 18A:
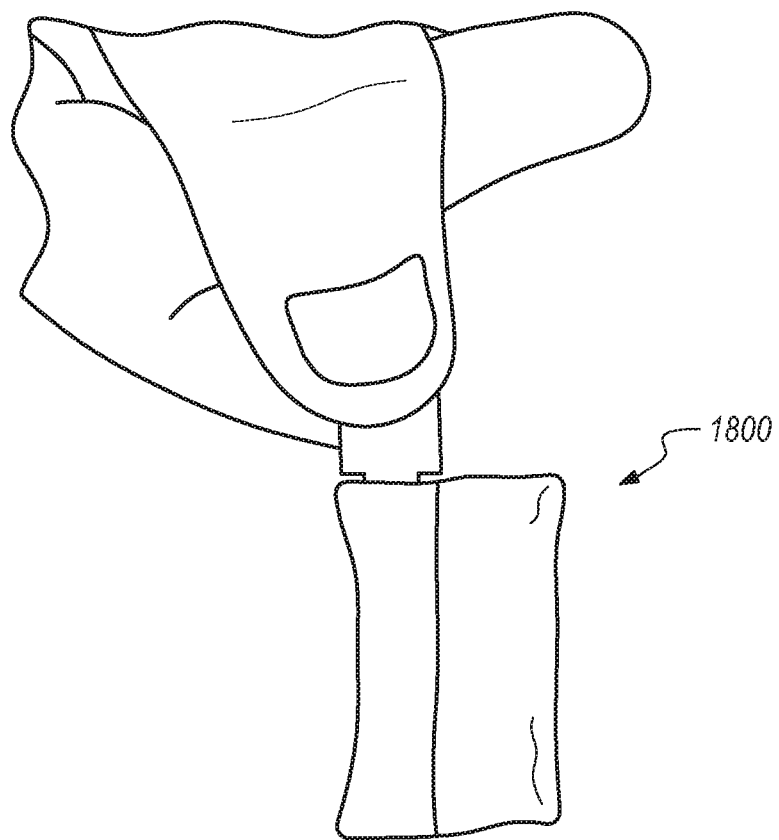
FIGS. 18A-H show one of the many embodiments of the inventions, including a series of steps to turn on and attach a wireless disposable pulse oximeter (such as shown in FIGS. 17A and 17B) to a body appendage (e.g., fingertip), in accordance with an embodiment of the inventions.
Figure 18B:
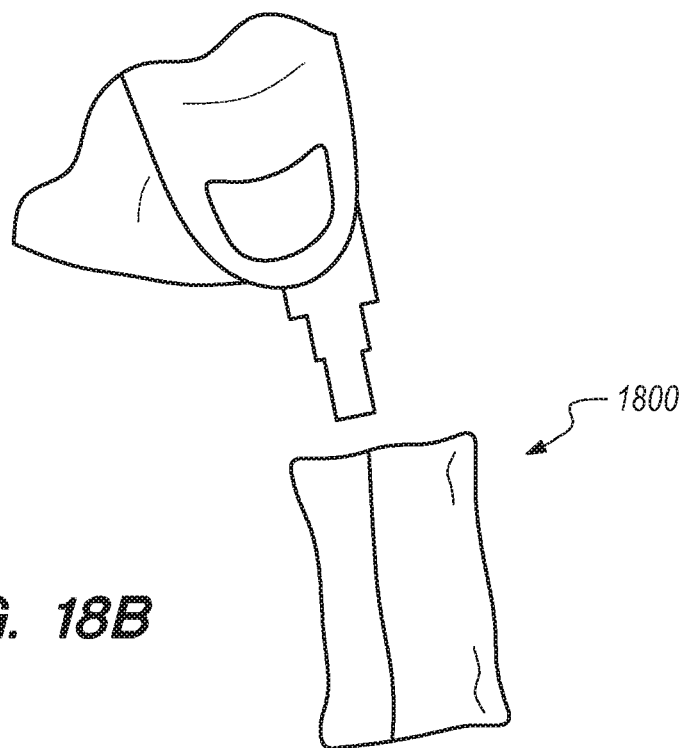
Figure 18C:
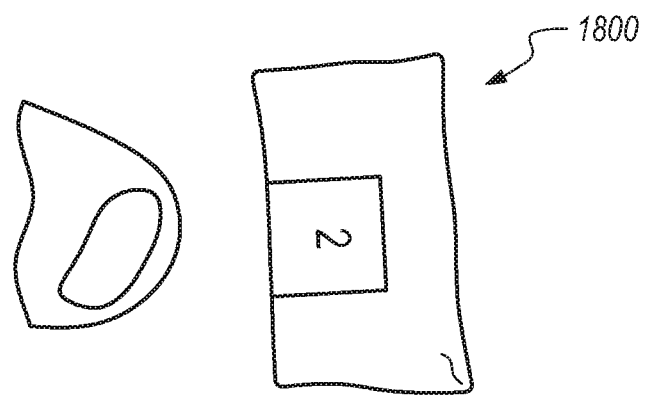
Figure 18D:
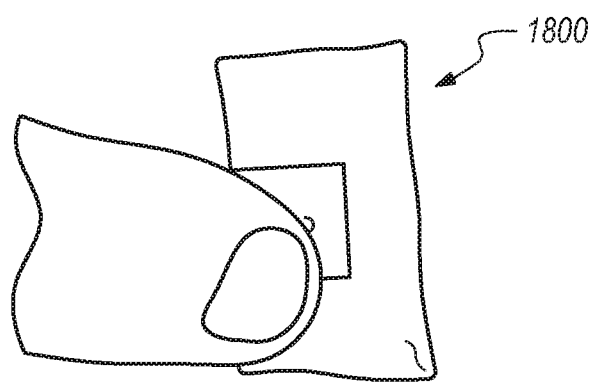
Figure 18E:
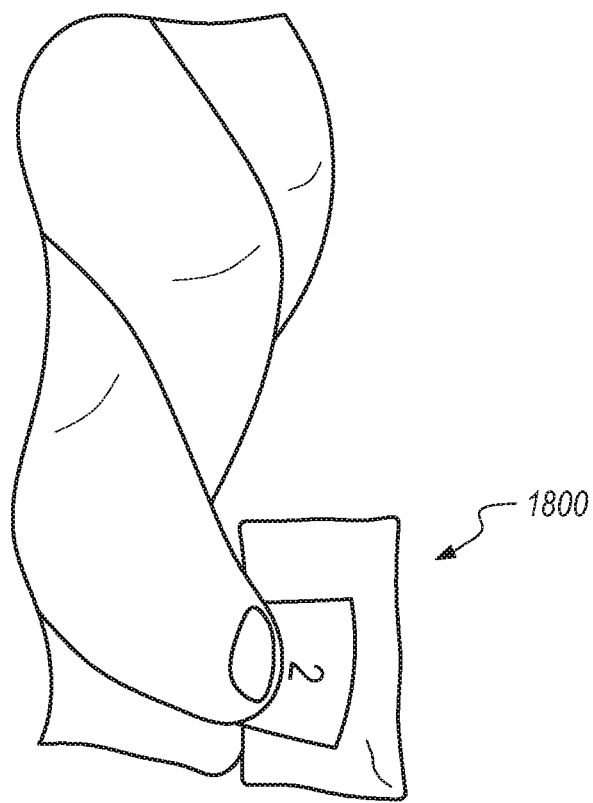
Figure 18F:
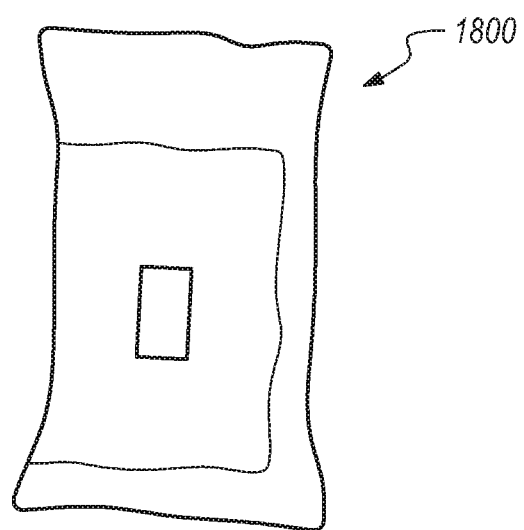
Figure 18G:
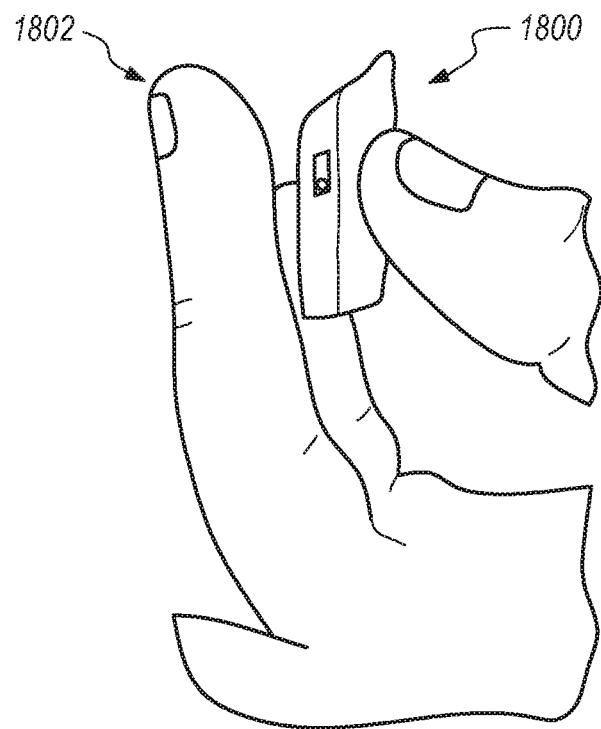
Figure 18H:
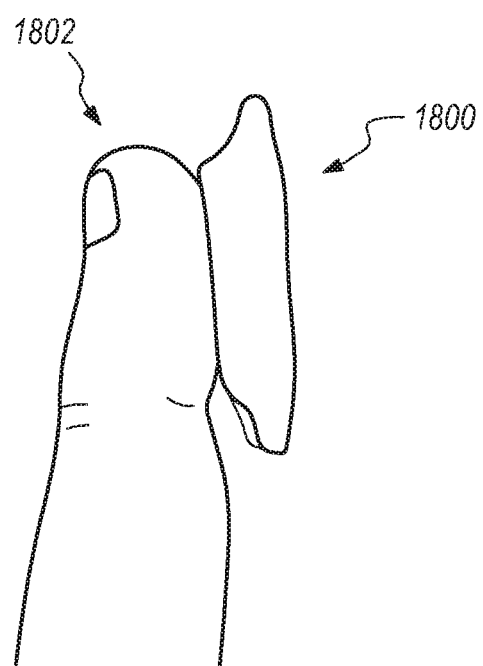

Persons of ordinary skill in the art will understand that the inventions can be fabricated and assembled in a wide variety of suitable ways. FIGS. 14-19 illustrate one of the many such ways, including by using some of the elements discussed above, to provide a compact and easy-to-use wireless, disposable, continuous pulse oximeter that preferably can be used for an extended period of monitoring physiological data from a patient. In the eventual assembly described and shown in the accompanying drawings, all that is required for end use of the sensor assembly 100 is to remove a tab "1" to activate the assembly, and then remove a tab "2" to expose an adhesive that then is pressed to the patient's skin (persons of ordinary skill in the art will understand, for example, that removing tab "1" in FIGS. 18A and 18B preferably establishes electrical contact across the copper foil and conductive adhesive 901 of FIG. 9A/9B and thereby between the corresponding terminals 1301 in the upper right of FIG. 13A, preferably activating the light on the sensor 110 as shown in FIGS. 18F and 18G.

Figure 16A:
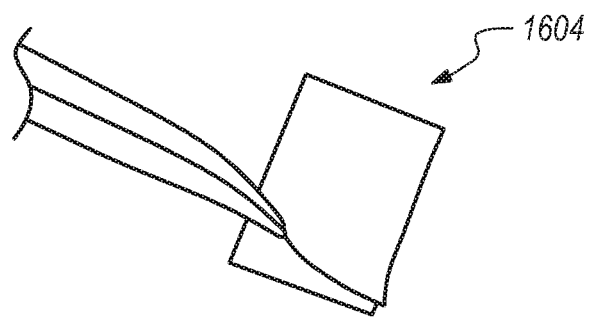
FIGS. 16A-B illustrate one of the many embodiments of apparatus and methods of attachment of the adhesive tape (such as shown in FIGS. 10A-B) to a wireless, disposable, continuous pulse oximeter assembly (such as shown in FIGS. 15A-J), in accordance with an embodiment of the inventions.
Figure 16B:
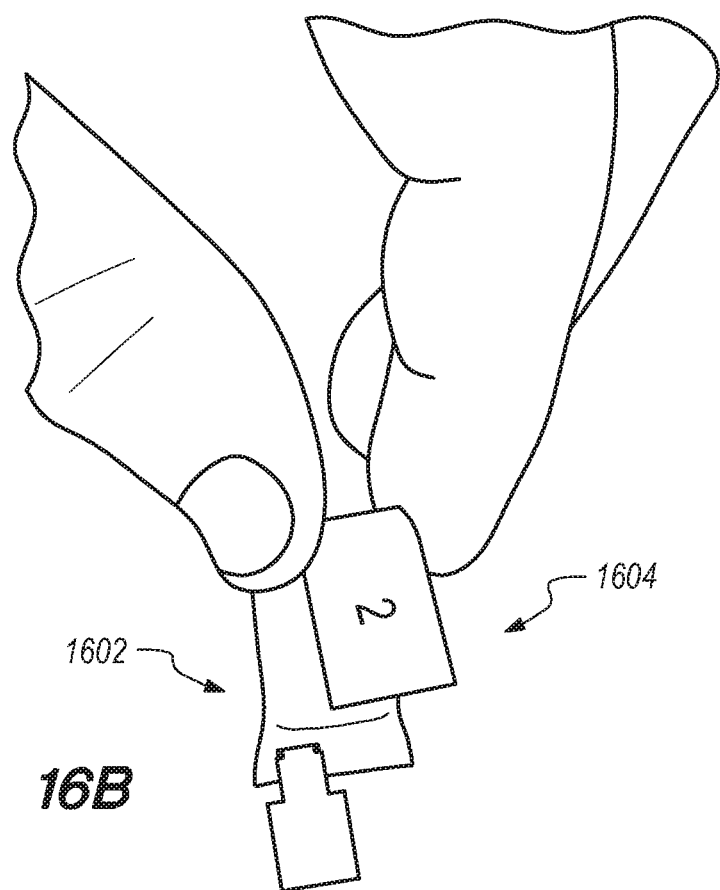
Figure 19A:
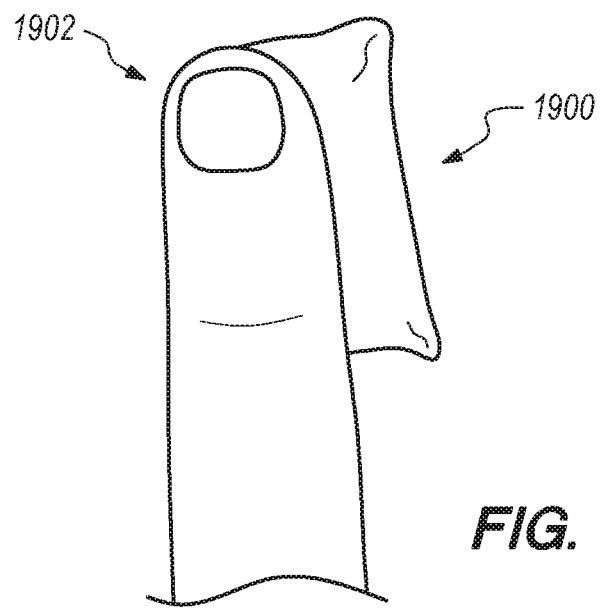
FIGS. 19A-B are a front view and a back view of a preferred embodiment of a wireless, disposable pulse oximeter sensor attached to a user's measurement site (e.g., fingertip), in accordance with an embodiment of the inventions.
Figure 19B:
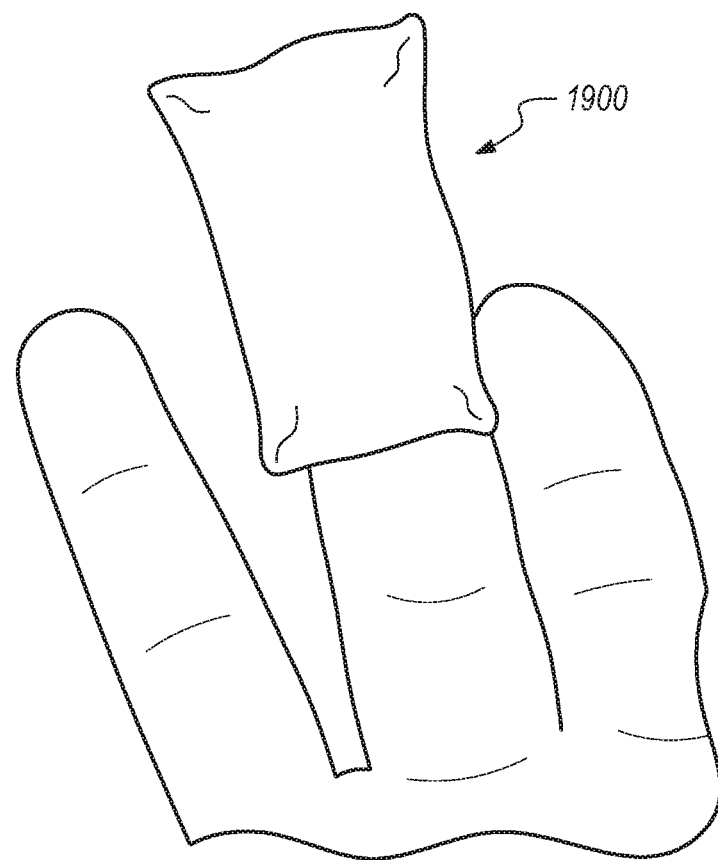

For example, FIGS. 14A-D show the adhesive tape 1402 from FIGS. 9A-B being attached to the adhesive tape 1404 depicted in FIGS. 8A-B. FIGS. 15A-J depict the steps for attaching an adhesive tape assembly 1502 from FIGS. 14A-D to a pulse oximeter assembly PCB assembly 1504 from FIGS. 13A-B. FIGS. 16A-B show attachment of the adhesive tape 1604 from FIGS. 10A-B to the assembly 1602 from FIGS. 15A-J. FIGS. 17A-B show the wireless disposable pulse oximeter 1700 fully assembled. FIGS. 18A-H show the steps necessary to turn on and attach the wireless disposable pulse oximeter 1800 to a body appendage 1802 (e.g., fingertip), according to an embodiment of the inventions. FIGS. 19A-B show a wireless, disposable pulse oximeter sensor 1900 attached to a user's measurement site 1902 (e.g., fingertip).

Figure 20:
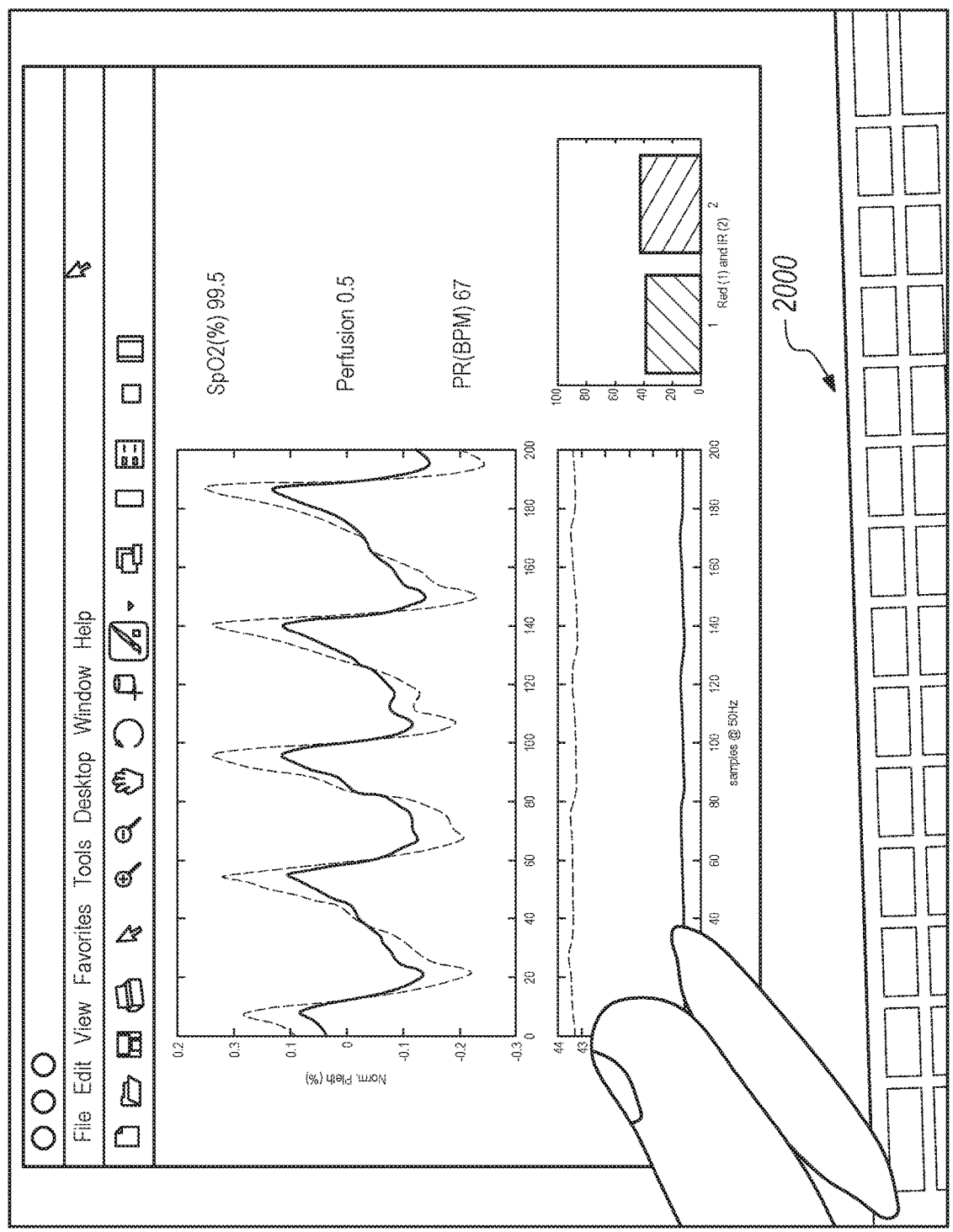
FIG. 20 depicts a preferred embodiment of a wireless, disposable pulse oximeter of the inventions (lower left portion of the figure, affixed to a fingertip) connected to a laptop computer via Low-Energy Bluetooth wireless protocol. In a preferred embodiment, red and near-infrared waveforms are sent to the laptop for processing, visualization, and storage, in accordance with an embodiment of the inventions.
Figure 21:
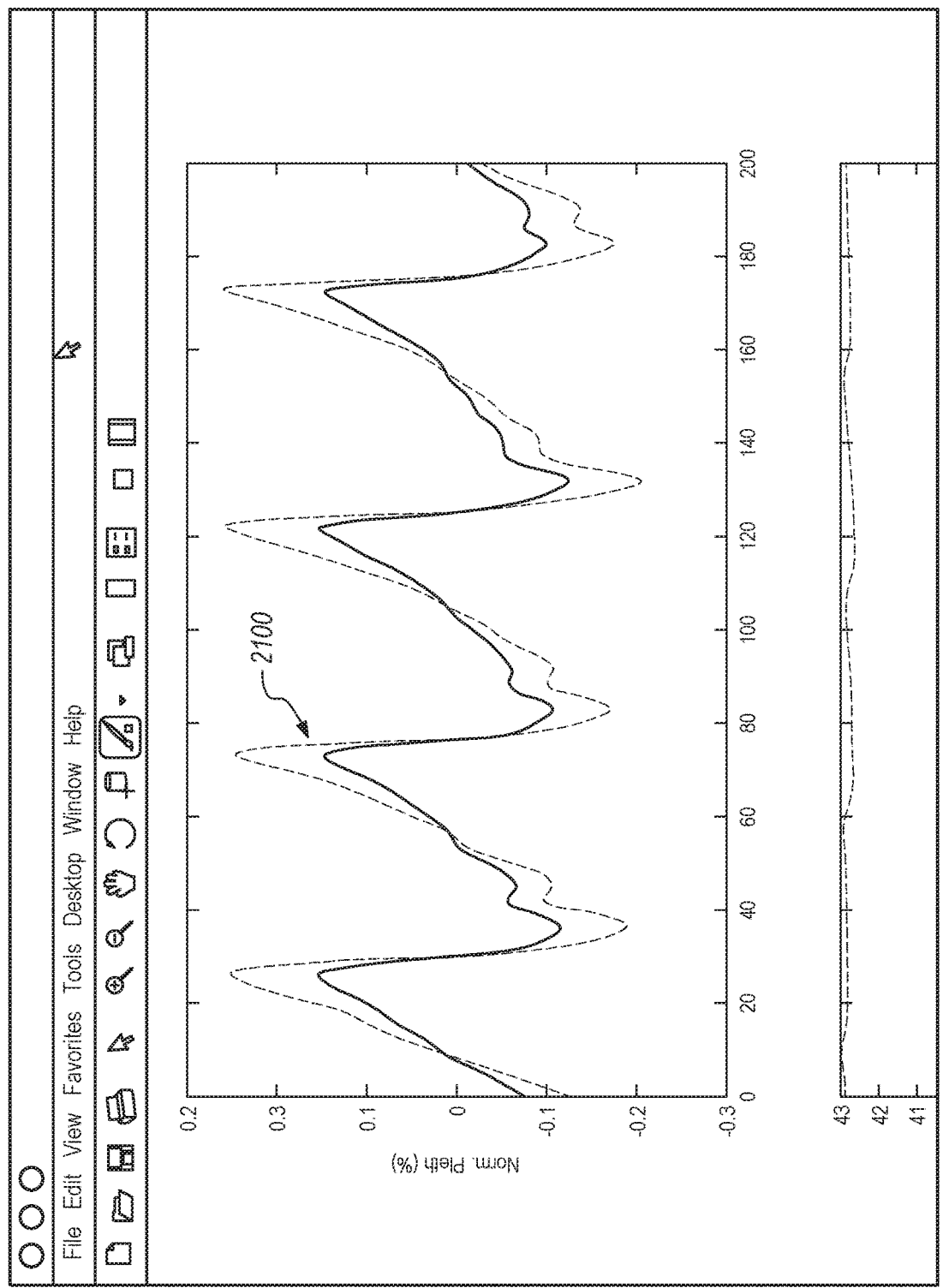
FIG. 21 illustrates a preferred monitor/display showing photoplethysmographs for the red and near-infrared wavelengths, in accordance with an embodiment of the inventions.
Figure 22:
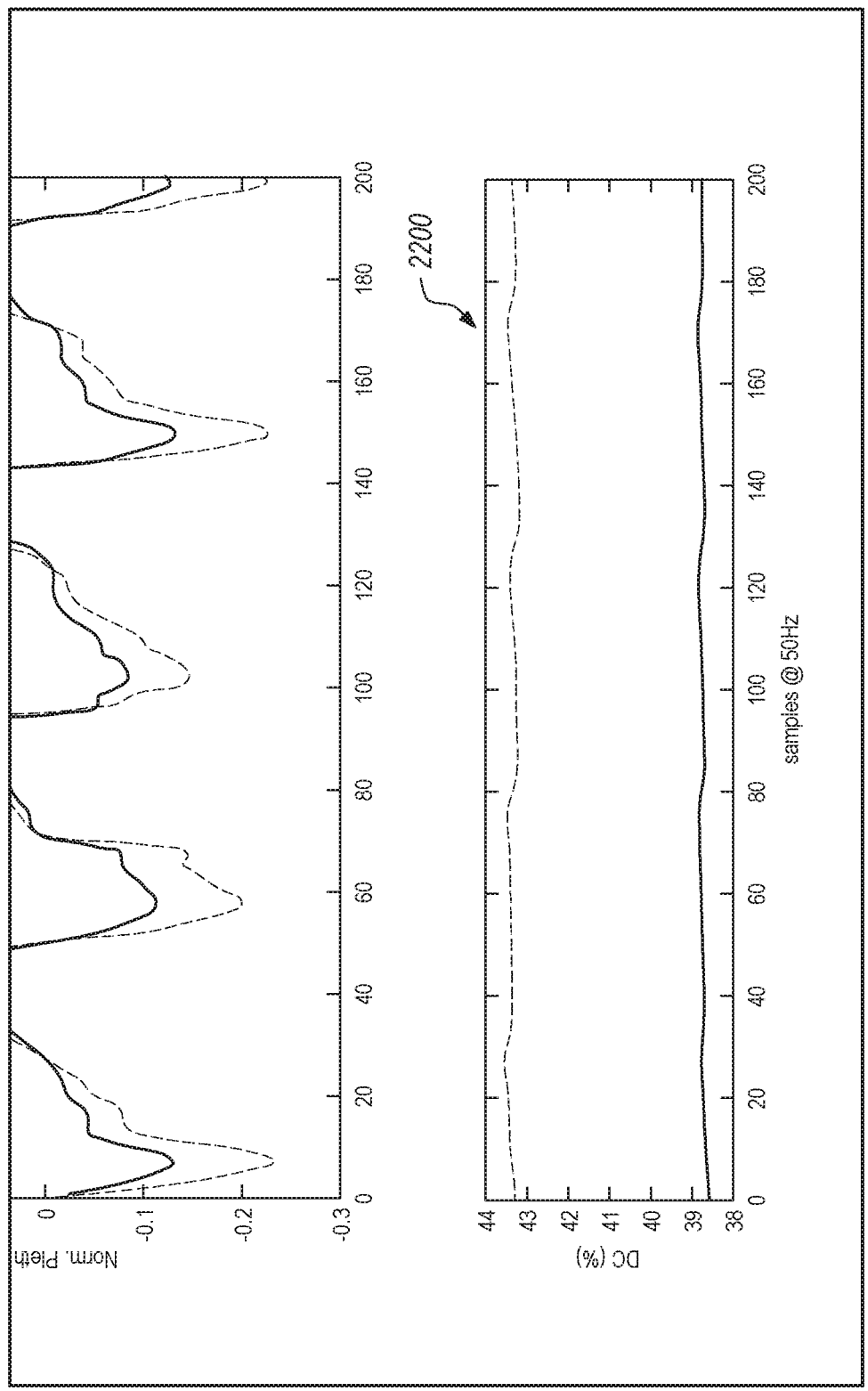
FIG. 22 illustrates a preferred monitor/display showing the red and near-infrared data waveforms sent from the disposable wireless pulse oximeter to a laptop computer, in accordance with an embodiment of the inventions.
Figure 23:
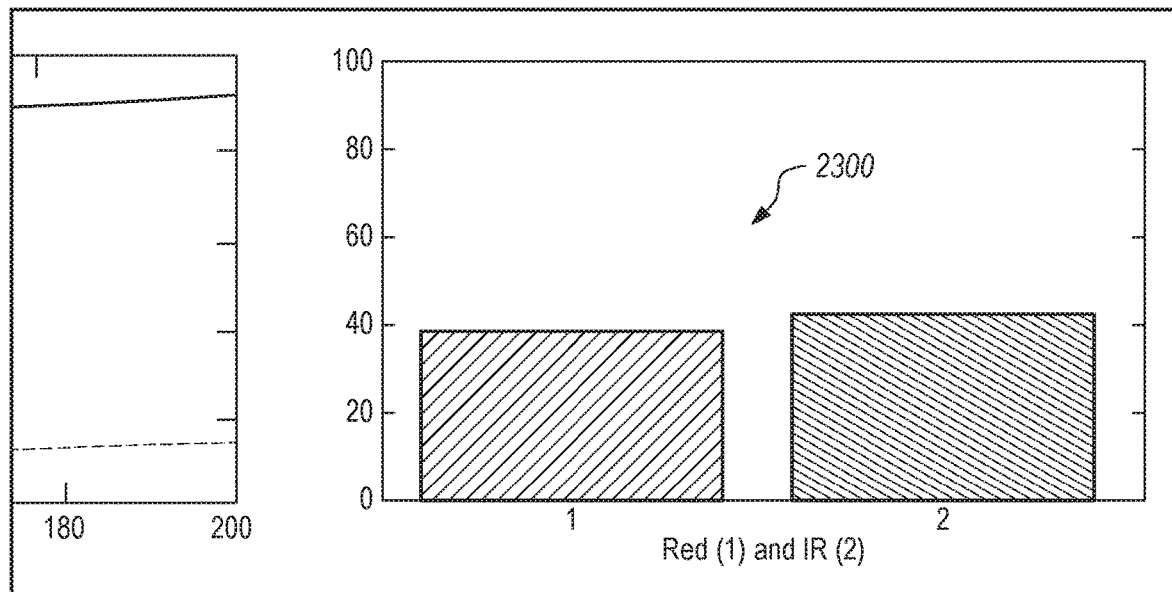
FIG. 23 illustrates a preferred monitor/display showing two bars (one for the red and one for the near-infrared wavelength) depicting the light emitting diode (LED) currents and the internal gains of a pulse oximeter frontend being set to approximately 40% of its dynamic range, in accordance with an embodiment of the inventions.
Figure 24:
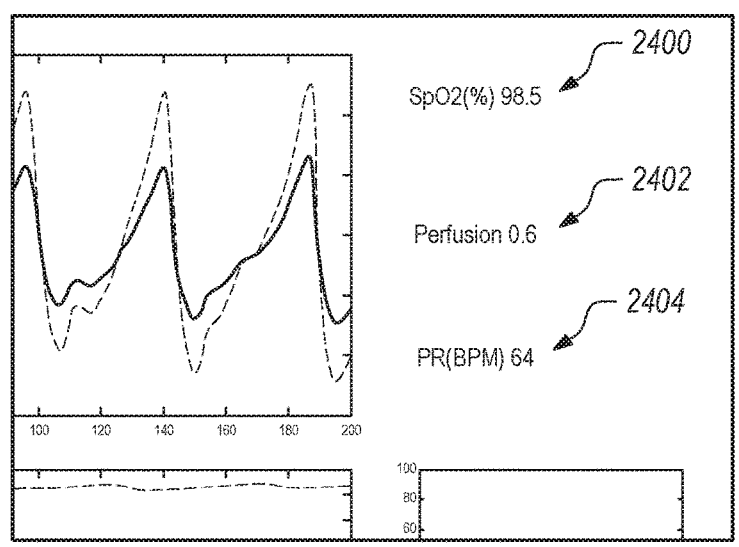
FIG. 24 shows a snapshot of the SpO2, perfusion, and pulse rate measurements performed by preferred demodulation, decimation, led current calibration, sensor off patient, error handling, communication algorithms running on the disposable wireless pulse oximeter to produce high-quality red and near-infrared photoplethysmographs that are wirelessly and continuously sent to a laptop in order to have the oxygen saturation, pulse rate and perfusion index calculated and displayed on the laptop computer or other convenient monitor, in accordance with an embodiment of the inventions.
Figure 25A:
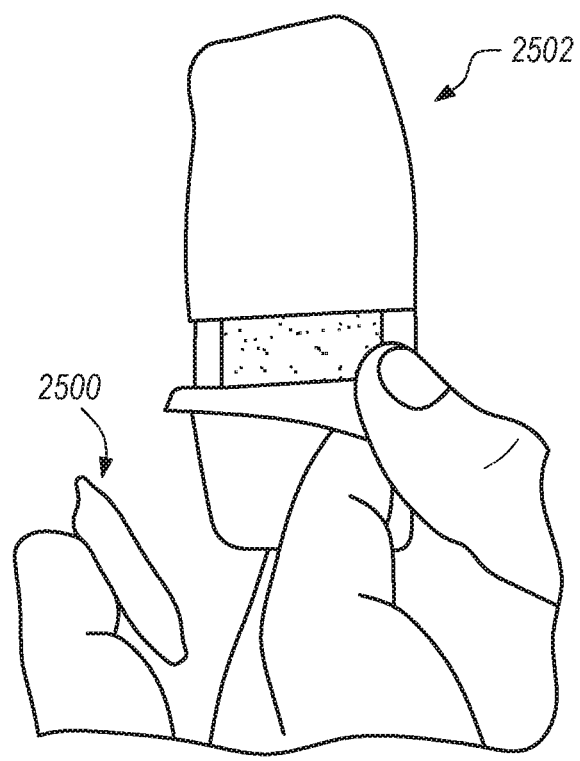
FIGS. 25A-H illustrates apparatus and a series of steps of one of the many embodiments of the inventions, by which a disposable, wireless, continuous pulse oximeter can be wrapped by a disposable adhesive bandage in order to protect the pulse oximeter from environmental conditions and avoid dislodgment of the device on applications that require long term use and/or are subjected to accentuated motion and physical activity, in accordance with an embodiment of the inventions. The disposable adhesive bandage also creates better coupling between the optical sensor and skin, thereby increasing the optical penetration depth for a given emitter-detector separation.
Figure 25B:
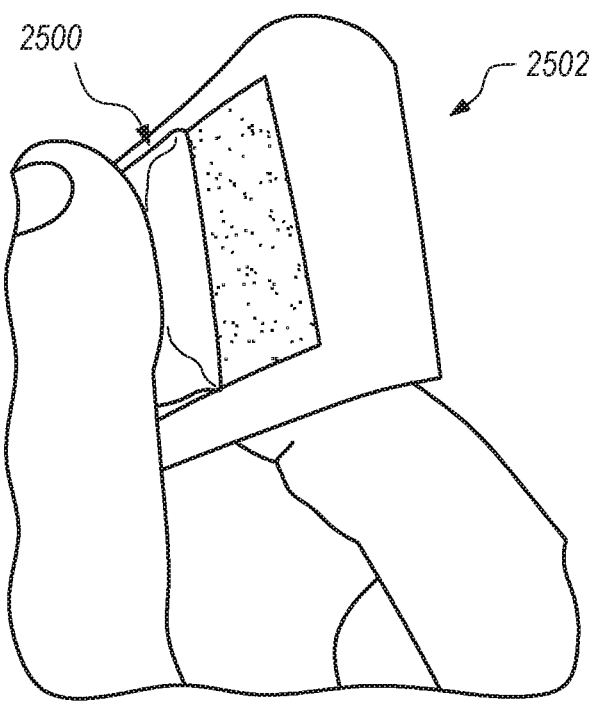
Figure 25C:
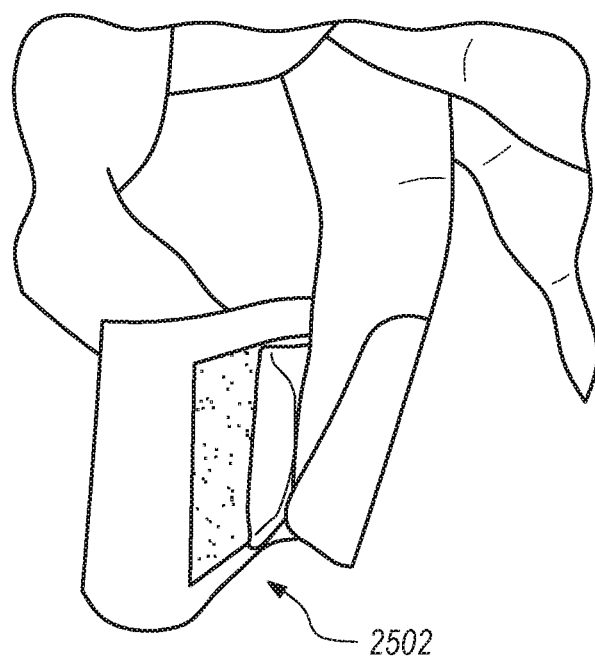
Figure 25D:
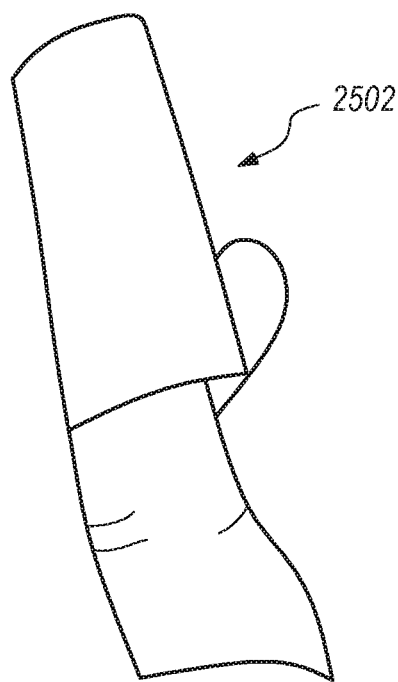
Figure 25E:
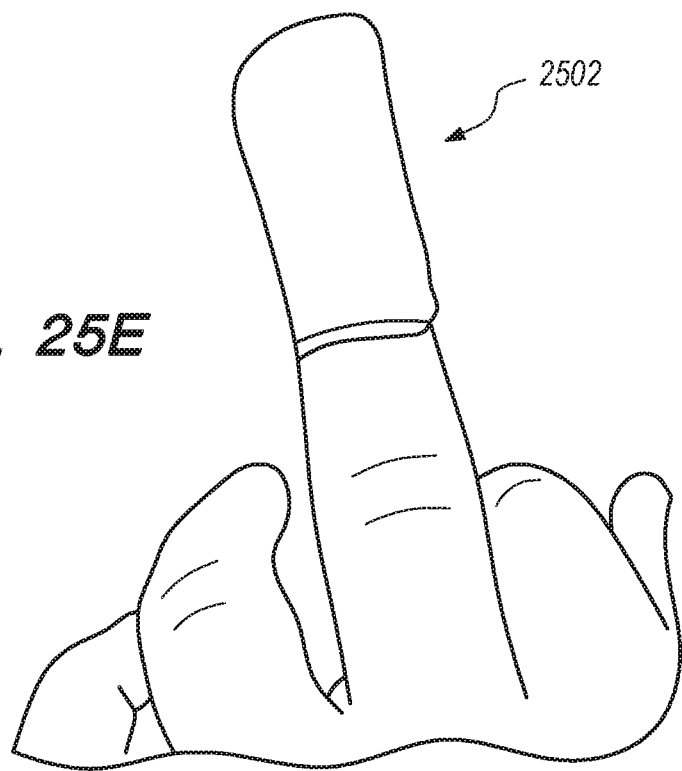
Figure 25F:
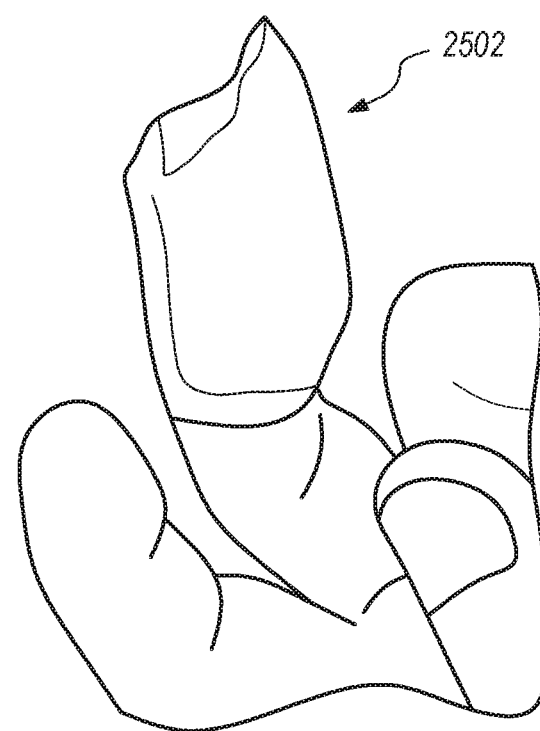
Figure 25G:
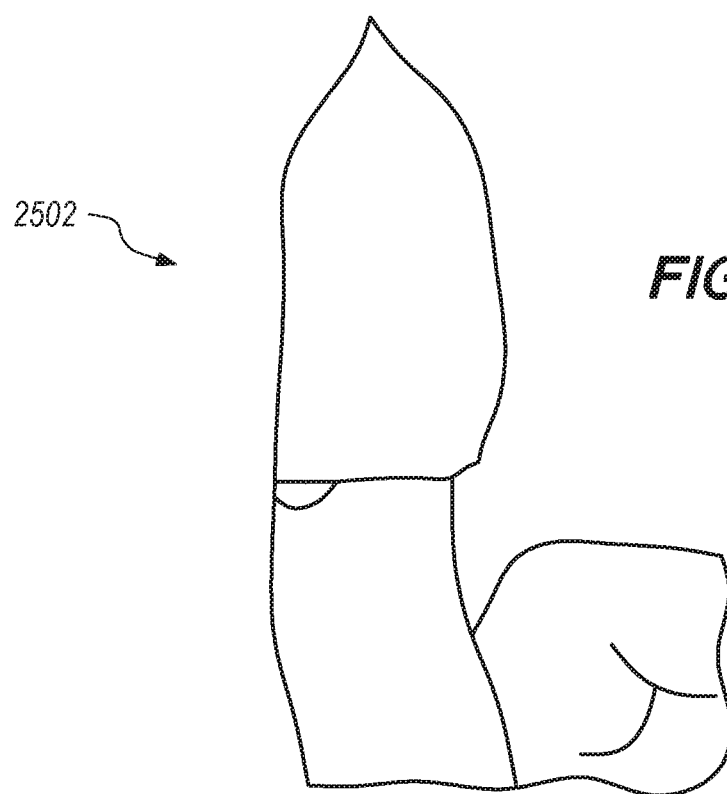
Figure 25H:
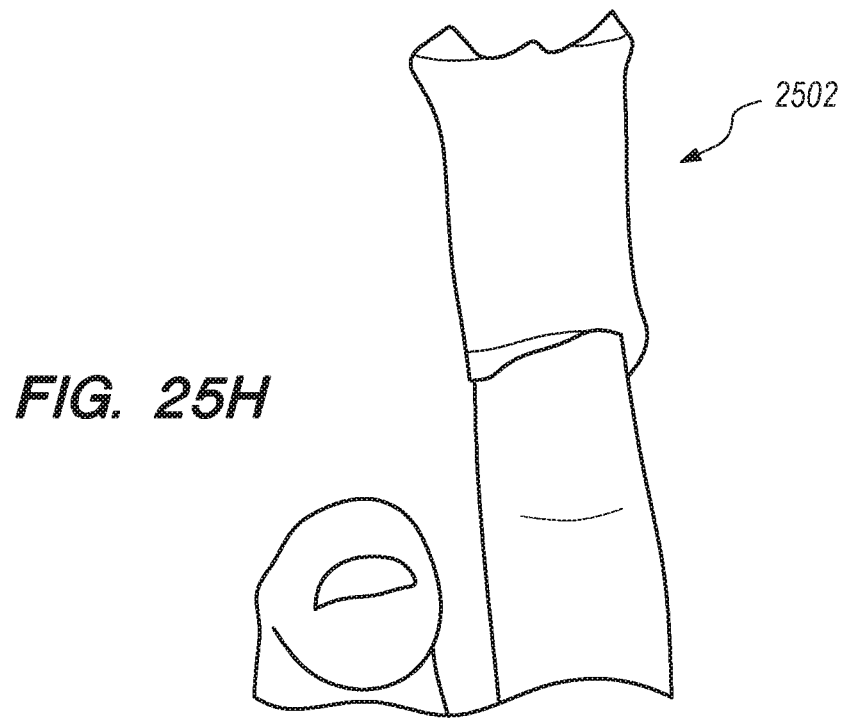

Persons of ordinary skill in the art also will understand that the data monitored and transmitted from the assembly 100 can be used and displayed and/or stored in a wide variety of useful and beneficial ways. The example of FIG. 20 depicts the wireless, disposable pulse oximeter connected to a laptop computer 2000 via Low-Energy Bluetooth wireless protocol. In a preferred embodiment, red and near-infrared waveforms are sent to the laptop for processing, visualization, and storage. FIG. 21 shows the photoplethysmographs 2100 for the red and near-infrared wavelengths. FIG. 22 shows the red and near-infrared data waveforms 2200 sent from the disposable wireless pulse oximeter to the laptop computer. FIG. 23 shows two bars 2300 (one for the red and one for the near-infrared wavelength) depicting the light emitting diode (LED) currents and the internal gains of pulse oximeter frontend being set in order to maintain the frontend's dynamic range around 40% of its full range value. FIG. 24 shows a snapshot of the SpO2 2400, perfusion 2402 and pulse rate 2404 measurements performed by the algorithms running in the disposable wireless pulse oximeter and laptop computer.

Persons of ordinary skill in the art will understand that the details of the apparatus and methods for maintaining the relationship between the sensor assembly 100 and the digit 111 or other location on the patient can be any of a wide variety. One simple and very useful arrangement is depicted in FIGS. 25A-H, which show a preferred wireless, disposable, continuous oximeter sensor 2500 wrapped by a disposable adhesive bandage 2502 in order to further protect the pulse oximeter from environmental conditions and further avoid dislodgment of the device from the patient location/site, such as for applications that require relatively longer term use and/or are subjected to accentuated motion and/or physical activity by the patient or otherwise. The bandage preferably improves the optical compliance and coupling between sensor and skin thereby increasing the perfusion and measured photoplethysmograph amplitudes. FIG. 32 shows the effects and tradeoffs of applying pressure to a wireless disposable continuous pulse oximeter sensor as shown in FIGS. 25A-H by means of a bandage.

Figure 26:
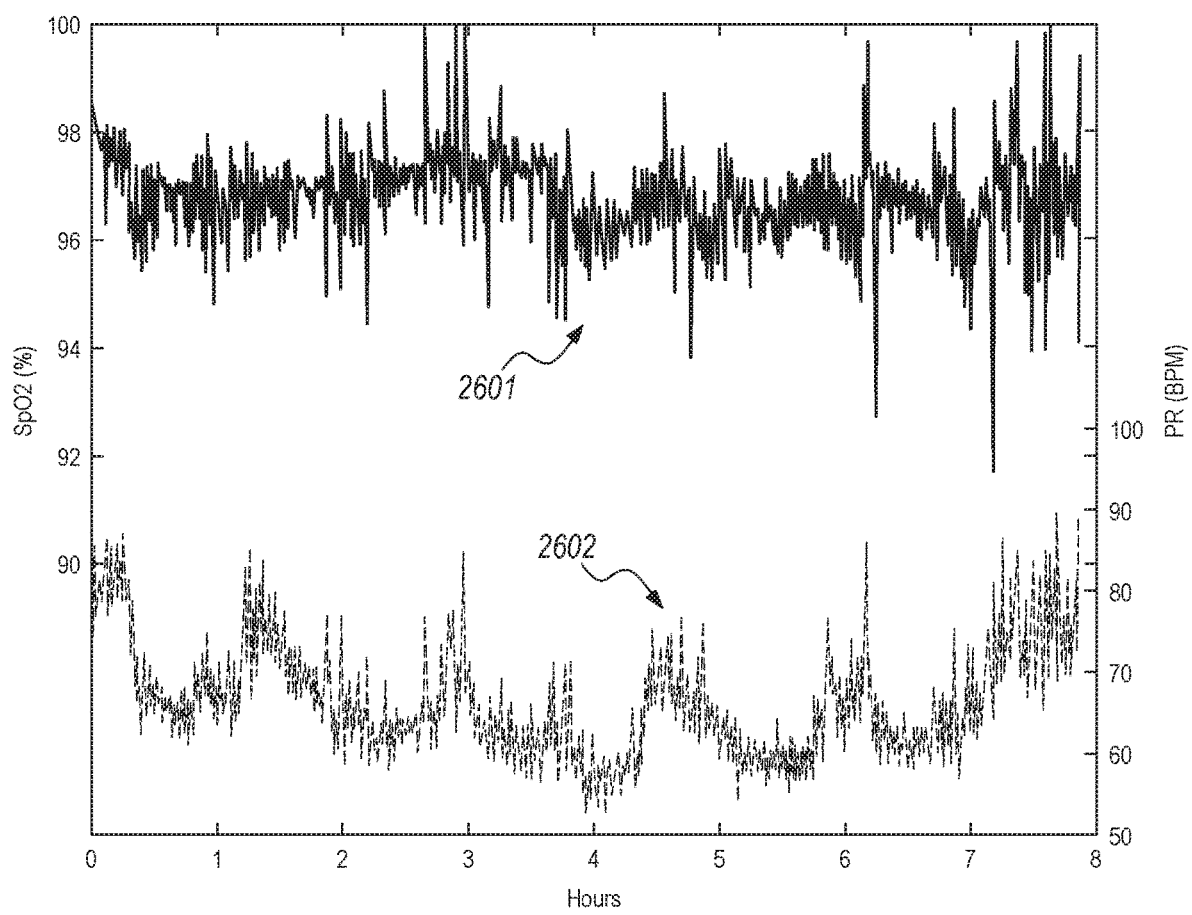
FIG. 26 shows a preferred oxygen saturation and pulse rate trend calculated every second in an 8-hour sleep study collected with a sensor attached to the patient as shown in FIGS. 18 and 19, using the system of FIGS. 20 through 24.

FIG. 26 shows a preferred oxygen saturation 2601 and pulse rate 2602 trend calculated every second during an 8-hour sleep study collected with the sensor attached to the patient as shown in FIGS. 18 and 19 using the system of FIGS. 20 through 24. The sensor was wrapped using an adhesive bandage as shown in FIGS. 25A-H in order to create additional pressure to improve optical coupling between optical sensor and the patient's skin and also to prevent the sensor from coming off from the patient's digit during sleep. The changes in pulse rate 2602 and oxygen saturation 2601 are due to the various sleep stages that the patient experienced during the night.

FIGS. 27A-C show a preferred signal processing unit and detuning resilient ceramic small-loop SMD antenna 2702 (such as the model 2450AT18D0100 from Johanson Technology) and circuit 2701 schematic and printed circuit board layers (top and bottom) of a disposable, wireless continuous pulse oximeter sensor. Preferred ceramic small-loop antennas 2702 offer robustness in performance near the human body and have a smaller footprint when compared to conventional loop antennas.

FIGS. 28A-C show one of the many alternative ways in which the wireless, disposable, continuous pulse oximeter sensor can be packaged, including a 3-part adhesive tape design. For the embodiment illustrated in FIG. 28A, the encapsulation tape design has two additional tabs when compared to the one in FIG. 8A in order to increase encapsulation robustness. It is designed to be attached to the printed circuit board with small-loop antenna shown in FIGS. 27A-C. The tape design that enables the circuit board to be turned on by the clinician or user at the time of use is detailed in FIG. 28B and the tape design that enables skin-to-device adhesion is shown in FIG. 28C, respectively. Persons of ordinary skill in the art will understand that the dimensions and shapes shown in these and other drawings are not intended to be delimiting of the many different embodiments in which the inventions can be practiced. Instead, the dimensions and shapes are only intended to be illustrative of one of the many ways in which the inventions may be practiced.

FIG. 29 shows an exploded view of a preferred wireless, disposable, continuous pulse oximeter sensor with a detuning resilient ceramic small-loop SMD antenna. As illustrated, FIG. 29 includes embodiments of the apparatus shown in FIGS. 28A (element 2903), 28B (element 2904), and 28C (element 2905), 27A-C (element 2901) and lithium manganese dioxide battery (element 2902).

FIGS. 30A-H depict preferred example steps for attaching the adhesive tape assembly of FIGS. 28A-B to the pulse oximeter-PCB assembly of FIGS. 27A-C. FIGS. 30A-H highlight preferred additional steps required in the attachment of adhesive tape from FIG. 28A given its additional tabs when compared to the one in FIG. 8A.

FIG. 31 shows a preferred block diagram of the algorithms that may run on the sensor and the host. The wireless, disposable, continuous pulse oximeter sensor may run the LED driver algorithms (i.e., LED modulation, LED current calibration), the frontend algorithms (i.e., demodulation, decimation) and the supervisory algorithms (i.e., sensor off patient, diagnostics, communication, error handling and alarms). The host device may run the backend algorithms (i.e., oxygen saturation and pulse rate, perfusion index) and supervisory algorithms (i.e., communication, storage, display and data sharing, error handling and alarms). The LED modulation algorithm may produce signals similar to the waveform shown in the upper right where the red and near-infrared LEDs would be turned on and off sequentially and periodically.

FIG. 32 highlights the preferred design tradeoffs in the present inventions which enable the measurement of SpO2, PR, and PI using a small emitter-detector separation while still being able to produce acceptable signal-to-noise ratio figures. Action 1 (decreasing emitter to detector separation) decreases required LED optical power but requires actions 2 (making emitter-detector gap region optically dark) and 3 (applying slight pressure to sensor by means of adhesive bandage) in order to counteract its undesirable effects (i.e., increase in the likelihood of light piping, reduction in the optical probing depth, reduction in the photoplethysmograph amplitude).

FIG. 33 details the preferred design methodology used in the present inventions to quantify the tradeoffs and actions defined in FIG. 32. A physiology model defines the target ranges and condition where the sensor must work within specifications. By solving 3D Boltzmann Transport equations with boundary conditions and applying the results to LED driver, frontend and backend models, it is possible to predict the sensor performance and make changes (if necessary) in the geometry and optical models in order to ensure all specifications are met by the sensor design.

FIG. 37 shows a typical workflow of a disposable, wireless single-use pulse oximeter (OXXIOM™), its advantages and technical specifications according to an embodiment of the inventions. The front 3701 and back 3702 views of the device are displayed highlighting its front identification label, and tabs 1 and 2. In order to apply the device to a patient, one needs to pull tab 1 3703 to turn on the device, and then pull tab 2 3704 to expose the adhesive tape. The device can be placed on the patient's digit 3705, temple 3706, or any other well-perfused site on the patient's body. OXXIOM™ connects wirelessly to the host device, which can be a laptop device 3707, a mobile device 3708, or any other device that has built-in Bluetooth Low Energy (BLE) radio, or similar technology. After use, OXXIOM™ can be disposed or recycled 3709. A typical OXXIOM™ recycling workflow process would follow the following steps:

1. Caregiver or user (buyer) buys OXXIOM™ device(s);
2. Caregiver/user collects used OXXIOM™ devices in batches and ships them to an OXXIOM™ recycling facility;
3. The recycling facility sterilizes the received OXXIOM™ product batches, typically using Chlorine Dioxide (CD) gas. Ethylene Oxide (ETO) sterilization is also suitable. However, in the case of ETO, it is recommended to remove the OXXIOM™ disposable battery soldered to the OXXIOM™ PCB prior to sterilization. The vacuum required by the ETO sterilization process may not be acceptable for embedded batteries such as the disposable lithium manganese dioxide battery preferably used in OXXIOM™.
4. A new battery is soldered to each reprocessed OXXIOM™ PCB and the electronics and built-in optical sensor are tested so as to ensure the same accuracy as a new OXXIOM™ device.
5. A new encapsulation is applied to the OXXIOM™ PCB-battery assembly and the assembled units are packaged and made ready for shipment. The caregiver/user receives a discount on the purchase of a new or reprocessed OXXIOM™ unit for each OXXIOM™ unit successfully recycled.

FIG. 37 describes the advantages that OXXIOM™ offers to patients, users, and healthcare providers. Preferably, the disposable, extended use, wireless pulse oximeter device according to an embodiment of the invention has several competitive advantages when compared to conventional, wired, extended use pulse oximeters.

Firstly, for patients and users, the present invention:
1. Reduces risk of infection and cross contamination;
2. No risk of being exposed to the residue of chemical sterilants;
3. Ease of use, convenient, comfortable, allows freedom of movement;
4. Small, lightweight, water resistant.

Further, for healthcare providers, the present invention:
1. Is single use, fully disposable, wireless;
2. No need to clean/sterilize;
3. No electricity required (under-developed countries, war zones, epidemic areas, etc.);
4. Eliminates failures due to equipment wear and tear;
5. Reduces Healthcare Associated Infections (HAI);
6. Minimal inventory footprint;
7. Easy to stock and transport;
8. Reduction in hospital and Ambulatory Surgical Center (ASC) operations and maintenance costs;
9. Simple workflow;
10. No risk of obsolete equipment.

In addition to the aforementioned advantages, the disposable, wireless pulse oximeter (OXXIOM™) technology, according to an embodiment of the inventions, provides significant capital and operating expenditure reductions for clinics and institutions that conduct sleep studies on patients in order to diagnose sleep-related disorders, such as obstructive, central, child, infant sleep apneas, snoring, sleep related groaning, etc. Typically, with reusable, wired technologies, the reusable device and disposable (reusable) sensor are shipped to the patient's house so as to collect data overnight. The collected data is later sent to the clinic for post-processing, analysis and diagnostics. Once the test is complete, the patient needs to ship the pulse oximeter back to the clinic so as to be sterilized and repacked for the next patient. The shipping and sterilization steps increase operating costs, and also increase workflow complexity. In addition, the clinic needs to have in stock enough reusable pulse oximeters to be able to supply test demands, which increase the capital investments required to operate. Currently, a typical continuous, clinical-grade, wired pulse oximeter costs, on average, approximately 50 times the price of an OXXIOM™ unit (as depicted in FIG. 37) depending on the model and functionalities. A clinic performing 1000 tests a month, for instance, would need at least 125 reusable oximeters in order to keep up with test demand, if one assumes that it takes one day to ship the device to the patient's house, one day to conduct the test, one day to ship the device back to the clinic, and one day to have the device sterilized and sent to another patient's house, which would allow a device to be used twice a week, or eight times a month at most. This implies that the clinic would need capital investments in reusable oximeters of approximately 6250 times the price of an OXXIOM™ unit, in addition to costs incurred in shipping, processing, and sterilization. This would translate into approximately 6 months worth of testing, with operating expenses reduced by the savings with sterilization, processing, and at least half of the shipping costs. In addition, no new capital expenditures would be needed for expansion/upgrades.

According to the technical specs in FIG. 37, OXXIOM™ is small (30×17×7.5 mm) and lightweight (3.5 g), has clinical-grade performance as defined in ISO 80601-2-61, is fully disposable and wireless. As a result, it offers advantages in terms of comfort and convenience in applications where sterility, workflow, and sensor size/weight are a concern. Such is the case on the monitoring of infants and neonates. Infants and neonates should be constantly monitored during the first hours (days or weeks) of birth. A device like OXXIOM™ can be conveniently applied to the foot (neonate) or the right hand (normal infant), allowing the caregiver to have complete and free access to the baby without being concerned about the size and weight of the cables and sensor that conventional wired continuous oximetry requires. This allows the caregiver to move the infant around as needed without carrying a wired monitor or checking whether the pulse oximeter cable is of adequate length to reach onto infant.

FIGS. 38-45 show screen shots of an app that runs on a host device (iPhone) that pairs with OXXIOM™. The OXXIOM™ device (sensor) has been designed and manufactured according to an embodiment of the inventions. FIG. 38A-B show app icon 3801 and startup screen 3802. FIG. 39A shows the measurement screen indicating that OXXIOM™ is not connected to the host device 3903. FIG. 39B shows the pop-up options 3901 that are made available to the user once the side drawer 3902 is selected. The "Start" option gives place to the screen shown in FIG. 40A, which allows the user to enter the OXXIOM™ barcode, patient ID barcode, gender and date of birth. By selecting "Scan it" 4001, the barcode scanner screen is displayed (as shown in FIG. 40B), which allows the user to scan the OXXIOM™ barcode to enable a secure Bluetooth pairing between the host device and OXXIOM™ or to scan the barcode that identifies the patient (as shown in FIG. 41A). The barcode scanner support several types of barcode formats, including QR, UPCE, Code39, Code39Mod43, EAN13, EAN8, Code93, Code128, PDF417, Aztec, Interleaved2of5, ITF14 and DataMatrix. Other forms of secure pairing can also be used such as the Bluetooth pairing using the Near Field Communication (NFC) Protocol. FIG. 41B shows the resulting screen after the barcodes are scanned and the patient's gender and date of birth are inputted.

Figure 42B:
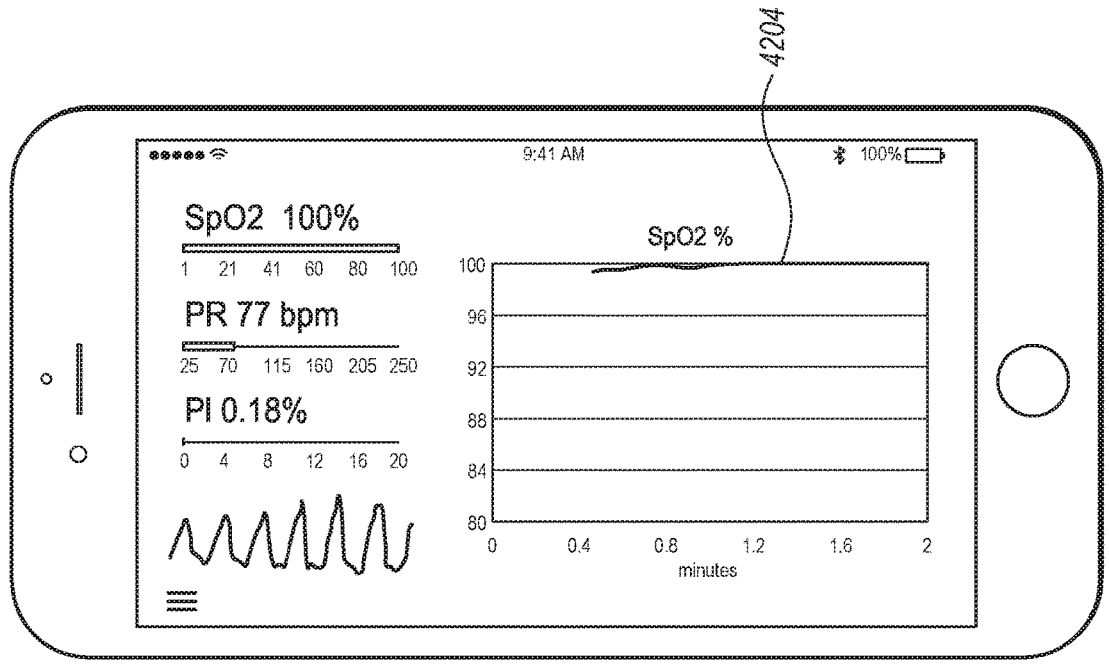
Figure 42A:
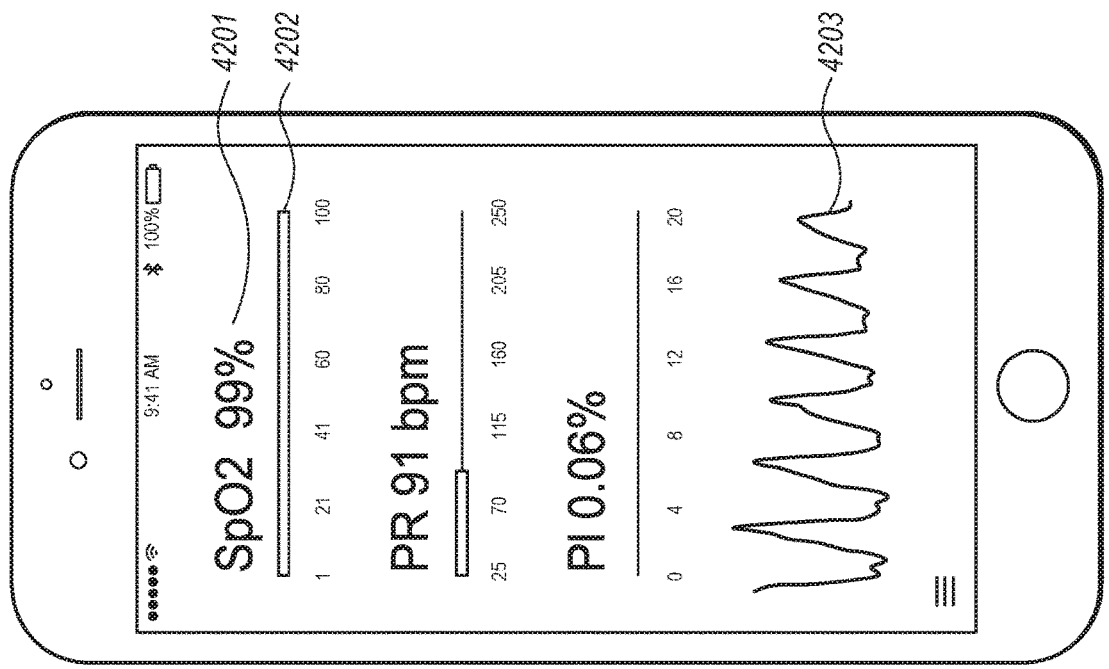

FIGS. 42A-B depict the SpO2, PR and PI measurements and trend data, and waveforms 4203 being displayed by the host device after OXXIOM™ is placed on the patient and paired with the host device (iPhone). For each parameter displayed, a numerical display 4201 combined with a linear gauge indicator 4202 are provided. When the host screen is turned into landscape mode, data trends 4204 are also displayed. The parameter in boldface font (i.e., SpO2) on the left indicates the current trend data being displayed on the right. To change the trend data (i.e, PR) on the right, just select the corresponding numerical display on the left as shown in FIG. 43A. In the case of an alarm indicating that a parameter is outside of its normal range, the corresponding numerical display and linear gauge will turn into red color and an audible alarm will be triggered so as to alert the caregiver about a potential abnormal patient condition. In order to ensure the caregiver receives the alarm notification, if the remote notification option is enabled, the host device will send a text message and an email to the caregiver notifying him or her about the abnormal patient condition. In this case, the text or email message will contain the patient identification (ID, gender, date of birth) and location, as well as the current parameter readings and alarm settings.

Figure 43B:
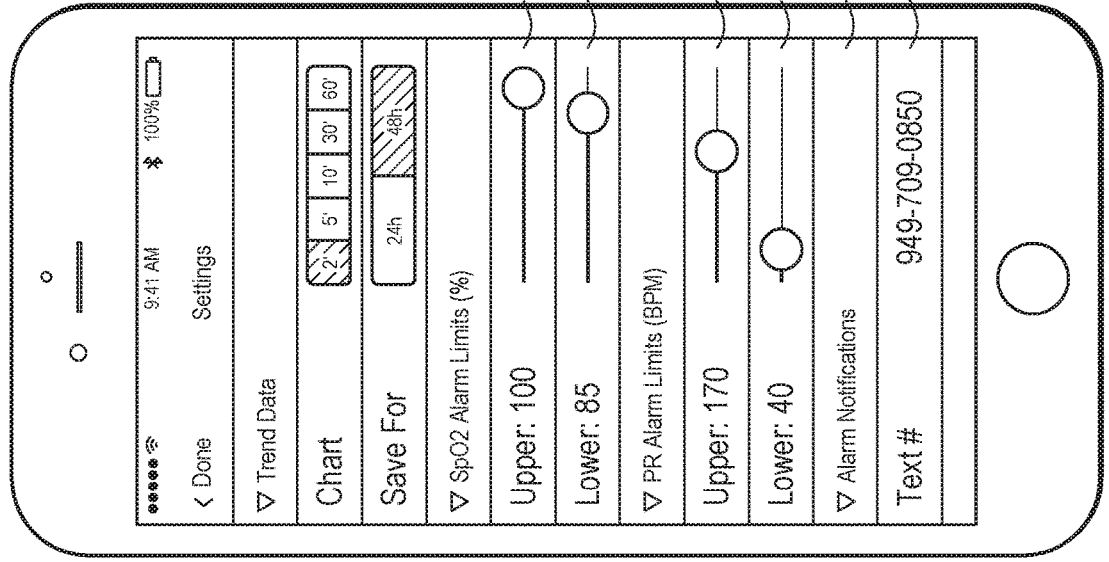
Figure 43A:
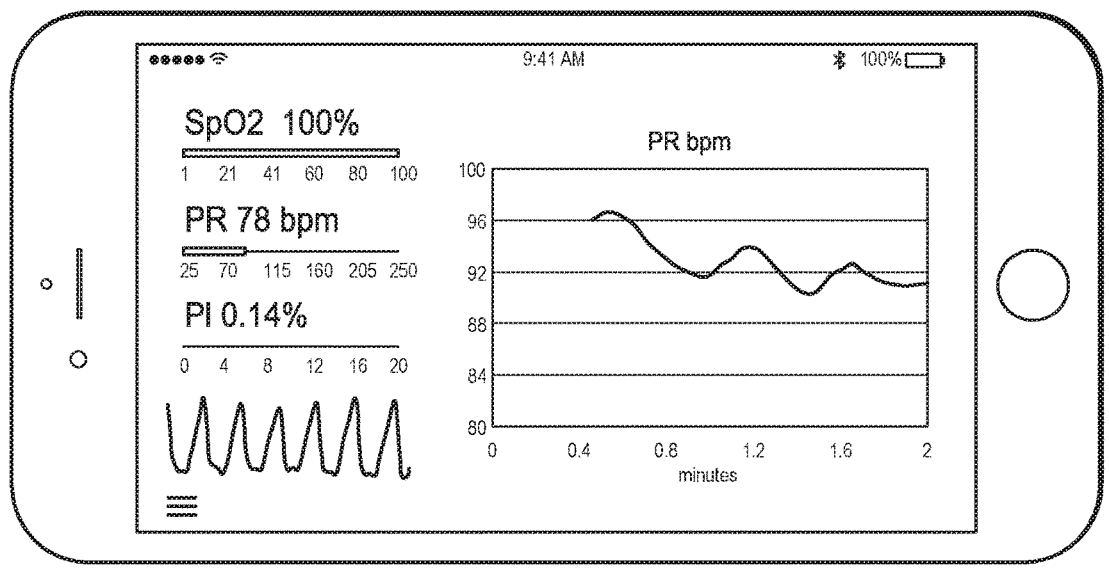

The "Settings" option, when selected from the side drawer, gives place to the screen shown in FIG. 43B. In this screen, one can select the data trend duration (2, 5, 10, 30 or 60 minutes), how long the trend data will be saved (last 24 or 48 hours), and upper and lower SpO2 and PR alarms, which can have their values changed through sliding switches 4301 4302 4303 4304. In this same screen, there is a field named Alarm Notifications 4305, wherein one can enter the phone number(s) of caregiver(s). In case an alarm is trigged, a text message as described anteriorly is sent to the caregiver(s) via the phone number inputted on "Text #" field 4306.

Figure 44B:
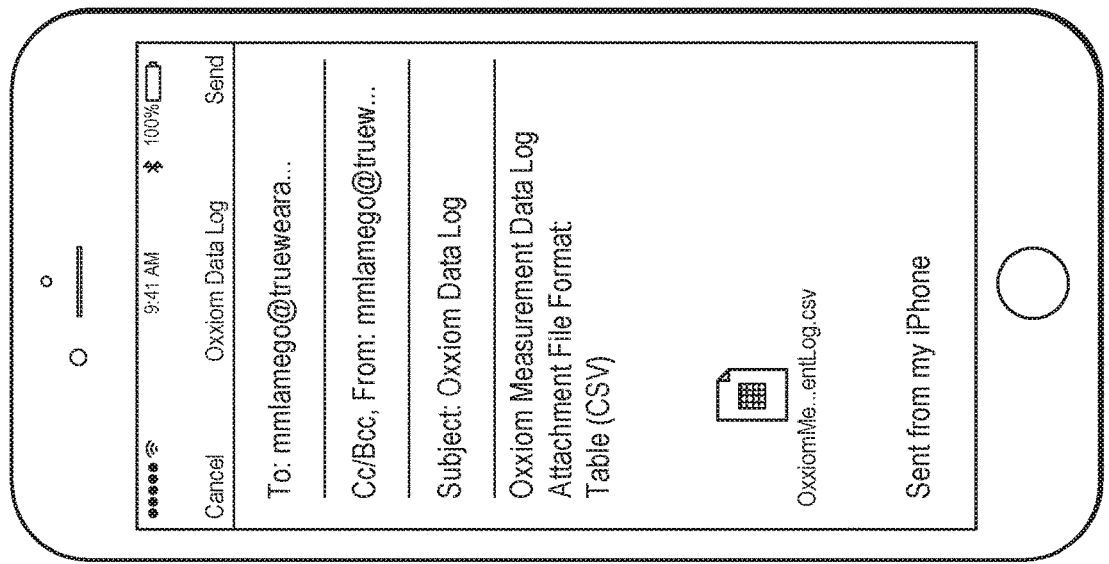
Figure 44A:
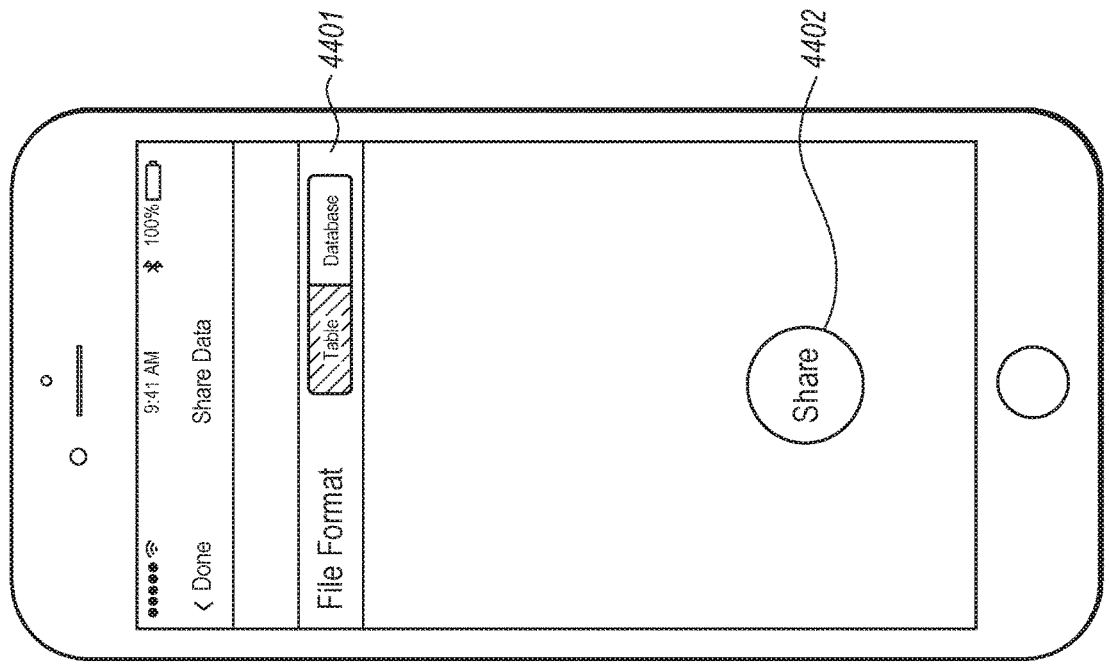

FIGS. 44A-B and 45 show an example of how trend data can be shared. The "Share Data" option, when selected from the side drawer, gives place to the screen shown in FIG. 44A. The user can then choose the file format 4401 (i.e, table or database), and once the user selects "Share" 4402, the screen depicted in FIG. 44B is made available to the user. In this screen the file with the selected format is attached to an email. In this case, the user selected the table format, and as a result, a Comma Separated Values (CSV) file was attached to the email message. The user then inputs the receiver's email and select "send" to have the email message delivered to the receiver. There are several possible sharing options, including cloud sharing, where a file is sent to a cloud storage service that can then be accessible by designed receiver(s). It is also possible to have short-range peer-to-peer sharing via WiFi or Bluetooth, such as the AirDrop® ad-hoc service from Apple, Inc. This service allows the transfer of trend data files without using email or mass storage devices.

FIG. 45 shows the content of a CSV file with trend data. Each row represents a single measurement record, with a time stamp (Date/Time), OXXIOM™ barcode, patient's ID #, Gender and DOB (Date Of Birth), and the SpO2, PR and PI measurements. The user has selected, in the "Settings" screen depicted in FIG. 43B, a 48-hour trend data storage, and thus, a measurement record is saved to the CSV file every 8 seconds. If the user had selected 24-hour trend data storage, then a measurement record every 4 seconds would be saved to the CSV file. These sampling rates (1 measurement every 4 or 8 seconds) are suitable to most clinical applications that perform trend data analysis for SpO2, PR and PI. There are other applications, however, where higher sampling frequencies might be required. OXXIOM™ can be configured to save measurements at a higher sampling frequency, such as one measurement record per second. The drawback is that the size of the trend data file to be shared increases proportionally with the sampling frequency.

In some applications, such as sleep studies, it is convenient to have also a oximetry report where statistical analysis is performed on the saved trend data. FIG. 46 shows an example of a Sleep Study Oximetry Report that OXXIOM™ can share with recipient(s) (i.e., caregiver(s)). The report has a header with the basic patient identification, the OXXIOM™ barcode, date of the study and total recording time of the trend data. The three columns below the header show some statistical results related to each parameter measured during the study (i.e, SpO2, PR, and PI). As can be seen from the results shown in the report, the patient was subject to several desaturations (40) during sleep, and her saturation levels reached a minimum value of 70%. These results combined with the average, median, standard deviation, maximum, and minimum SpO2 and PR values, percentage of SpO2 values below 90%, 80%, and 70%, and maximum desaturation value and duration can help the physician diagnose potential patient's sleep-related disorders. The statistics about PI (Perfusion Index or Pulse Strength) in the report may also aid the physician to access the patient's level of comfort during the study. Very low PI values (when compared to the average or median PI values) may indicate, for instance, that the patient was feeling cold during the study, and this may have a negative effect on the observed results.

FIG. 47 is a detailed view of a liner tab with XYZ-axis electrically conductive tape used to implement an one-time ON switch (required to activate OXXIOM™) with dimensions and design identical to the one shown in FIG. 28B, with the exception that the electrically conductive tape changed from a copper foil layered with conductive adhesive to a XYZ-axis conductive adhesive without copper foil. In FIG. 48, this liner tab 4801 is attached to the OXXIOM™ Encapsulation 4810. In order to activate OXXIOM™, the liner tap is pulled by the user so as to allow the electrically conductive tape 4802 to close the gap 4807 between the electrical contacts 4803, and thus enabling the circulation of electrical current from the internal battery 4808 to the PCB 4809 electronic circuits. The use of highly conductive adhesive tapes such as the 3M 9713 eliminates the need for a conductive material (such as copper) to be layered together with the conductive tape as in one embodiment shown in FIG. 28B. This simplifies the one-time ON switch design. The two electrical contacts can be designed in several shapes and forms. In FIG. 48, three layout examples are shown for the contacts, a 2-pole configuration 4804, a parallel-plate configuration 4805, and a spiral configuration 4806. The spiral and parallel configurations are advantageous compared to the 2-pole configuration in the sense that the gap boundaries (parallel lines between the two electrical contacts) are increased substantially for the same area of contact, which in turn reduce the overall contact resistance of a conductive adhesive tape applied on top of such surface layouts. This concept is illustrated with a 2-pole configuration with an extended gap boundary 4811 and its equivalent parallel-plate configuration 4812. The 2-pole configuration 4811 requires a larger contact length in order to accommodate the same gap boundaries as the parallel-plate configuration 4812. The reason why the contact resistance of the one-time ON switch (created when conductive adhesive tape is applied on top of such gap boundaries and contacts) is reduced as the gap boundary increases, while maintaining the same contact gap, has to do with the physical principle of electrical current circulation in parallel circuits. The conductive adhesive tape adhering the two contacts over the contact gap can be modeled as a resistor with value proportional to the gap size and inversely proportional to the contact size area and gap boundaries. By increasing the gap boundaries, one is effectively decreasing the contact resistance because this is electrically equivalent to adding more resistors in parallel throughout the gap boundaries, or adding more conductance per unit of gap boundary length, which in turn has the net effect of reducing the overall contact resistance of the one-time ON switch. The 2-pole configuration is a simpler and more robust design, even though it might offer a higher contact resistance. However, a careful selection of the appropriate separation between the two contacts (gap), combined with the use of a highly conductive tape may offer a simpler and also reliable solution.

FIG. 49 outlines some use-case scenarios for the OXXIOM™ device. For a hospital facility 4901, OXXIOM™ units applied to patients are connected to the hospital network cloud services 4902. The hospital, in this example, comprises of three different physical locations. The first location houses the computer servers running the cloud services 4902 4907. The second houses the pediatrics unit, and the third, the surgery, recovery, and ICU units. These three locations are connected to the Internet via optical links in order to enable reliable connections and data throughputs. In the pediatrics unit, one OXXIOM™ unit 4903 is placed on a newborn. In this configuration, the OXXIOM™ communicates via Bluetooth Smart (BLE) protocol with a mobile/portable device 4904. The host device sends information (i.e., measurements, waveforms, patient identification, alarms, etc.) to the hospital network via WiFi protocol through a router 4905. The use of a mobile device 4904 provides great freedom to the caregiver as the newborn is moved around to be weighted, measured, and have its vital signs checked and physiology examined, since no wires are attached to the newborn and OXXIOM™ is very small and lightweight, while at the same time, provides real-time measurements of SpO2, PR, PI, waveforms and trend data. The other OXXIOM™ unit 4906 in the pediatrics unit is applied to a neonate. In this case, OXXIOM™ communicates wirelessly with a router 4905 using IPV6 (Internet Protocol Version 6) over Bluetooth Smart protocol. No host device is needed and the waveforms and OXXIOM™ diagnostics (battery current charge, connection status, patient identification, etc.) are sent to the OXXIOM™ Cloud Service 4907. The waveforms and OXXIOM™ diagnostics are then processed in real-time by the OXXIOM™ Cloud service in order to calculate SpO2, PR, and PI measurements, trend data, and generate alarms if needed. This information is stored in the hospital network 4902 and conveyed to the caregivers through their mobile/portable devices. The surgery unit has an OXXIOM™ 4909 (attached to a patient under surgery) that communicates wirelessly with a router 4911 using IPV6 over Bluetooth Smart protocol. The waveforms and OXXIOM™ diagnostics are sent to the OXXIOM™ Cloud Service 4907 via router 4911. The waveforms and OXXIOM™ diagnostics are then processed in real-time by the OXXIOM™ Cloud service in order to calculate SpO2, PR, and PI measurements, trend data, and generate alarms if needed. This information is stored in the hospital network 4902 and sent (via router 4911) wirelessly to a multi-parameter monitor 4912 located in the same surgery unit and being used by the surgeon(s) and anesthesiologist(s) to monitor and display in real-time information about the patient under surgery (i.e., SpO2, PR, PI, waveforms, respiration rate, ECG, EEG, etc.). Similar wireless topology concepts are shown in the recovery 4913 and ICU 4914. The selection of an OXXIOM™ configuration that requires or not a host device depends on a number of factors including safety levels, cost, and convenience. For hospital applications where the wireless network is not reliable, a mobile (or multi-parameter monitor) acting as the host device and wirelessly connected to OXXIOM™ via BLE would be preferable. When a reliable wireless network is available, or when short measurement interruptions are not of critical importance, then the operation of OXXIOM™ without a host device and connected directly to a router via IPV6 over Bluetooth Smart could be financially advantageous, and could simplify OXXIOM™ workflow (insomuch as it eliminates the need of a host device paired with OXXIOM™). FIG. 49 also shows some use-case scenarios for the OXXIOM™ device in home settings. In home 1 4915, the OXXIOM™ is paired with a mobile device that conveys measurement, alarm, and waveform information to the user (patient) as well as sends the same information wirelessly and in real-time through a router (Internet) to the hospital network. The mobile device could also send the same information via its mobile wireless network (if available), eliminating in this way the need for a router. Home 2 4916 has an OXXIOM™ connected to a mobile device that conveys measurement and waveform information to the user (patient) without sending it in real-time to the caregiver. The saved trend data could be sent afterwards to a recipient (doctor's office, sleep monitoring clinic, etc.) for further analysis and diagnosis. In the case of a home setting with reliable wireless network and internet connection, such as home 3 4917, OXXIOM™ could be connected to a router (Internet) that would send the waveforms and diagnostic information directly to the OXXIOM™ Cloud Service 4907 so as to calculate SpO2, PR, and PI measurements, trend data, and generate alarms if needed, as well as share this information with the caregiver for appropriate action(s).

FIG. 50 depicts the drawings and technical specifications of OXXIOM™'s lithium manganese dioxide (Li—MnO2) custom primary (not rechargeable) battery. The Li—MnO2 battery is well suitable for low-cost application where relative safety levels and size/weight requirements are a concern. Such is the case of medical devices such as OXXIOM™. When compared to other battery technologies, it offers high energy density (about 250 Wh/kg), wide operating temperature range (−5 to 60 Celsius), long shelf life (due to very low rate of self-discharge), and can withstand high pulse current transients that typically occur in wireless radio circuitry such as the one present in OXXIOM™ (i.e., Bluetooth Low Energy). The battery's top view 5001 with width, length, and terminal dimensions and separation as well as the side view 5002 with thickness are shown in FIG. 50. The battery's discharge curves 5003 for a typical 5005 and worst-case 5004 scenarios are also depicted in FIG. 50. OXXIOM™. In both cases, for a 5-mA discharge current, the battery's terminal voltage drops slowly with time until it reaches 2.1V. At this value, the OXXIOM™'s circuitry no longer works reliably, and it is shut down with a notification sent to the user. The changes in battery nominal capacity observed in FIG. 50 (from 120 to 150 mAh) are due to manufacturing process and lot-to-lot variations. However, in the worst-case scenario 5004, the battery stores enough energy to power OXXIOM™'s circuitry continuously and uninterruptedly for 24 hours. The well-behaved and almost flat discharge curves 5004 5005 seen with the Li—MnO2 battery enable OXXIOM™ circuitry to be connected directly to the battery terminals without the need for voltage pre-regulation. This simplifies the required circuitry and also eliminates undesirable interferences and additional noise typically found in circuitries that require high-efficiency switching regulators for voltage pre-regulation. A complete set of specifications 5006 for the OXXIOM™'s custom battery is also depicted in FIG. 50. The physical separation (gap) between positive and negative terminals is chosen to be the smallest possible (from 2 to 5 mm) so as not to compromise safety levels. Given that the battery is soldered to OXXIOM™'s PCB, and should be perfectly aligned with OXXIOM™'s circuitry and SMD antenna to enable the soft encapsulation to take place, the small terminal separation provides less mechanical resistance to small adjustments required to compensate misalignments between PCB and battery that may occur during the soldering process.

There are applications where a single-use fully disposable device like OXXIOM™ might be required to operate for more than 24 hours continuously in a single patient. Short of replacing the device with a new one every 24 hours, one way of enabling longer uninterrupted monitoring intervals is to increase the OXXIOM™'s battery capacity. However, this implies increasing the size and weight of the device, which is not desirable in most clinical settings and monitoring applications. Another way is to divide the OXXIOM™ device 5121 into three parts as shown in FIG. 51. Part 1 5100 is a multi-layer biocompatible adhesive tape that is responsible for attaching the OXXIOM™ device to the patient skin (i.e., finger, temple, forehead, etc.). Part 2 5105 is the OXXIOM™ circuitry encapsulated (i.e., optical detector and emitter 5107, PCB 5111 and components 5109, antenna 5110, electrical contacts 5108, and encapsulation 5106). Part 3 5119 is the encapsulated assembly with non-rechargeable disposable battery 5118, non-volatile memory 5117, flex circuit 5116, electrical contacts 5115 and adhesive tapes and release liners 5112 5113, and electrically conductive adhesive tape contact pads 5114. Part 1 and 3 are relative inexpensive when compared to Part 2. As a result, in order to reduce overall monitoring costs in applications that require extended interrupted continuous monitoring (for more than 24 hours for instance), one can ship to the user (caregiver) a package that could contain a single Part 2 unit, and several Part 2 and Part 3 units. FIG. 51 shows an example of a shipping package 5120 containing ten units of part 1, five units of Part 3, and one unit of Part 2. This allows the caregiver to change the adhesive tape connecting the patient and device every 12 hours (for convenience), replace the battery every 24 hours for a continuous monitoring period of up to five days or 120 hours. At the end of the extended monitoring period (fifth day), the disposable oximeter circuitry (Part 2) and used Part 1 and Part 3 units are disposed/recycled. Part 1 has a release liner with biocompatible adhesive and film tape 5101 (attached to biocompatible foam tape 5102 for padding and optical compliance) that is used to attach the device to the patient. The release liner (tab) with adhesive tape and film at the opposite side 5104 is used to attach Part 1 to Part 2. Similarly, the release liner (tab) with adhesive tape and film 5112 in Part 3 is used to attach Part 3 to Part 2. Once the three parts are connected together, then the device can be attached to the patient for continuous monitoring (i.e., SpO2, PR, PI, waveforms, etc.). At the beginning of each monitoring shift (every 12 hours), for instance, the caregiver might want to replace Part 1 with a brand new one. This can be easily accomplished by pulling release liner (tab) 5103, and then attaching a brand new Part 1 to the device (Part 2). In the same way, every 24 hours, the caregiver can easily replace Part 3 with a new one by just pulling release liner (tab) 5113, and then attaching a brand new Part 3 to the device (Part 2). The battery and non-volatile memory are connected to the disposable oximeter circuitry (contacts 5108) via electrical contacts 5115 and electrically conductive adhesive tape 5114. The non-volatile memory 5117 is used to prevent product counterfeiting and piracy, and also to record battery usage so as notify the user when it is time to replace Part 3 or prevent a worn (counterfeited) Part 3 from being (re)used, and thereby putting at risk the safety of the patient. The non-volatile memory comes with an array of functionalities that have been architected to provide flexible security mechanisms to enable a wide range of authentication models designed to prevent product counterfeiting and piracy. There is in the market today a number of non-volatile memory systems specially designed to prevent counterfeit and control device/sensor usage, such as the Atmel's CryptoMemory® EEPROM family, or the Maxim Integrated's Single-Contact 1-Wire Interface DeepCover Secure Authenticator. The authentication of Part 3 5119 is performed by the main processor in Part 2 and the non-volatile memory in Part 3 via an authentication algorithm. In some embodiments, a secure co-processor works together with the oximeter main processor in Part 1 to authenticate Part 3 via its non-volatile secure memory. For the DeepCover Secure Authenticator architecture from Maxim Integrated, for instance, the authentication can be accomplished by using in Part 1 a DS28E35 DeepCover Secure Authenticator with 1-Wire ECDSA, and in Part 2 (in addition to the main processor), the DS2475 DeepCover ECDSA Co-Processor with 1-Wire Master so as to enable asymmetric authentication. This scheme provides very strong security and offloads ECDSA (Elliptic Curve Digital Signature Algorithm) computations and key storage from main processor in Part 2. The basic workflow of the disposable oximeter described in FIG. 51 (with package content example 5120 shown) can be summarized in the following steps:

1. Remove release liner 5104 and attach Part 1 to Part 2 as shown in FIG. 51;
2. Remove release liner 5112 and attach Part 3 to Part 2 as shown in FIG. 51;
3. Remove release liner 5101 and attach fully assembled disposable oximeter to the patient's measurement site (i.e., finger, temple, forehead, foot, etc.);
4. Monitor patient continuously and uninterruptedly for 12 hours;
5. Pull release tab 5103 to remove Part 1 and replace it with a new one following step 1;
6. Monitor patient continuously and uninterruptedly for another 12 hours;
7. Remove disposable oximeter from patient, pull release tab 5113 to remove Part 3 and release tab 5103 to remove Part 1 and replace them with new ones following step 1 and 2;
8. Repeat steps 3 through 7 every 24 hours for 5 days or until patient is released, whichever comes first.

The same workflow can be applied to different disposable oximeter packages sizes (such as the one 5120 in FIG. 51), depending on the battery capacity and the patient's adhesive tape replacement interval requirements.

A single-use, fully disposable, wireless, continuous pulse oximeter device like OXXIOM™ contains no outside connectors and its firmware programming typically happens during the manufacturing phase after its circuitry is assembled and tested. There are situations, however, where firmware upgrades are required for OXXIOM™ devices that have been already packaged and await to be shipped to customers, or that have been shipped to customers and await for activation. Firmware updates in medical devices take place often. The device manufacturer, by means of independent testing and/or customer complaints, determines the need for a firmware update that will lead to performance improvement and/or correction of undesired (and sometimes dangerous) behavior that may expose patients/users to unnecessary risks. When upgrades are necessary, the manufacturer conducts a correction/recall (for marketed devices that have left the direct control of the manufacturer), or a stock recovery (for devices that have not left the direct control of the manufacturer). Such procedures comprise of a series of steps and actions to be taken by a medical device manufacturer to correct the operation of its affected devices. In the case of OXXIOM™, in order to minimize the costs with corrections/recalls and/or stock recoveries associated with firmware updates, it is important to have an over-the-air upgrade capability implemented, so as to enable the programming of the latest firmware available at the moment the device (OXXIOM™) is activated by the user. FIG. 52 shows a flowchart 5201 that describes the phases and main steps that occur in the OXXIOM™'s lifecycle when such over-the-air firmware upgrade capability is needed. During the "Manufacturing" phase, OXXIOM™ circuitry is assembled, and a secure over-the-air upgrade capability firmware is programmed into the OXXIOM™'s processor. The devices are then encapsulated, packaged, and shipped to customer(s). During the "Operation" phase, the customer activates OXXIOM™ and pairs it with the host device (or connects to the OXXIOM™ cloud service via IPV6 over Bluetooth Smart (BLE)). The host app or the OXXIOM™ cloud service communicates with OXXIOM™'s secure over-the-air upgrade capability firmware and programs (into the non-volatile memory of the OXXIOM™'s processor) the latest application firmware image. OXXIOM™ then begins normal operation. When a new application firmware image is available, then "Application Firmware Image Update" phase takes place. In this phase, either a new host application (app) is released, containing the new application firmware image (and the user updates host device with new app), or the host app downloads, from a cloud storage service, the new application firmware image. In addition, in order to enable OXXIOM™ operation through IPV6 via Bluetooth Smart, the new application firmware image is also uploaded to the OXXIOM™ cloud service. In this way, OXXIOM™ units activated by customers will always be running the latest application firmware during normal operation. Such an approach can save time and resources that would be otherwise required if such firmware updates would have to be performed manually, device-by-device, during corrections/recalls or stock recoveries. It is essential to understand that a disposable single-use low-cost device like OXXIOM™ would need to be disassembled, in order to perform a manual firmware update and then encapsulated again, which would be possible (but costly) in a stock recovery procedure. However, such process would be very difficult during a correction/recall procedure because the OXXIOM™ units would already be at the customers' sites. This is not necessarily true for reusable medical devices since their higher cost and larger footprint allow for the inclusion of connectors/terminals, as part of their circuitry housing that enables firmware updates to be performed without the need for device disassembling. In an embodiment of the inventions, the OXXIOM™ device's processor is from Nordic Semiconductor, nRF51 (or nRF52) series, flash-based architecture that support over-the-air firmware updates. In this processor series, it is possible to conduct complete application and Bluetooth protocol stack over-the-air upgrades, which provide greater flexibility when compared to alternative static ROM/OTP-based processors.

Persons of ordinary skill in the art will understand that, among the many embodiments of the present inventions, a wide variety of combinations of elements and features can be beneficial and may be new and not obvious over prior art. Without being exhaustive, these may include:
1. The workflow such as shown in FIG. 37;
2. App functionalities such as those shown in FIGS. 39-45. Some examples include:
   (i) Processing of data sent by an oximeter to a host device, to be processed to estimate SpO2, PR and PI, and then display measurements and waveforms in real-time;
   (ii) Data stored for sharing and post-processing analysis such as the Sleep Study Oximetry report shown in FIG. 46;
   (iii) Barcode scanning for device pairing and patient identification;
3. A one-time switch with conductive tape and different contact layouts such as described in FIGS. 47 and 48;
4. An oximeter working in a network such as described in FIG. 49, including:
   (i) an oximeter having app functionalities as described herein;
   (ii) an oximeter with related cloud service via IPV6 through BLE, waveforms and measurements sent by a related cloud service to the hospital network to be processed in real-time for measurement and the display of waveforms in hospital monitors and mobile devices, network data storage for analysis and sharing with physicians and caregivers;
   (iii) an oximeter used at home, both with a host device and without a host device;
5. Improved battery chemistry (having a very flat voltage profile with discharge, being low-cost, and safe) and having a short-contact gap (being easy to align PCB and battery after soldering) for applications such as with an oximeter, such as described in FIG. 50;
6. An oximeter having multiple disposable pieces, such as shown in FIG. 51;
7. Over-the-air programming for oximeters, in order to simplify manufacturing, software updates, recalls, etc. for fully disposable solutions such as those described herein;
8. Recycling of oximeters, and/or the components thereof, such as described herein;
9. Low-cost ARM processor with radio functions and biosensing functions in combination with integrated low-cost frontend and LiMnO2 battery and boost-converter for the LEDs with larger band-gap voltage to enable a fully disposable, single-use, low cost, clinical-grade oximeter, such as described herein;
10. The combination of low-cost adhesive tapes with electronics to enable a low-cost, biocompatible encapsulation and one-time ON switch, such as described herein;
11. A distributed software architecture that (a) runs low-latency tasks such as those of oximeters of the invention, and (b) runs more complex/higher latency tasks in the host device or cloud service, such as described herein;
12. Alarm notifications sent to a caregiver(s) via text message or phone call when an alarm is triggered, such as shown in FIG. 43.

Various modifications and alterations of the inventions will become apparent to those skilled in the art without departing from the spirit and scope of the inventions, which is defined by the accompanying claims. It should be noted that steps recited in any method claims below do not necessarily need to be performed in the order that they are recited. Those of ordinary skill in the art will recognize variations in performing the steps from the order in which they are recited. In addition, the lack of mention or discussion of a feature, step, or component provides the basis for claims where the absent feature or component is excluded by way of a proviso or similar claim language.

While various embodiments of the present inventions have been described above, it should be understood that they have been presented by way of example only, and not of limitation. Likewise, the various diagrams may depict an example architectural or other configuration for the inventions, which is done to aid in understanding the features and functionality that may be included in the inventions. The inventions are not restricted to the illustrated example architectures or configurations, but the desired features may be implemented using a variety of alternative architectures and configurations. Indeed, it will be apparent to one of skill in the art how alternative functional, logical or physical partitioning and configurations may be implemented to implement the desired features of the present inventions. Also, a multitude of different constituent module names other than those depicted herein may be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

The previous description of the disclosed embodiments is provided to enable any person skilled in the art to make or use the present inventions. Various modifications to these embodiments will be readily apparent to those skilled in the art, and the generic principles defined herein may be applied to other embodiments without departing from the spirit or scope of the inventions.

Although the inventions are described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the inventions, whether or not such embodiments are described and whether or not such features are presented as being a part of a described embodiment. Thus the breadth and scope of the present inventions should not be limited by any of the above-described exemplary embodiments. Thus, the present inventions are not intended to be limited to the embodiments shown herein but are to be accorded the widest scope consistent with applicable law and the principles and novel features disclosed herein.

The invention claimed is:

1. An apparatus for gathering continuous medical data from a patient, including:
  a component assembly, comprising:
    an optical sensor attached to a printed circuit board, the optical sensor comprising at least one light emitter to emit light toward a measurement site of the patient and at least one light detector to detect light reflected from the measurement site, the at least one light emitter and the at least one light detector mounted in at least one optical cavity that includes one or more walls that are optically dark with respect to one or more light wavelength ranges of interest;
    a processor attached to the printed circuit board and operably connected to the optical sensor;
    a radio attached to the printed circuit board and operably connected to the processor;
    a battery operably connected to the optical sensor, the processor, and the radio;
    an antenna operably connected to the radio; and
    a memory operably connected to the processor and storing instructions, that when executed by the processor, cause operations of:
      modulating the at least one light emitter using a first modulation scheme or a second modulation scheme based on a determination that the apparatus is measuring a parameter related to blood, wherein:
        in the first modulation scheme:
          in a first period of time, only a first light wavelength range is turned on for approximately twenty-five percent of the modulation time cycle, only a second light wavelength range is turned on for approximately twenty-five percent of a modulation time cycle, and both the first light wavelength range and the second light wavelength range are turned off for approximately fifty percent of the modulation time cycle; and
          in a second period of time, only a third light wavelength range is turned on for approximately twenty-five percent of the modulation time cycle, only the second light wavelength range is turned on for approximately twenty-five percent of the modulation time cycle, and both the third light wavelength range and the second light wavelength range are turned off for approximately fifty percent of the modulation time cycle; or
        in the second modulation scheme:
          only a first wavelength range is turned on for approximately twenty-five percent of a modulation time cycle, only a second light wavelength range is turned on for approximately twenty-five percent of the modulation time cycle, and both the first light wavelength range and the second light wavelength range are turned off for approximately fifty percent of the modulation time cycle; and
  an encapsulation material encapsulating the component assembly and configured to attach the apparatus to the measurement site using an adhesive on a surface of the encapsulation material.

2. The apparatus of claim 1, wherein the battery includes a chemistry that provides a flat voltage profile with discharge and has a short-contact gap.

3. The apparatus of claim 1, wherein:
  the memory further stores data for a duration of a patient's sleep cycle; and
  the battery stores sufficient power to enable continuous monitoring of the measurement site for the duration of a patient's sleep cycle.

4. The apparatus of claim 1, wherein the antenna comprises a small-loop SMD antenna.

5. A method of gathering continuous medical data from a patient, including:
  providing the apparatus of claim 1;
  affixing the apparatus to a patient; and
  gathering the medical data.

6. The apparatus of claim 1, wherein the encapsulation material comprises a biocompatible adhesive tape.

7. The apparatus of claim 1, wherein the optical sensor includes an emitter-detector separation in the range of 2.5 to 7 mm.

8. The apparatus of claim 1, wherein the component assembly executes time critical, high frequency, low latency or low complexity tasks and wirelessly transmits waveform data or parameters.

9. The apparatus of claim 1, wherein the radio wirelessly transmits at least one of a waveform, a control signal, or a measurement.

10. The apparatus of claim 1, further including a bandage configured to attach the apparatus to the patient to increase at least one of:
  optical compliance of the optical sensor and the patient's skin;

optical penetration depth and minimize light piping and optical interference effects; or an amplitude of the photoplethysmograph to improve signal-to-noise ratio of data collected by the assembly.

11. The apparatus of claim 1, wherein at least one component of the component assembly is modular and separately connectable to the component assembly and is replaceable separately from disposing of the entire component assembly.

12. The apparatus of claim 11, wherein at least one separately connectable component includes the battery.

13. The apparatus of claim 11, wherein at least one separately connectable component includes a memory.

14. The apparatus of claim 1, wherein the component assembly communicates, via the antenna, with an application executing on a host device, the application configured to receive the transmitted data and process at least one of high latency tasks or high complexity tasks based on the data, the tasks including estimating at least one of an oxygen saturation level of blood, a pulse rate, or a blood perfusion index of the patient.

15. The apparatus of claim 1, further comprising a single-use turn-on switch to enable the apparatus to start operation, the switch activated by a removal of a removable first tab positioned through the encapsulation material.

16. The apparatus of claim 15, wherein the single-use turn-on switch is fabricated from at least one part each of conductive tape, conductive adhesive, and liner material.

17. The apparatus of claim 15, wherein the memory stores firmware, that when executed by the processor, causes the apparatus to receive wirelessly automatic updates upon activation of the single-use turn-on switch.

18. The apparatus of claim 1, further comprising a removable second tab attached to the encapsulation material, wherein removal of the second tab provides the adhesive on the surface of the encapsulation material that is used to attach the apparatus to the measurement site.

19. The apparatus of claim 18, wherein the removable second tab includes an identification label for the apparatus.

20. The apparatus of claim 1, wherein the memory stores further instructions, that when executed by the processor, cause operations comprising:

determine whether the measurement site has low perfusion or is subject to motion;

based on a determination that the measurement site does not have low perfusion or is not subject to motion, modulate the at least one light emitter based on a third modulation scheme, wherein in the third modulation scheme only a first wavelength range is turned on for approximately twenty-five percent of a modulation time cycle, only a second light wavelength range is turned on for approximately twenty-five percent of the modulation time cycle, and both the first light wavelength range and the second light wavelength range are turned off for approximately fifty percent of the modulation time cycle; and based on a determination that the measurement site has low perfusion or is subject to motion, modulate the at least one light emitter based on a second modulation scheme or a third modulation scheme, wherein:

in the fourth modulation scheme:

in a first period of time, only a first light wavelength range is turned on for approximately twenty-five percent of the modulation time cycle, only a second light wavelength range is turned on for approximately twenty-five percent of a modulation time cycle, and both the first light wavelength range and the second light wavelength range are turned off for approximately fifty percent of the modulation time cycle; and in a second period of time, only a third light wavelength range is turned on for approximately twenty-five percent of the modulation time cycle, only the second light wavelength range is turned on for approximately twenty-five percent of the modulation time cycle, and both the third light wavelength range and the second light wavelength range are turned off for approximately fifty percent of the modulation time cycle; or in the fifth modulation scheme each light wavelength range is turned on and off sequentially over time.

21. The apparatus of claim 1, wherein the memory stores further instructions, that when executed by the processor, cause operations comprising:

determine whether the apparatus is measuring a value other than a parameter related to blood; and based on a determination that the apparatus is measuring a value other than a parameter related to blood, modulate the at least one light emitter based on a third modulation scheme, wherein in the third modulation scheme each light wavelength range is turned on and off sequentially over time.

22. A wireless disposable single-use continuous pulse oximeter sensor assembly, comprising:

a component assembly, including:

an optical sensor attached to a printed circuit board, the optical sensor comprising at least one light emitter to emit light toward a measurement site of a patient and at least one light detector to detect light reflected from the measurement site, the at least one light emitter and the at least one light detector mounted in at least one optical cavity that includes one or more walls that are optically dark with respect to one or more light wavelength ranges of interest;

a radio attached to the printed circuit board;

an antenna operably connected to the radio;

a battery operably connected to the optical sensor and the radio;

a processor attached to the printed circuit board and operably connected to the optical sensor, the radio, and the battery; and a memory operably connected to the processor and storing instructions that when executed by the processor, cause operations of:

modulating the at least one light emitter using a first modulation scheme or a second modulation scheme based on a determination that the pulse oximeter sensor assembly is measuring a parameter related to blood, wherein:

in the first modulation scheme:

in a first period of time, only a first light wavelength range is turned on for approximately twenty-five percent of the modulation time cycle, only a second light wavelength range is turned on for approximately twenty-five percent of a modulation time cycle, and both the first light wavelength range and the second light wavelength range are turned off for approximately fifty percent of the modulation time cycle; and in a second period of time, only a third light wavelength range is turned on for approximately twenty-five percent of the modulation time cycle, only the second light wavelength range is turned on for approximately twenty-five percent of the modulation time cycle, and both the third light wavelength range and the second light wavelength range are turned off for approximately fifty percent of the modulation time cycle; or in the second modulation scheme:
only a first wavelength range is turned on for approximately twenty-five percent of a modulation time cycle, only a second light wavelength range is turned on for approximately twenty-five percent of the modulation time cycle, and both the first light wavelength range and the second light wavelength range are turned off for approximately fifty percent of the modulation time cycle;

processing at least one of a low latency task or a low complexity task based on data received from the optical sensor; and causing wireless transmission, via the radio and the antenna, of processed data associated with the low latency task or the low complexity task to at least one host device, wherein the host device is operable to process the processed data to estimate at least one of an oxygen saturation level of blood, a pulse rate, or a blood perfusion index of the patient; and an encapsulation material encapsulating the component assembly and configured to attach the pulse oximeter sensor assembly to the measurement site using an adhesive on a surface of the encapsulation material.

23. The wireless disposable single-use continuous pulse oximeter sensor assembly of claim 22, wherein the encapsulation material comprises a biocompatible tape.

24. The wireless disposable single-use continuous pulse oximeter sensor assembly of claim 22, wherein the processed data comprises at least one of waveform data or parameters.

25. The wireless disposable single-use continuous pulse oximeter sensor assembly of claim 22, wherein the at least one host device includes a mobile device.

26. The wireless disposable single-use continuous pulse oximeter sensor assembly of claim 22, wherein the at least one host device includes a network-based service and the service communicates output to at least one monitor.

27. The wireless disposable single-use continuous pulse oximeter sensor assembly of claim 26, wherein the at least one monitor is within the same room as the patient.

28. The wireless disposable single-use continuous pulse oximeter sensor assembly of claim 26, wherein the at least one monitor is not within the same room as the patient.

* * * * *